| (12) | United States Patent | (10) Patent No.: | US 7,078,214 B2 |
|---|---|---|---|
| | Basten et al. | (45) Date of Patent: | Jul. 18, 2006 |

(54) ASPERGILLUS PHENYLALANINE AMINOPEPTIDASE

(75) Inventors: Danielle Basten, Wageningen (NL); Petrus Jacobus Theodorus Dekker, Den Haag (NL); Paul William Schuurhuizen, Delft (NL); Jacob Visser, Wageningen (NL); Petrus Johannes Schaap, Hoorn (NL)

(73) Assignee: DSM IP Assets B.V., Heerleen (NL)

( * ) Notice: Subject to any disclaimer, the term of this patent is extended or adjusted under 35 U.S.C. 154(b) by 13 days.

(21) Appl. No.: 10/344,741

(22) PCT Filed: Aug. 22, 2001

(86) PCT No.: PCT/EP01/09925

§ 371 (c)(1),
(2), (4) Date: Jul. 29, 2003

(87) PCT Pub. No.: WO02/16618

PCT Pub. Date: Feb. 28, 2002

(65) Prior Publication Data

US 2004/0038371 A1    Feb. 26, 2004

(30) Foreign Application Priority Data

Aug. 23, 2000   (EP) .................. 00202995

(51) Int. Cl.
*C12N 9/48*      (2006.01)
*C12N 15/00*     (2006.01)
*C12N 5/00*      (2006.01)
*C12N 1/20*      (2006.01)
*C12Q 1/37*      (2006.01)

(52) U.S. Cl. .................. 435/212; 435/24; 435/69.1; 435/325; 435/252.3; 435/320.1; 536/23.2; 426/63; 426/42; 426/20; 426/549; 426/582; 426/656

(58) Field of Classification Search .............. 435/24, 435/212, 325, 252.3, 320.1, 69.1; 426/63, 426/42, 20, 549, 582, 656; 530/350, 23.2; 536/23.2

See application file for complete search history.

(56) References Cited

FOREIGN PATENT DOCUMENTS

| WO | WO 96/38549 | 12/1996 |
|---|---|---|
| WO | WO 98/51804 | 11/1998 |

OTHER PUBLICATIONS

Witkowski et al., Biochemistry 38:11643-11650, 1999.*
Seffernick et al., J. Bacteriol. 183(8):2405-2410, 2001.*

* cited by examiner

*Primary Examiner*—Rebecca E. Prouty
*Assistant Examiner*—Delia M. Ramirez
(74) *Attorney, Agent, or Firm*—Morrison & Foerster LLP

(57) ABSTRACT

The present invention describes isolated polypeptides from fungi which have aminopeptidase activity and isolated polynucleotides encoding the polypeptides. The invention also relates to nucleic acid constructs, vectors, and host cells comprising the polynucleotides as well as methods for producing and using the polypeptides.

17 Claims, 17 Drawing Sheets

```
          10        20        30        40
   ....|....|....|....|....|....|....|....|
GCTCCCTTCGGCACTTGGGACAGTCCCATTACAGCCGCAA  40
CCCTGACGTCCAAAGGCATCAGTTTCTCCGGCATCGCGGC  80
CACAGTTCGTCCCCTTCTCCTCTGTATCCTACTACGTCGA  120
ATTAAATTGACCTCTCCCTGCAGGCGGATGGTACCATCTA  160
CGTGAATGAAGGCCGCCCTGCCGAAGAAGGTCGCAATTGT  200
ATTGTCGAATGGCGCAACAACCAGCCCGTGACGTTTTAC  240
CAGCTGCCTACAGTGCCCGCACAGCCGTCCACGGCTACGG  280
CGGCGCGGCGTTCAACACCACGTCAGACGGAAAGGTGATC  320
TTCGCAGACTGGAAAACTCACGGGGTGTATATCCTTGATC  360
CTGCCACTTGTGATGTAACAGCAGCCGTGGAACCGGACGA  400
AAAGATCTGGTACGCTGCGTTCAATTCCCACCCCAAGAGA  440
CCAGAATTGGTGTTTGCTATCAGGGAGGATCACCACGGCA  480
AGGAGGTGGTCAATGAGCTTGTTGTAATCAATACCGGGAA  520
TAAGAAGGTGGAGGTTGCAGCGACGGGAGCGGACTTTTAC  560
TCGCATCCACGTTCAGCCCTGCTGGTGATAGAGTGTCTT  600
GGATCCAGTGGAACCATCCCGAGATGCCGTGGACGGGAAC  640
TGAGTTGTTTTCCGCACCGTGGAAGGATGAGAAGGTTGGA  680
ACCCCTGTGAAATTGGCAGGGAATGGCGATGAAGAAAGTA  720
TCTTGCAGCCGAGATGGGGACCAGACGGAAC  751
```

Fig. 4

```
           10        20        30        40              Page 1
   ....|....|....|....|....|....|....|....|
CTCGAGATCCGACGATATGCACCATACCTGATCGAAAGTA  40
ACATGCAAATTTTCATTGATGGAGGCATTCGACGTGGAAC  80
AGATGTCCTGAAGGCCCTTGCATTAGGAGCAACTGCTGTT  120
GGGCTTGGGCGACCATTTCTGTTCAGTCTGGCAGCCGGCT  160
ATGGAGCAGATGGGACCCGCCGGGCCATTCAAATCTTGCG  200
GCAGGAAATTGAAATGAACATGGTGTTCCTGGGCGTGACA  240
AAGCTGTCGGAATTGGGGCCTCATTGGTGAATTCAATGA   280
GGCTGGAACGAGATGTAGTTGGCTCGGTTAAACTGTGAAG  320
AGGCAGGCTTCTGTAGATTACTGGATATGAATATCTCCCC  360
AATTCATATGGCATTGTTCACATCCAGGCACAGCCTTAAC  400
CAGGACACAGACCAGTTCGCACTAAATGGAATTAAGAGGG  440
GCATGGGCTGACCAGTGCATATTAGTGCGTAAGCACTATT  480
CCCCATGTAACTGGCACGGGCTTATCGAAGCCATTCGGAT  520
CGCGGGAACACCGCGGAACTAATCTGGCTGGTGGATGTCA  560
CAACGATGCTTGTGCTCAGTTCCCCTCCCTGCTAAATTTC  600
ACCCGGTACCTGATTATTGCACTACTTCAACCCCCTCATC  640
CGGCCACGTCCATCTTTCTTTTTACGCCCTCCAAAAATAT  680
TTCATCCATTCACTTACTCTCTAAGACACTCCCAATTTTC  720
CAGTCAACCAAATGGCTACCCCCGCAGAAGCTCAGACAGC  760
TCCCTTCGGCACTTGGGACAGTCCCATCACAGCCGCAACC  800
CTGACGTCCAAAGGCATCAGTTTCTCCGGCATCGCGGCCG  840
CGGTTCGTCCCCTTCTCCTCTATATCCTACTACGTCCGAA  880
TTAAATTGACCTCTCCCTTCAGGCGGATGGTACCATCTAC  920
GTGAATGAAGGCCGCCCTGCCGAAGAAGGTCGCAATTGTA  960
TCGTCGAATGGCGCAACAACCAGCCCCGTGACGTTTTACC  1000
AGCTGCCTACAGTGCCCGCACAGCCGTCCACGGCTACGGC  1040
GGCGCGGCGTTCAACACCACGTCAGACGGAAAGGTGATCT  1080
TCGCAGACTGGAAAACTCACGGGGTGTATATACTTGATCC  1120
TGCCACTTGTGATGTAACAGCAGCCGTGGAACCAGACGAA  1160
AAGATCTGGTACGCTGCGTTCAATTCCCACCCCAAGAGAC  1200
CAGAATTGGTGTTTGCTATCAGGGAGGATCACCACGGCAA  1240
GGAGGTGGTCAATGAGCTTGTCGTAATCAATACCGGGAAT  1280
AAGAAGGTGGAGGTTGCAGCGACGGGAGCGGACTTTTACT  1320
CGCATCCCACGTTCAGTCCTGCTGGTGATAGAGTGTCTTG  1360
GATCCAGTGGAACCATCCCGAGATGCCGTGGACGGGAACT  1400
GAGTTGTTTTCCGCACCGTGGAAGGATGAGAAGGTTGGAA  1440
CCCCTGTGAAATTGGCAGGGAATGGCGAAGAAGAAAGTAT  1480
CTTGCAACCGAGATGGGGACCAGACGGAACCTTGTTCTTT  1520
GTGTCGGATCGCACTGGATATTGGCAGTTTTATCGCTGGA  1560
GCCCGGATGAAAGTGATGAGCCCCGCGCTATCGTTATTGA  1600
AGGCCTGGAGAAGGGCGAGTTCGCTCACCCAGAATGGCTC  1640
CTGGGATCGTATGACTCCTAACCCTCCTGCTCACATAGTA  1680
TATATCTAACACGATGCAGTTGCACATATGTTCTTCCAAA  1720
CGCCAACACAATTGTTGCAGCCTGGACGCAAAACGCAACG  1760
GAGCGTCTCGTCATCATTGACCTCGAGAAAAACACCTATA  1800
```

Fig. 6a

```
           1810      1820      1830      1840
       ....|....|....|....|....|....|....|....|
       CCTTCCCCGCCCACATCGCATCGCTCACTGGCATCCAACA 1840
       CAGCGCCGTGGCCCTGACATCTCCCACCAGCATTGCCGTC 1880
       ATTGCCAGCACTCCCACTGCTCCCAGCACTGTCTACCACA 1920
       TCTCTCTCACCAACAACGATGCCTTCGCGCCAACCGTCCT 1960
       CCGCTCCTCCACCTCAGTCACCATCTCCGACACTTATTTT 2000
       TCTCGTGCCCAACACATCTCATTCCCGCGCACCATCTCCA 2040
       CCCATCCTGATACTCTCTCCCATGCATTTTCCTCCCTCC  2080
       CACGAATCCTAAGTACAGCAGTGCCCCGGGCGAGCTTCCC 2120
       CCGCTCATCATTACCATTCACGGCGGGCCCACCATCCACA 2160
       CCGACCCCGGCCTTAGCATGATGTGGCAGTACTACACCAC 2200
       ACGAGGATATGCCGTTGCCCTGCTCAACTACGCCGGCTCC 2240
       TCTGGCTACGGTCGTGCCTACCGCAAACTTCTTAATGGAA 2280
       GTTGGGGTGTGCTCGACGTGCACGACGCTGCAGACTGTGC 2320
       CCGCTACCTGATCTCCGAAGGCAAGGTGCACCCGTCCCGC 2360
       ATTGGCATCACTGGCGTTAGTTCCGGTGGATACGCCACTC 2400
       TCCAGGCAATCTGCATGTTCCCGACTCTCTTCACTGGTGC 2440
       AGTTAGCGTCTCTGGCATTAGTGATGTCGAAGCCCTCGTG 2480
       GCCGAAACACACAAGTTCGAAAGTCACTATGCCTTCCGCC 2520
       TACTATTCGATGATAAGGTGCCGGAGACTGAAGAAGAGAA 2560
       GCGGAAGGTGTATCGCGAGCGGAGCCCCAGGTTCCATGCA 2600
       GACAAAATCAAGGCCAAACTGCTGTTGTTGCAGGGCACGG 2640
       ACGATGAGATTGTGCCGTTGAACCAAGCGCAGGCGATGGC 2680
       TGATGATGTCCAGCGCAGCGGCGGGGTGGCCAAGTTGGTG 2720
       ATCTTTGAGGGCGAGGGACATGGGTACCCGCGGAAGGCGG 2760
       AGAATGGCTTGCAGGCTAAGGAGGTGGAAGAGGGCTGGTG 2800
       GAAGGTGAACTTGGCCGAGGTCAATGGGGAATGAGTGTGA 2840
       TACTAGCAGATTTTGTTGTGGATTGGTACAACAGAGTATC 2880
       AAGCACAGGGGGCCATCCAGTGAAAGAGATGTAAGCTACT 2920
       AGGCACATCTACGTTCTAGAATATAGAAAGTGTCGTGATC 2960
       TCCTCCATCACTACAACCAAATACTCGTAAAAATAGACTG 3000
       AAGTTCTTCGCGACCCCCAAGCTCGTGAGACAGGCCAGTA 3040
       AACCCAACCAACAAGTCACCGAACACTCCTAGAGATCGAT 3080
       CAATCATTATGCCTCGCCCACTAACCCGATAGAACAAAGC 3120
       TACCGTAGATGGTCGGTTTTCAATATACTCCACACCTATT 3160
       CGTCCATAAACAGACCAGGGACTAACCAACTAAAATATCC 3200
       AAATCCAACCAATGAGTTCAGTTCAGCCTTCATTCTCATC 3240
       ACACACTACATATAAAGAAAAGAGAATACACGCTAATCCT 3280
       CACAGCTACACGCCCCACACAAAAAAAAGACAAAAATGCT 3320
       CACACTCGGATTCGAACCGAGGATCTCATGATTACTAGTC 3360
       ATGCGCTTTACCAACTAAGCCATGCGAGCAATTGATGCTG 3400
       CTGATGCAGAATATTATGCTATACAGACCAACCTTAGAGT 3440
       ATCATCCTAGTGCTCAATCGGCTATGCAGTCACTCCACAC 3480
       CACCGAAATACAAAGAACAGATATAATCCAAGTCGTTATA 3520
       CATACAGCATGCCGGAATAGAATCTAAATTGACTAGCCAG 3560
       CCAGTCTACAGGTACTCGGGCTACGCACTGCAGCCAAGAC 3600
       ACCGAGATGGATAAATTAAGAACGGCGACGGTGTGGTTCT 3640
       CGTGGCCGGATGCTATCAGGATTTAATATGGAATGGATGA 3680
       CCGGGCTTCACTGAAACCCGAGATATGACGTACATAGTAG 3720
       CAACTTATTAGATTGTGGTCGCCGAGGTCTTTTGTCGGTG 3760
       TACAAGGGGTTTAGTTAGTAGTGACCGGATCGGGATCTGT 3800
```

Fig. 6b

```
           3810      3820      3830      3840                    Page 3
    ┴┴┴┴┴┴┴┴┴┴┴┴┴┴┴┴┴┴┴┴┴┴┴┴┴┴┴┴┴┴┴┴┴┴┴┴┴┴┴┴
    TGGTGTTGAATGCGTCGGGGACGGTGGTGGTGTTTGTGGA 3840
    GAAAGGGGTGAATGACATATGATGGCTTTTGTTCCGTACT 3880
    TTTTGGATTAACTTTGTTTTGCTGTCGGTGATAGATAAGC 3920
    TT    3922
```

Fig. 6c

| Substrate | Activity at pH 5.2 (%) | Activity at pH 7.2 (%) |
|---|---|---|
| Phe-pNA | 100 | 100 |
| Phe-βNA | 100 | 100 |
| Tyr-βNA | 72 | 53 |
| Trp-βNA | 27 | 22 |
| Leu-pNA | 10 | 14 |
| Met-pNA | 6 | 18 |
| Leu-βNA | 6 | 15 |
| Pro-pNA | <1 | 2 |
| Ala-pNA | <1 | <1 |
| Lys-pNA | <1 | <1 |
| NacA-pNA | <1 | <1 |
| Arg-pNA | <1 | <1 |
| Gly-pNA | <1 | <1 |
| Ile-pNA | <1 | <1 |
| Val-pNA | <1 | <1 |
| Glu-pNA | <1 | <1 |
| Asn-βNA | <1 | <1 |
| Thr-βNA | <1 | <1 |
| Ser-βNA | <1 | <1 |
| His-βNA | <1 | <1 |

ASPERGILLUS PHENYLALANINE AMINOPEPTIDASE

FIELD OF THE INVENTION

The present invention relates to the purification of an aminopeptidase from a crude culture filtrate of an *Aspergillus niger* strain, the isolation and characterization of the gene encoding the aminopeptidase, the over-expression of the gene in *Aspergillus niger*, the characterization of its biochemical properties, and the application of the aminopeptidase in the preparation of, for instance, protein hydrolysates.

BACKGROUND OF THE INVENTION

Many food products contain flavoring agents obtained by the hydrolysis of proteinaceous material. Conventionally hydrolysis is accomplished by using strong acid, followed by neutralization. Acid-hydrolysis requires the use of aggressive chemicals and can be energy consuming. Furthermore it often leads to the severe degradation of the amino acids obtained during hydrolysis.

Protein degrading enzymes can also be used to protein hydrolysis because they are less polluting than the strong, aggressive chemicals used in acid hydrolysis and are also capable of working under mild conditions that prevent the racemization of amino acids. Typically the aim of enzymatic hydrolysis of proteinaceous material is to obtain a high degree of hydrolysis, usually by using a cocktail of nonspecific-acting proteolytic enzymes, both endo-peptidases and exo-peptidases. Specific acting proteolytic enzymes are not used for this purpose because such enzymes provide an inadequate degree of hydrolysis. Conversely, where the aim is to produce specific amino acids or peptides from a complex protein without destroying the protein's physical properties (such as its elasticity, foaming properties or texture properties) specific acting enzymes are preferred.

Many microorganisms are able to produce endo-proteases and exo-proteases. In the food industry, Aspergilli have been widely used for a long time and are, therefore, in conformity with safety regulations in many countries all over the world. Among the Aspergilli, *Aspergillus niger* is the most widely used species in the food industry. *Aspergillus niger* has been used as a source of proteolytic enzymes in the past. For example, WO 96/38549 describes the production of a culture filtrate from an *Aspergillus niger* strain, the filtrate exhibiting aminopeptidase activity, and substantially lacking endo-proteolytic activity. However, the aminopeptidase activity in the crude filtrate was relatively low, and the source of the enzymatic activity was never isolated or specifically identified.

SUMMARY OF THE INVENTION

The present invention provides isolated polypeptides which have aminopeptidase activity, selected from the group consisting of:
(a) a polypeptide having an amino acid sequence which has at least 40% amino acid sequence identity with amino acids 1 to 663 of SEQ ID NO:2 or a fragment thereof; and
(b) a polypeptide which is encoded by a polynucleotide which hybridizes under low stringency conditions with (i) the nucleic acid sequence of SEQ ID NO:1 or a c-terminal fragment thereof which is at least 80% or 90% identical over 60, preferably over 100 nucleotides, more preferably at least 90% identical over 200 nucleotides, or (ii) a nucleic acid sequence complementary to the nucleic acid sequence of SEQ ID NO:1.

An isolated polypeptide of the invention may be further characterised by at least one of the following physicochemical properties:
(1) an optimal phenylalanine aminopeptidase activity at a pH ranging from 2 to 10, such as from 4 to 7, preferably from 4.5 to 6.5, optimally from 5 to 6;
(2) an optimal phenylalanine aminopeptidase activity at a temperature ranging from 35° C. to 70° C.;
(3) a molecular weight (deglycosylated) of approximately 72 kDa; and
(4) an isoelectric point of about 5.56

The present invention also provides an isolated polynucleotide which encodes a polypeptide of the invention and nucleic acid constructs, vectors, and host cells comprising such a polynucleotide as well as methods for producing and using the polypeptide.

BRIEF DESCRIPTION OF THE FIGURES

FIG. 4 shows the nucleic acid sequence of the 751 bp PCR fragment of the gene encoding the aminopeptidase isolated from *A. niger* NRRL 3112, corresponding to bases 241–991 of SEQ ID NO: 3.

FIG. 6A–C shows the primary sequence of the gene encoding the aminopeptidase isolated from *A. niger* N400 (SEQ ID NO:1).

Panel A shows the results of probing for aminopeptidase expression, while Panel B shows internal sample loading controls showing equal loading of ribosomal RNA.

Figure 10:
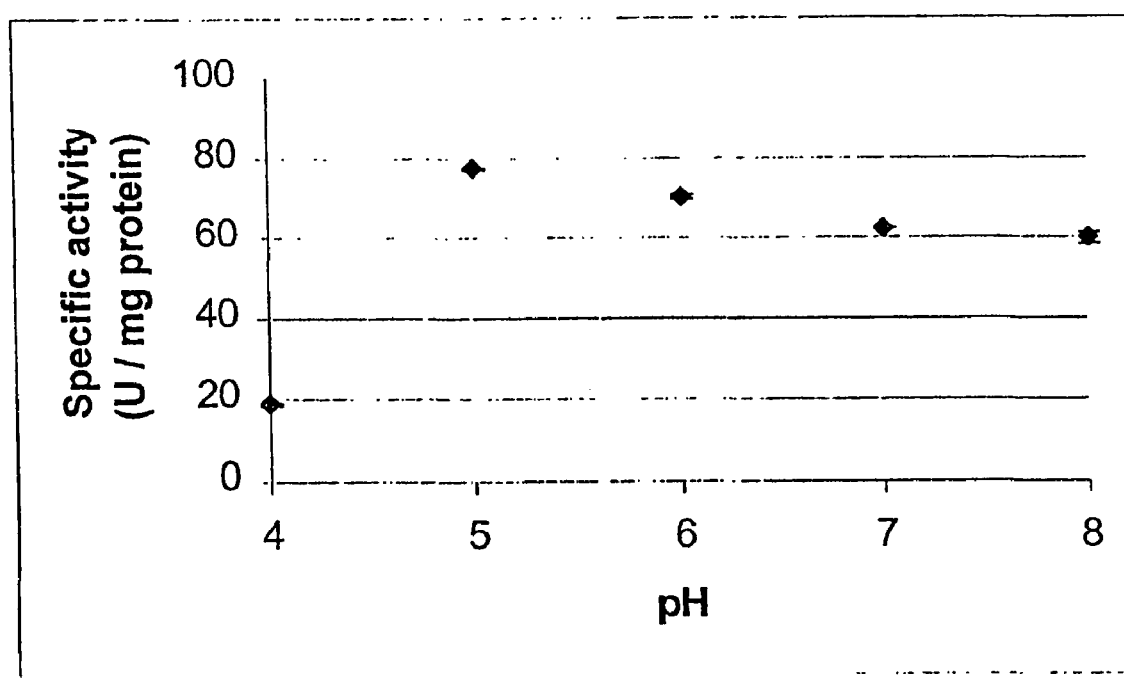

FIG. 10 shows the pH dependence of the hydrolysis of Phe-pNA catalyzed by the aminopeptidase at 30° C. using McIlvaine buffer.

Figure 11:
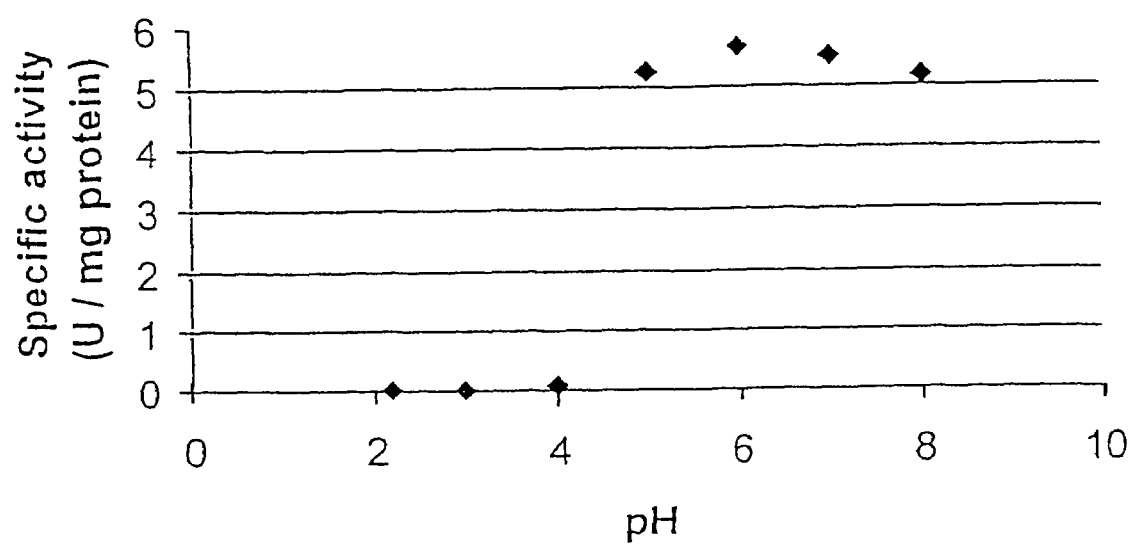

FIG. 11 shows the pH dependence of the hydrolysis of the Leu-pNA catalyzed by the aminopeptidase at 30° C. using McIlvaine buffer.

Figure 12:
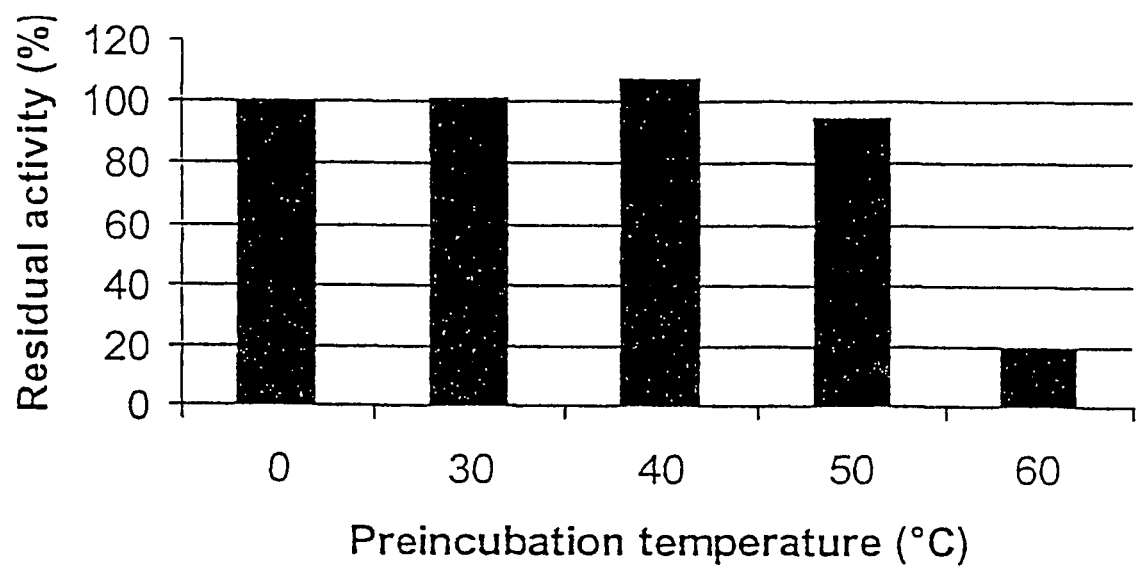

FIG. 12 shows the temperature stability of the aminopeptidase. Residual activity after pre incubation at several temperatures was calculated using a sample which was kept in ice for 1 has a reference.

FIG. 13 shows the substrate specificity of the aminopeptidase activity of the enzyme purified from *A. niger* mycelial extracts at pH 5.2 and 7.2. The % activity is relative to the activity towards Phe-pNA In case of the pNA substrates and relative to Phe-βNA In case of βNA substrates.

Figure 14:
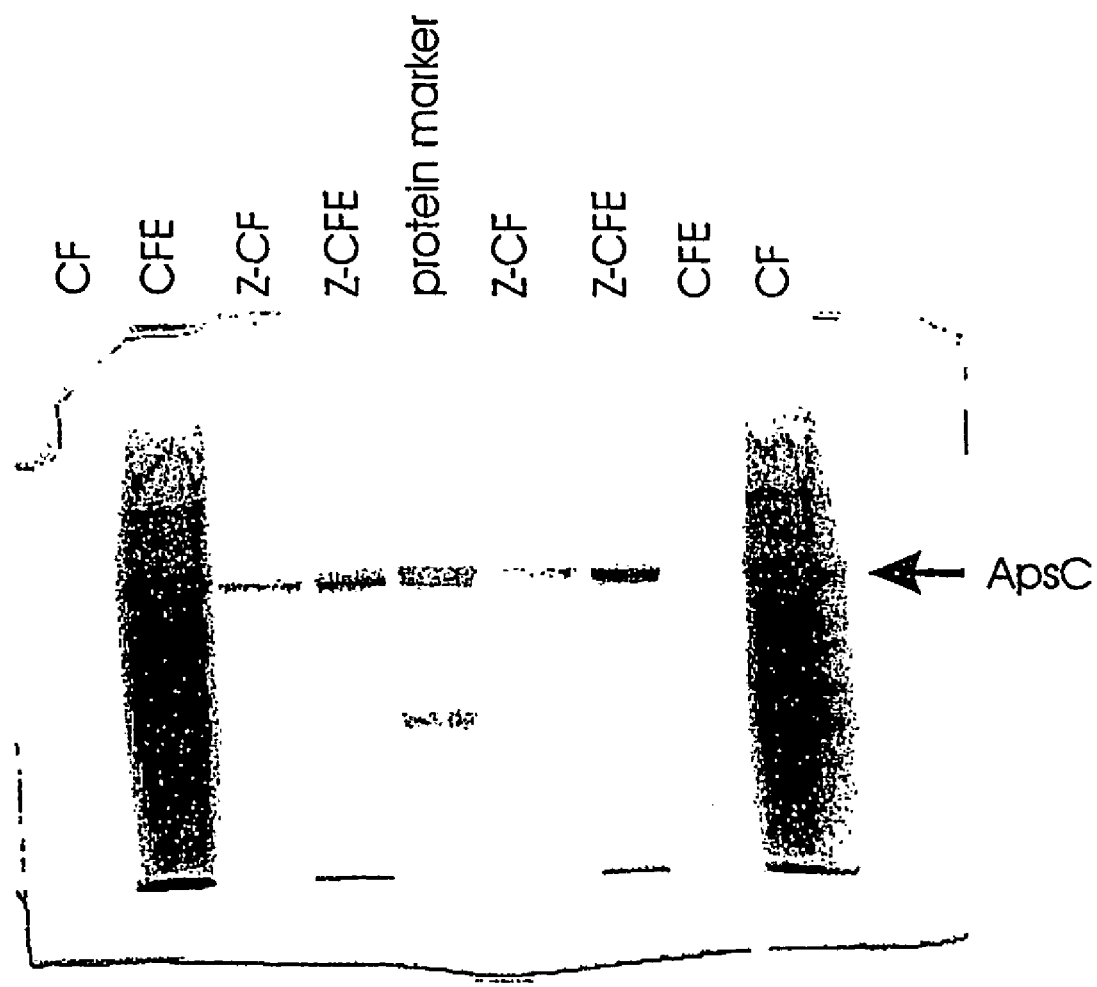

FIG. 14 shows SDS-PAGE analysis of aminopeptidase-containing media fractions, in which CF represents culture filtrate; CFE represents cell free extract; Z-CF represents aminopeptidase purified from culture filtrate; and Z-CFE represents aminopeptidase purified from cell free extracts. The aminopeptidase protein is indicated with an arrow.

Figure 15:

FIG. 15 shows a "zooblot" Southern analysis, in which a 1090 bp EcoRI-BamHI fragment probe from *A. niger* N400 (CBS 120.49) was hybridized to genomic DNA from *A. niger, A. tubingensis, A. foetidus* and *A. carbonarius*, and which indicates the presence of an orthologous aminopeptidase gene in each of these fungal strains.

DETAILED DESCRIPTION OF THE INVENTION

The present invention provides an isolated polypeptide which has aminopeptidase activity.

A polypeptide of the invention may be in an isolated form. As defined herein, an isolated polypeptide is an endogenously produced or a recombinant polypeptide which is essentially free from other non-aminopeptidase polypeptides, and is typically at least about 20% pure, preferably at least about 40% pure, more preferably at least about 60% pure, even more preferably at least about 80% pure, still more preferably about 90% pure, and most preferably about 95% pure, as determined by SDS-PAGE. The polypeptide may be isolated by centrifugation and chromatographic methods, or any other technique known in the art for obtaining pure proteins from crude solutions. It will be understood that the polypeptide may be mixed with carriers or diluents which do not interfere with the intended purpose of the polypeptide, and thus the polypeptide in this form will still be regarded as isolated. It will generally comprise the polypeptide in a preparation in which more than 20%, for example more than 30%, 40%, 50%, 80%, 90%, 95% or 99%, by weight of the proteins in the preparation is a polypeptide of the invention.

Preferably, the polypeptide of the invention is obtainable from a microorganism which possesses a gene encoding an enzyme with aminopeptidase activity. More preferably the microorganism is fungal, and optimally is a filamentous fungus. Preferred organisms are thus of the genus *Aspergillus*, such as those of the species *Aspergillus niger*.

"Aminopeptidase activity" is defined as the ability to release amino acids or small peptides from the amino-terminus of a (poly)peptide. Preferably the aminopeptidase may cleave in between two adjacent amino-acids. The substrate polypeptides may or may not be substituted, the amino-terminus may or may not be acylated (by i.e. acetylation). Preferably the aminopeptidase has a preference for the release of an aromatic amino acid from the substrate protein, more preferably, phenylalanine is released.

For the purposes of the present invention, aminopeptidase activity is determined by measuring the initial rate of hydrolysis of the L-phenylalanine-nitroanilide at 400 nm.

In a first embodiment, the present invention provides an isolated polypeptide having an amino acid sequence which has a degree of amino acid sequence identity to amino acids 1 to 663 of SEQ ID NO: 2 (i.e. the mature polypeptide) of at least about 40%, preferably at least about 50%, preferably at least about 60%, preferably at least about 65%, preferably at least about 70%, more preferably at least about 80%, even more preferably at least about 90%, still more preferably at least about 95%, and most preferably at least about 97%, and which has aminopeptidase activity.

For the purposes of the present invention, the degree of identity between two or more amino acid sequences is determined by BLAST P protein database search program (Altschul et al., 1997, Nucleic Acids Research 25: 3389–3402) with matrix Blosum 62 and an expected threshold of 10.

A polypeptide of the invention may comprise the amino acid sequence set forth in SEQ ID NO: 2 or a substantially homologous sequence, or a fragment of either sequence having aminopeptidase activity. In general, the naturally occurring amino acid sequence shown in SEQ ID NO: 2 is preferred.

The polypeptide of the invention may also comprise a naturally occurring variant or species homologue of the polypeptide of SEQ ID NO: 2.

A variant is a polypeptide that occurs naturally in, for example, fungal, bacterial, yeast or plant cells, the variant having aminopeptidase activity and a sequence substantially similar to the protein of SEQ ID NO: 2. The term "variants" refers to polypeptides which have the same essential character or basic biological functionality as the aminopeptidase of SEQ ID NO: 2, and includes allelic variants. The essential character of aminopeptidase of SEQ ID NO: 2 is that it is an enzyme capable of cleaving the amino-terminal amino acid from a protein or (poly)peptide. Preferably, a variant polypeptide has at least the same level of aminopeptidase activity as the polypeptide of SEQ ID NO: 2. Variants include allelic variants either from the same strain as the polypeptide of SEQ ID NO: 2, or from a different strain of the same genus or species.

Similarly, a species homologue of the inventive protein is an equivalent protein of similar sequence which is an aminopeptidase and occurs naturally in another species of Aspergillus.

Variants and species homologues can be isolated using the procedures described herein which were used to isolate the polypeptide of SEQ ID NO: 2 and performing such procedures on a suitable cell source, for example a bacterial, yeast, fungal or plant cell. Also possible is the use a probe of the invention to probe libraries made from yeast, bacterial, fungal or plant cells in order to obtain clones expressing variants or species homologues of the polypepetide of SEQ ID NO: 2. These clones can be manipulated by conventional techniques to generate a polypeptide of the invention which thereafter may be produced by recombinant or synthetic techniques known per se.

The sequence of the polypeptide of SEQ ID NO: 2 and of variants and species homologues can also be modified to provide polypeptides of the invention. Amino acid substitutions may be made, for example from 1, 2 or 3 to 10, 20 or 30 substitutions. The same number of deletions and insertions may also be made. These changes may be made outside regions critical to the function of the polypeptide, as such a modified polypeptide will retain its aminopeptidase activity.

Polypeptides of the invention include fragments of the above mentioned full length polypeptides and of variants thereof, including fragments of the sequence set out in SEQ ID NO: 2. Such fragments will typically retain activity as an aminopeptidase. Fragments may be at least 50, 100 or 200 amino acids long or may be this number of amino acids short of the full length sequence shown in SEQ ID NO: 2.

Polypeptides of the invention can, if necessary, be produced by synthetic means although usually they will be made recombinantly as described below. Synthetic polypeptides may be modified, for example, by the addition of histidine residues or a T7 tag to assist their identification or purification, or by the addition of a signal sequence to promote their secretion from a cell.

Thus, the variants sequences may comprise those derived from strains of Aspergillus other than the strain from which the polypeptide of SEQ ID NO: 2 was isolated. Variants can be identified from other Aspergillus strains by looking for aminopeptidase activity and cloning and sequencing as described herein. Variants may include the deletion, modification or addition of single amino acids or groups of amino acids within the protein sequence, as long as the peptide maintains the basic biological functionality of the aminopeptidase of SEQ ID NO: 2.

Amino acid substitutions may be made, for example from 1, 2 or from 3 to 10, 20 or 30 substitutions. The modified polypeptide will generally retain activity as an aminopeptidase. Conservative substitutions may be made; such substitutions are well known in the art. Preferably substitutions do not affect the folding or activity of the polypeptide.

Shorter polypeptide sequences are within the scope of the invention. For example, a peptide of at least 50 amino acids or up to 60, 70, 80, 100, 150 or 200 amino acids in length is considered to fall within the scope of the invention as long as it demonstrates the basic biological functionality of the aminopeptidase of SEQ ID NO: 2. In particular, but not exclusively, this aspect of the invention encompasses the situation in which the protein is a fragment of the complete protein sequence.

In a second embodiment, the present invention provides an to isolated polypeptide which has aminopeptidase activity, and is encoded by polynucleotides which hybridize or are capable of hybrizing under low stringency conditions, more preferably medium stringency conditions, and most preferably high stringency conditions, with (I) the nucleic acid sequence of SEQ ID NO: 1 or a nucleic acid fragment comprising at least the c-terminal portion of SEQ ID NO: 1, but having less than all or having bases differing from the bases of SEQ ID NO: 1; or (ii) with a nucleic acid strand complementary to SEQ ID NO: 1.

The term "capable of hybridizing" means that the target polynucleotide of the invention can hybridize to the nucleic acid used as a probe (for example, the nucleotide sequence set forth in SEQ. ID NO: 1, or a fragment thereof, or the complement of SEQ ID NO: 1) at a level significantly above background. The invention also includes the polynucleotides that encode the amino peptidases of the invention, as well as nucleotide sequences which are complementary thereto. The nucleotide sequence may be RNA or DNA, including genomic DNA, synthetic DNA or cDNA. Preferably, the nucleotide sequence is DNA and most preferably a genomic DNA sequence. Typically, a polynucleotide of the invention comprises a contiguous sequence of nucleotides which is capable of hybridizing under selective conditions to the coding sequence or the complement of the coding sequence of SEQ ID NO: 1. Such nucleotides can be synthesized according to methods well known in the art.

A polynucleotide of the invention can hybridize to the coding sequence or the complement of the coding sequence of SEQ ID NO:1 at a level significantly above background. Background hybridization may occur, for example, because of other cDNAs present in a cDNA library. The signal level generated by the interaction between a polynucleotide of the invention and the coding sequence or complement of the coding sequence of SEQ ID NO: 1 is typically at least 10 fold, preferably at least 20 fold, more preferably at least 50 fold, and even more preferably at least 100 fold, as intense as interactions between other polynucleotides and the coding sequence of SEQ ID NO: 1. The intensity of interaction may be measured, for example, by radiolabelling the probe, for example with $^{32}P$. Selective hybridization may typically be achieved using conditions of low stringency (0.3M sodium chloride and 0.03M sodium citrate at about 40° C.), medium stringency (for example, 0.3M sodium chloride and 0.03M sodium citrate at about 50° C.) or high stringency (for example, 0.3M sodium chloride and 0.03M sodium citrate at about 60° C.).

Modifications

Polynucleotides of the invention may comprise DNA or RNA. They may be single or double stranded. They may also be polynucleotides which include within them synthetic or modified nucleotides including peptide nucleic acids. A number of different types of modifications to polynucleotides are known in the art. These include a methylphosphonate and phosphorothioate backbones, and addition of acridine or polylysine chains at the 3' and/or 5' ends of the molecule. For the purposes of the present invention, it is to be understood that the polynucleotides described herein may be modified by any method available in the art.

It is to be understood that skilled persons may, using routine techniques, make nucleotide substitutions that do not affect the polypeptide sequence encoded by the polynucleotides of the invention to reflect the codon usage of any particular host organism in which the polypeptides of the invention are to be expressed.

The coding sequence of SEQ ID NO: 1 may be modified by nucleotide substitutions, for example from 1, 2 or 3 to 10, 25, 50 or 100 substitutions. The polynucleotide of SEQ ID NO: 1 may alternatively or additionally be modified by one or more insertions and/or deletions and/or by an extension at either or both ends. The modified polynucleotide generally encodes a polypeptide which has aminopeptidase activity. Degenerate substitutions may be made and/or substitutions may be made which would result in a conservative amino acid substitution when the modified sequence is translated, for example as discussed with reference to polypeptides later.

Homologues

A nucleotide sequence which is capable of selectively hybridizing to the complement of the DNA coding sequence of SEQ ID NO: 1 is included in the invention and will generally have at least 50% or 60%, at least 70%, at least 80%, at least 90%, at least 95%, at least 98% or at least 99% sequence identity to the coding sequence of SEQ ID NO: 1 over a region of at least 60, preferably at least 100, more preferably at least 200 contiguous nucleotides or most preferably over the full length of SEQ ID NO: 1. Likewise, a nucleotide which encodes an active aminopeptidase and which is capable of selectively hybridizing to a fragment of a complement of the DNA coding sequence of SEQ ID NO: 1, is also embraced by the invention. A C-terminal fragment of the nucleic acid sequence of SEQ ID NO:1 which is at least 80% or 90% identical over 60, preferably over 100 nucleotides, more preferably at least 90% identical over 200 nucleotides is encompassed by the invention.

Any combination of the above mentioned degrees of identity and minimum sizes may be used to define polynucleotides of the invention, with the more stringent combinations (i.e. higher identity over longer lengths) being preferred. Thus, for example, a polynucleotide which is at least 80% or 90% identical over 60, preferably over 100 nucleotides, forms one aspect of the invention, as does a polynucleotide which is at least 90% identical over 200 nucleotides.

The UWGCG Package provides the BESTFIT program which may be used to calculate identity (for example used on its default settings).

The PILEUP and BLAST N algorithms can also be used to calculate sequence identity or to line up sequences (such as identifying equivalent or corresponding sequences, for example on their default settings).

Software for performing BLAST analyses is publicly available through the National Center for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighborhood word score threshold. These initial neighborhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix alignments (B) of 50, expectation (E) of 10, M=5, N=4, and a comparison of both strands.

The BLAST algorithm performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

Primers and Probes

Polynucleotides of the invention include and may be used as primers, for example as polymerase chain reaction (PCR) primers, as primers for alternative amplification reactions, or as probes for example labelled with a revealing label by conventional means using radioactive or non-radioactive labels, or the polynucleotides may be cloned into vectors. Such primers, probes and other fragments will be at least 20, for example at least 25, 30 or 40 nucleotides in length. They will typically be up to 40, 50, 60, 70, 100, 150, 200 or 300 nucleotides in length, or even up to a few nucleotides (such as 5 or 10 nucleotides) short of the coding sequence of SEQ ID NO: 1.

In general, primers will be produced by synthetic means, involving a step-wise manufacture of the desired nucleic acid sequence one nucleotide at a time. Techniques for accomplishing this using automated protocols are readily available in the art. Examples of primers of the invention are set forth in Table 1 (SEQ ID NOs.: 4–10), and Table 3 (SEQ ID NOs.:13–21, SEQ ID NO.: 6)

Longer polynucleotides will generally be produced using recombinant means, for example using PCR cloning techniques. This will involve making a pair of primers (typically of about 15–30 nucleotides) to amplify the desired region of the aminopeptidase to be cloned, bringing the primers into contact with mRNA, cDNA or genomic DNA obtained from a yeast, bacterial, plant, prokaryotic or fungal cell, preferably of an *Aspergillus* strain, performing a polymerase chain reaction under conditions suitable for the amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

Such techniques may be used to obtain all or part of the polynucleotides encoding the aminopeptidase sequences described herein. Introns, promoter and trailer regions are within the scope of the invention and may also be obtained in an analogous manner (e.g. by recombinant means, PCR or cloning techniques), starting with genomic DNA from a fungal, yeast, bacterial plant or prokaryotic cell.

The polynucleotides or primers may carry a revealing label. Suitable labels include radioisotopes such as $^{32}P$ or $^{35}S$, enzyme labels, or other protein labels such as biotin. Such labels may be added to polynucleotides or primers of the invention and may be detected using techniques known to persons skilled in the art.

Polynucleotides or primers (or fragments thereof) labelled or unlabelled may be used in nucleic acid-based tests for detecting or sequencing an aminopeptidase or a variant thereof in a fungal sample. Such detection tests will generally comprise bringing a fungal sample suspected of containing the DNA of interest into contact with a probe comprising a polynucleotide or primer of the invention under hybridizing conditions, and detecting any duplex formed between the probe and nucleic acid in the sample. Detection may be achieved using techniques such as PCR or by immobilizing the probe on a solid support, removing any nucleic acid in the sample which is not hybridized to the probe, and then detecting any nucleic acid which is hybridized to the probe. Alternatively, the sample nucleic acid may be immobilized on a solid support, the probe hybridized and the amount of probe bound to such a support after the removal of any unbound probe detected.

The probes of the invention may conveniently be packaged in the form of a test kit in a suitable container. In such kits the probe may be bound to a solid support where the assay format for which the kit is designed requires such binding. The kit may also contain suitable reagents for treating the sample to be probed, hybridizing the probe to nucleic acid in the sample, control reagents, instructions, and the like. The probes and polynucleotides of the invention may also be used in microassay.

Preferably, the polynucleotide of the invention is obtainable from the same organism as the polypeptide, such as a fungus, in particular a fungus of the genus *Aspergillus*.

The polynucleotides of the invention also include variants of the sequence of SEQ ID NO: 1 which encode for a polypeptide having aminopeptidase activity. Variants may be formed by additions, substitutions and/or deletions. Such variants of the coding sequence of SEQ ID NO:1 may thus encode polypeptides which have the ability to remove amino acids from the amino terminus of a polypeptide.

Production of Polynucleotides

Polynucleotides which do not have 100% Identity with SEQ ID NO: 1 but fall within the scope of the invention can be obtained in a number of ways. Thus, variants of the aminopeptidase sequence described herein may be obtained for example, by probing genomic DNA libraries made from a range of organisms, such as those discussed as sources of the polypeptides of the invention. In addition, other fungal, plant or prokaryotic homologues of aminopeptidase may be obtained and such homologues and fragments thereof in general will be capable of hybridising to SEQ ID NO: 1. Such sequences may be obtained by probing cDNA libraries or genomic DNA libraries from other species, and probing such libraries with probes comprising all or part of SEQ ID. 1 under conditions of medium to high stringency (as described earlier). Nucleic acid probes comprising all or part of SEQ ID NO: 1 may be used to probe cDNA or genomic libraries from other species, such as those described as sources for the polypeptides of the invention.

Species homologues may also be obtained using degenerate PCR, which uses primers designed to target sequences within the variants and homologues which encode conserved amino acid sequences. The primers can contain one or more degenerate positions and will be used at stringency conditions lower than those used for cloning sequences with single sequence primers against known sequences.

Alternatively, such polynucleotides may be obtained by site directed mutagenesis of the aminopeptidase sequences or variants thereof. This may be useful where, for example, silent codon changes to sequences are required to optimize codon preferences for a particular host cell in which the polynucleotide sequences are being expressed. Other sequence changes may be made in order to introduce restriction enzyme recognition sites, or to alter the property or function of the polypeptides encoded by the polynucleotides.

The invention includes double stranded polynucleotides comprising a polynucleotide of the invention and its complement.

The present invention also provides polynucleotides encoding the polypeptides of the invention described above. Since such polynucleotides will be useful as sequences for recombinant production of polypeptides of the invention, it is not necessary for them to be capable of hybridising to the sequence of SEQ ID NO: 1, although this will generally be desirable. Otherwise, such polynucleotides may be labelled, used, and made as described above if desired.

Recombinant Polynucleotides.

The invention also provides vectors comprising a polynucleotide of the invention, including cloning and expression vectors, and in another aspect methods of growing, transforming or transfecting such vectors into a suitable host cell, for example under conditions in which expression of a polypeptide of, or encoded by a sequence of, the invention occurs. Provided also are host cells comprising a polynucleotide or vector of the invention wherein the polynucleotide is heterologous to the genome of the host cell. The term "heterologous", usually with respect to the host cell, means that the polynucleotide does not naturally occur in the genome of the host cell or that the polypeptide is not naturally produced by that cell. Preferably, the host cell is a yeast cell, for example a yeast cell of the genus *Kluyveromyces* or *Saccharomyces* or a filamentous fungal cell, for example of the genus *Aspergillus*.

Polynucleotides of the invention can be incorporated into a recombinant replicable vector, for example a cloning or expression vector. The vector may be used to replicate the nucleic acid in a compatible host cell. Thus, in a further embodiment, the invention provides a method of making polynucleotides of the invention by introducing a polynucleotide of the invention into a replicable vector, introducing the vector into a compatible host cell, and growing the host cell under conditions which bring about replication of the vector. The vector may be recovered from the host cell. Suitable host cells are described below in connection with expression vectors.

Vectors

The vector into which the expression cassette of the invention is inserted may be any vector that may conveniently be subjected to recombinant DNA procedures, and the choice of the vector will often depend on the host cell into which it is to be introduced. Thus, the vector may be an autonomously replicating vector, i.e. a vector which exists as an extra-chromosomal entity, the replication of which is independent of chromosomal replication, such as a plasmid. Alternatively, the vector may be one which, when introduced into a host cell, is integrated into the host cell genome and replicates together with the chromosome(s) into which it has been integrated.

Preferably, when a polynucleotide of the invention is in a vector it is operably linked to a regulatory sequence which is capable of providing for the expression of the coding sequence by the host cell, i.e. the vector is an expression vector. The term "operably linked" refers to a juxtaposition wherein the components described are in a relationship permitting them to function in their intended manner. A regulatory sequence such as a promoter, enhancer or other expression regulation signal "operably linked" to a coding sequence is positioned in such a way that expression of the coding sequence is achieved under conditions compatible with the control sequences.

The vectors may, for example in the case of plasmid, cosmid, virus or phage vectors, be provided with an origin of replication, optionally a promoter for the expression of the polynucleotide and optionally an enhancer and/or a regulator of the promoter. A terminator sequence may be present, as may be a polyadenylation sequence. The vectors may contain one or more selectable marker genes, for example an ampicillin resistance gene in the case of a bacterial plasmid or a neomycin resistance gene for a mammalian vector. Vectors may be used in vitro, for example for the production of RNA or can be used to transfect or transform a host cell.

The DNA sequence encoding the polypeptide is preferably introduced into a suitable host as part of an expression construct in which the DNA sequence is operably linked to expression signals which are capable of directing expression of the DNA sequence in the host cells. For transformation of the suitable host with the expression construct transformation procedures are available which are well known to the skilled person. The expression construct can be used for transformation of the host as part of a vector carrying a selectable marker, or the expression construct is co-transformed as a separate molecule together with the vector carrying a selectable marker. The vectors may contain one or more selectable marker genes.

Preferred selectable markers include but are not limited to those that complement a defect in the host cell or confer resistance to a drug. They include for example versatile marker genes that can be used for transformation of most filamentous fungi and yeasts such as acetamidase genes or cDNAs (the amdS, niaD, facA genes or cDNAs from *A. nidulans, A. oryzae,* or *A. niger*), or genes providing resistance to antibiotics like G418, hygromycin, bleomycin, kanamycin, phleomycin or benomyl resistance (benA). Alternatively, specific selection markers can be used such as auxotrophic markers which require corresponding mutant host strains: e.g. URA3 (from *S. cerevisiae* or analogous genes from other yeasts), pyrG or pyrA (from *A. nidulans* or *A. niger*), argB (from *A. nidulans* or *A. niger*) or trpC. In a preferred embodiment the selection marker is deleted from the transformed host cell after introduction of the expression construct so as to obtain transformed host cells capable of producing the polypeptide which are free of selection marker genes.

Other markers include ATP synthetase subunit 9 (oliC), orotidine-5'-phosphate-decarboxylase (pvrA), the bacterial G418 resistance gene (useful in yeast, but not in filamentous fungi), the ampicillin resistance gene (*E. coli*), the neomycin resistance gene (Bacillus) and the *E. coli* uidA gene, coding for glucuronidase (GUS). Vectors may be used in vitro, for example for the production of RNA or to transfect or transform a host cell.

For most filamentous fungi and yeast, the expression construct is preferably integrated into the genome of the host cell in order to obtain stable transformants. However, for certain yeasts suitable episomal vector systems are also available into which the expression construct can be incorporated for stable and high level expression. Examples thereof include vectors derived from the 2 μm CEN and pKD1 plasmids of *Saccharomyces* and *Kluyveromyces*, respectively, or vectors containing an AMA sequence (e.g. AMA1 from *Aspergillus*). When expression constructs are integrated into host cell genomes, the constructs are either integrated at random loci in the genome, or at predetermined target loci using homologous recombination, in which case the target loci preferably comprise a highly expressed gene. A highly expressed gene is a gene whose mRNA can make up at least 0.01% (w/w) of the total cellular mRNA, for example under induced conditions, or alternatively, a gene whose gene product can make up at least 0.2% (w/w) of the total cellular protein, or, in case of a secreted gene product, can be secreted to a level of at least 0.05 g/l.

An expression construct for a given host cell will usually contain the following elements operably linked to each other in consecutive order from the 5'-end to 3'-end relative to the coding strand of the sequence encoding the polypeptide of the first aspect: (1) a promoter sequence capable of directing transcription of the DNA sequence encoding the polypeptide in the given host cell, (2) preferably, a 5-untranslated region (leader), (3) optionally, a signal sequence capable of directing secretion of the polypeptide from the given host cell into the culture medium, (4) the DNA sequence encoding a mature and preferably active form of the polypeptide, and preferably also (5) a transcription termination region (terminator) capable of terminating transcription downstream of the DNA sequence encoding the polypeptide.

Downstream of the DNA sequence encoding the polypeptide, the expression construct preferably contains a 3' untranslated region containing one or more transcription termination sites, also referred to as a terminator. The origin of the terminator is less critical. The terminator can for example be native to the DNA sequence encoding the polypeptide. However, preferably a yeast terminator is used in yeast host cells and a filamentous fungal terminator is used in filamentous fungal host cells. More preferably, the terminator is endogenous to the host cell in which the DNA sequence encoding the polypeptide is expressed.

Enhanced expression of the polynucleotide encoding the polypeptide of the invention may also be achieved by the selection of heterologous regulatory regions, e.g. promoter, signal sequence and terminator regions, which serve to increase expression and, if desired, secretion levels of the protein of interest from the chosen expression host and/or to provide for the inducible control of the expression of the polypeptide of the invention.

Aside from the promoter native to the gene encoding the polypeptide of the invention, other promoters may be used to direct expression of the polypeptide of the invention. The promoter may be selected for its efficiency in directing the expression of the polypeptide of the invention in the desired expression host.

Promoters/enhancers and other expression regulation signals may be selected to be compatible with the host cell for which the expression vector is designed. For example prokaryotic promoters may be used, in particular those suitable for use in *E. coli* strains. When expression of the polypeptides of the invention is carried out in mammalian cells, mammalian promoters may be used. Tissues-specific promoters, for example hepatocyte cell-specific promoters, may also be used. Viral promoters may also be used, for example the Moloney murine leukaemia virus long terminal repeat (MMLV LTR), the rous sarcoma virus (RSV) LTR promoter, the SV40 promoter, the human cytomegalovirus (CMV) IE promoter, herpes simplex virus promoters or adenovirus promoters.

Suitable yeast promoters include the *S. cerevisiae* GAL4 and ADH promoters and the *S. pombe* nmt1 and adh promoter. Mammalian promoters include the metallothionein promoter which can be induced in response to heavy metals such as cadmium. Viral promoters such as the SV40 large T antigen promoter or adenovirus promoters may also be used. All these promoters are readily available in the art.

Mammalian promoters, such as β-actin promoters, may be used. Tissue-specific promoters, in particular endothelial or neuronal cell specific promoters (for example the DDAHI and DDAHII promoters), are especially preferred. Viral promoters may also be used, for example the Moloney murine leukaemia virus long terminal repeat (MMLV LTR), the rous sarcoma virus (RSV) LTR promoter, the SV40 promoter, the human cytomegalovirus (CMV) IE promoter, adenovirus, HSV promoters (such as the HSV IE promoters), or HPV promoters, particularly the HPV upstream regulatory region (URR). Viral promoters are readily available in the art.

A variety of promoters can be used that are capable of directing transcription in the host cells of the invention. Preferably the promoter sequence is derived from a highly expressed gene as previously defined. Examples of preferred highly expressed genes from which promoters are preferably derived and/or which are comprised in preferred predetermined target loci for integration of expression constructs, include but are not limited to genes encoding glycolytic enzymes such as triose-phosphate isomerases (TPI), glyceraldehyde-phosphate dehydrogenases (GAPDH), phosphoglycerate kinases (PGK), pyruvate kinases (PYK), alcohol dehydrogenases (ADH), as well as genes encoding amylases, glucoamylases, proteases, xylanases, cellobiohydrolases, β-galactosidases, alcohol (methanol) oxidases, elongation factors and ribosomal proteins. Specific examples of suitable highly expressed genes include e.g. the LAC4 gene from *Kluyveromyces* sp., the methanol oxidase genes (AOX and MOX) from *Hansenula* and *Pichia*, respectively, the glucoamylase (glaA) genes from *A. niger* and *A. awamori*, the *A. oryzae* TAKA-amylase gene, the *A. nidulans* gpdA gene and the *T. reesei* cellobiohydrolase genes.

Examples of strong constitutive and/or inducible promoters which are preferred for use in fungal expression hosts are those which are obtainable from the fungal genes for xylanase (xlnA), phytase, ATP-synthetase subunit 9 (oliC), triose phosphate isomerase (tpi), alcohol dehydrogenase (AdhA), amylase (amy), amyloglucosidase (AG—from the glaA gene), acetamidase (amdS) and glyceraldehyde-3-phosphate dehydrogenase (gpd) promoters.

Examples of strong yeast promoters which may be used include those obtainable from the genes for alcohol dehydrogenase, lactase, 3-phosphoglycerate kinase and triosephosphate isomerase.

Examples of strong bacterial promoters which may be used include the amylase and SPo2 promoters as well as promoters from extracellular protease genes.

Promoters suitable for plant cells which may be used include napaline synthase (nos), octopine synthase (ocs), mannopine synthase (mas), ribulose small subunit (rubisco ssu), histone, rice actin, phaseolin, cauliflower mosaic virus (CMV) 35S and 19S and circovirus promoters.

The vector may further include sequences flanking the polynucleotide giving rise to RNA which comprise sequences homologous to ones from eukaryotic genomic sequences, preferably mammalian genomic sequences, or viral genomic sequences. This will allow the introduction of the polynucleotides of the invention into the genome of eukaryotic cells or viruses by homologous recombination. In particular, a plasmid vector comprising the expression cassette flanked by viral sequences can be used to prepare a viral vector suitable for delivering the polynucleotides of the invention to a mammalian cell. Other examples of suitable viral vectors include herpes simplex viral vectors and retroviruses, including lentiviruses, adenoviruses, adeno-associated viruses and HPV viruses (such as HPV-16 or HPV-18). Gene transfer techniques using these viruses are known to those skilled in the art. Retrovirus vectors for example may be used to stably Integrate the polynucleotide giving rise to the antisense RNA Into the host genome. Replication-defective adenovirus vectors by contrast remain episomal and therefore allow transient expression.

The vector may contain a polynucleotide of the invention oriented in an antisense direction to provide for the production of antisense RNA. This may be used to reduce, if desirable, the levels of expression of the polypeptide.

Host Cells and Expression

In a further aspect the invention provides a process for preparing a polypeptide of the invention which comprises cultivating a host cell transformed or transfected with an expression vector as described above under conditions suitable for expression by the vector of a coding sequence encoding the polypeptide, and recovering the expressed polypeptide. Polynucleotides of the invention can be incorporated into a recombinant replicable vector, such as an expression vector. The vector may be used to replicate the nucleic acid in a compatible host cell. Thus in a further embodiment, the invention provides a method of making a polynucleotide of the invention by introducing a polynucleotide of the invention into a replicable vector, introducing the vector into a compatible host cell, and growing the host cell under conditions which bring about the replication of the vector. The vector may be recovered from the host cell.

Suitable host cells include bacteria such as *E. coli*, yeast, mammalian cell lines and other eukaryotic cell lines, for example insect cells such as Sf9 cells and (e.g. filamentous) fungal cells.

Preferably the polypeptide is produced as a secreted protein in which case the DNA sequence encoding a mature form of the polypeptide in the expression construct is operably linked to a DNA sequence encoding a signal sequence. In the case where the gene encoding the secreted protein has in the wild type strain a signal sequence preferably the signal sequence used will be native (homologous) to the DNA sequence encoding the polypeptide. Alternatively the signal sequence is foreign (heterologous) to the DNA sequence encoding the polypeptide, in which case the signal sequence is preferably endogenous to the host cell in which the DNA sequence is expressed. Examples of suitable signal sequences for yeast host cells are the signal sequences derived from yeast MFα genes. Similarly, a suitable signal sequence for filamentous fungal host cells is e.g. a signal sequence derived from a filamentous fungal amyloglucosidase (AG) gene, e.g. the *A. niger* glaA gene. This signal sequence may be used in combination with the amyloglucosidase (also called (gluco)amylase) promoter itself, as well as in combination with other promoters. Hybrid signal sequences may also be used within the context of the present invention.

Preferred heterologous secretion leader sequences are those originating from the fungal amyloglucosidase (AG) gene (glaA—both 18 and 24 amino acid versions e.g. from *Aspergillus*), the MFα gene (yeasts e.g. *Saccharomyces* and *Kluyveromyces*) or the α-amylase gene (*Bacillus*).

The vectors may be transformed or transfected into a suitable host cell as described above to provide for expression of a polypeptide of the invention. This process may comprise culturing a host cell transformed with an expression vector as described above under conditions suitable for expression of the polypeptide, and optionally recovering the expressed polypeptide.

A further aspect of the invention thus provides host cells transformed or transfected with or comprising a polynucleotide or vector of the invention. Preferably the polynucleotide is carried in a vector which allows the replication and expression of the polynucleotide. The cells will be chosen to be compatible with the said vector and may for example be prokaryotic (for example bacterial), or eukaryotic fungal, yeast or plant cells.

The invention encompasses processes for the production of a polypeptide of the invention by means of recombinant expression of a DNA sequence encoding the polypeptide. For this purpose the DNA sequence of the invention can be used for gene amplification and/or exchange of expression signals, such as promoters, secretion signal sequences, in order to allow economic production of the polypeptide in a suitable homologous or heterologous host cell. A homologous host cell is herein defined as a host cell which is of the same species or which is a variant within the same species as the species from which the DNA sequence is derived.

Suitable host cells are preferably prokaryotic microorganisms such as bacteria, or more preferably eukaryotic organisms, for example fungi, such as yeasts or filamentous fungi, or plant cells. In general, yeast cells are preferred over filamentous fungal cells because they are easier to manipulate. However, some proteins are either poorly secreted from yeasts, or in some cases are not processed properly (e.g. hyperglycosylation in yeast). In these instances, a filamentous fungal host organism should be selected.

Bacteria from the genus *Bacillus* are very suitable as heterologous hosts because of their capability to secrete proteins into the culture medium. Other bacteria suitable as hosts are those from the genera *Streptomyces* and *Pseudomonas*. A preferred yeast host cell for the expression of the DNA sequence encoding the polypeptide is one of the genus *Saccharomyces, Kluyveromyces, Hansenula, Pichia, Yarrowia,* or *Schizosaccharomyces*. More preferably, a yeast host cell is selected from the group consisting of the species *Saccharomyces cerevisiae, Kluyveromyces lactis* (also known as *Kluyveromyces marxianus* var. *lactis*), *Hansenula polymorpha, Pichia pastoris, Yarrowia lipolytica,* and *Schizosaccharomyces pombe*.

Most preferred for the expression of the DNA sequence encoding the polypeptide are, however, filamentous fungal host cells. Preferred filamentous fungal host cells are selected from the group consisting of the genera *Aspergillus, Trichoderma, Fusarium, Disporotrichum, Penicillium, Acremonium, Neurospora, Thermoascus, Myceliophtora, Sporotrichum, Thielavia,* and *Talaromyces*. More preferably a filamentous fungal host cell is of the species *Aspergillus oyzae, Aspergillus sojae* or *Aspergillus nidulans* or is of a species from the *Aspergillus niger* Group (as defined by Raper and Fennell, The Genus *Aspergillus*, The Williams & Wilkins Company, Baltimore, pp 293–344, 1965). These include but are not limited to *Aspergillus niger, Aspergillus awamori, Aspergillus tubigensis, Aspergillus aculeatus, Aspergillus foetidus, Aspergillus nidulans, Aspergillus japonicus, Aspergillus oryzae* and *Aspergillus ficuum*, and also those of the species *Trichoderma reesei, Fusarium graminearum, Penicillium chrysogenum, Acremonium alabamense, Neurospora crassa, Myceliophtora thermophilum, Sporotrichum cellulophilum, Disporotrichum dimorphosporum* and *Thielavia terrestris*.

Examples of preferred expression hosts within the scope of the present invention are fungi such as *Aspergillus* species (in particular those described in EP-A-184,438 and EP-A-284,603) and *Trichoderma* species; bacteria such as *Bacillus* species (in particular those described in EP-A-134,048 and EP-A-253,455), especially *Bacillus subtilis, Bacillus licheniformis, Bacillus amyloliquefaciens, Pseudomonas* species; and yeasts such as *Kluyveromyces* species (in particular those described in EP-A-096,430 such as *Kluyveromyces lactis* and in EP-A-301,670) and *Saccharomyces* species, such as *Saccharomyces cerevisiae*.

Host cells according to the invention include plant cells, and the invention therefore extends to transgenic organisms, such as plants and parts thereof, which contain one or more cells of the invention. The cells may heterologously express the polypeptide of the invention or may heterologously contain one or more of the polynucleotides of the invention. The transgenic (or genetically modified) plant may therefore have inserted (typically stably) into its genome a sequence encoding the polypeptides of the invention. The transformation of plant cells can be performed using known techniques, for example using a Ti or a Ri plasmid from *Agrobacterium tumefaciens*. The plasmid (or vector) may thus contain sequences necessary to infect a plant, and derivatives of the Ti and/or Ri plasmids may be employed.

The host cell may overexpress the polypeptide, and techniques for engineering overexpression are well known and can be used in the present invention. The host may thus have two or more copies of the polynucleotide.

Alternatively, direct infection of a part of a plant, such as a leaf, root or stem can be effected. In this technique the plant to be infected can be wounded, for example by cutting the plant with a razor, puncturing the plant with a needle or rubbing the plant with an abrasive. The wound is then innoculated with the Agrobacterium. The plant or plant part can then be grown on a suitable culture medium and allowed to develop into a mature plant. Regeneration of transformed cells into genetically modified plants can be achieved by using known techniques, for example by selecting transformed shoots using an antibiotic and by sub-culturing the shoots on a medium containing the appropriate nutrients, plant hormones and the like.

Culture of Host Cells and Recombinant Production

The invention also includes cells that have been modified to express the aminopeptidase or a variant thereof. Such cells include transient, or preferably stably modified higher eukaryotic cell lines, such as mammalian cells or insect cells, lower eukaryotic cells, such as yeast and filamentous fungal cells or prokaryotic cells such as bacterial cells.

It is also possible for the polypeptides of the invention to be transiently expressed in a cell line or on a membrane, such as for example in a baculovirus expression system. Such systems, which are adapted to express the proteins according to the invention, are also included within the scope of the present invention.

According to the present invention, the production of the polypeptide of the invention can be effected by the culturing of microbial expression hosts, which have been transformed with one or more polynucleotides of the present invention, in a conventional nutrient fermentation medium.

The recombinant host cells according to the invention may be cultured using procedures known in the art. For each combination of a promoter and a host cell, culture conditions are available which are conducive to the expression the DNA sequence encoding the polypeptide. After reaching the desired cell density or titre of the polypeptide the culturing is ceased and the polypeptide is recovered using known procedures.

The fermentation medium can comprise a known culture medium containing a carbon source (e.g. glucose, maltose, molasses, etc.), a nitrogen source (e.g. ammonium sulphate, ammonium nitrate, ammonium chloride, etc.), an organic nitrogen source (e.g. yeast extract, malt extract, peptone, etc.) and inorganic nutrient sources (e.g. phosphate, magnesium, potassium, zinc, iron, etc.). Optionally, an inducer (dependent on the expression construct used) may be included or subsequently be added.

The selection of the appropriate medium may be based on the choice of expression host and/or based on the regulatory requirements of the expression construct. Suitable media are well-known to those skilled in the art. The medium may, if desired, contain additional components favoring the transformed expression hosts over other potentially contaminating microorganisms.

The fermentation may be performed over a period of from 0.5–30 days. Fermentation may be a batch, continuous or fed-batch process, at a suitable temperature in the range of between 0° C. and 45° C. and, for example, at a pH from 2 to 10. Preferred fermentation conditions include a temperature in the range of between 20° C. and 37° C. and/or a pH between 3 and 9. The appropriate conditions are usually selected based on the choice of the expression host and the protein to be expressed.

After fermentation, if necessary, the cells can be removed from the fermentation broth by means of centrifugation or filtration. After fermentation has stopped or after removal of the cells, the polypeptide of the invention may then be recovered and, if desired, purified and isolated by conventional means. The aminopeptidase of the invention can be purified from fungal mycelium or from the culture broth into which the aminopeptidase is released by the cultured fungal cells.

Preliminary attempts to purify the aminopeptidase produced by *Aspergillus niger* strain 1108, (deposited under accession number NRRL 3112 at the Agricultural Research Service Culture Collection, National Center for Agricultural Utilization Research Peoria, Ill., hereinafter referred to as strain "NRRL 3112"), followed by amino acid sequence determination, repeatedly resulted in amino acid sequence data of an amyloglucosidase, apparently forming a major contamination of the original fermentation sample. Therefore, highly rigorous purification and concentration procedures were required to isolate the aminopeptidase. Only amyloglucosidase amino acid sequence data were obtained during numerous initial attempts to isolate the aminopeptidase over a 1.5 year period. The extreme difficulty encountered in isolating the aminopeptidase produced by *A. niger* NRRL 3112 is due to the fact that aminopeptidase is a very minor part of the total protein secreted by these cells (about 0.01 wt % of the protein found in the supernatant). Furthermore it was found that this enzyme is in fact an intracellular enzyme which is present in culture medium in very small amounts. Even when an amino acid sequence of the aminopeptidase was successfully obtained, false positive sequences were also detected. After a series of arduous isolation procedures, amyloglucosidase of *A. niger* was found to be present in the supernatant of a fermentation culture of *A. niger* NRRL 3112. The contaminating enzyme was detected in at least two forms, proteins of 55 kD and 68 kD, both of which are near the molecular weight of known fungal aminopeptidase. Separation of the contaminating 68 kD protein using anion exchange chromatography was very difficult, and required special conditions to isolate the aminopeptidase, discussed below. Thus, only after numerous difficult and unsuccessful attempts was the polypeptide of the invention finally isolated from *A. niger* NRRL 3112 culture broth for sequencing and characterization.

In another embodiment of the present invention the isolated polypeptide of the invention may be further characterised by at least one of the following physicochemical properties:

(1) an optimal phenylalanine aminopeptidase activity at a pH ranging from 2 to 10, such as from 5 to 8, preferably from 5.5 to 7.5, optimally from 6 to 7;

(2) an optimal phenylalanine aminopeptidase activity at a temperature ranging from 35° C. to 70° C.;

(3) a molecular weight (when deglycosylated) of approximately 72 kDa; and (4) an isoelectric point of about 5.56.

In a preferred embodiment the polypeptide is obtained from a fungus, more preferably from an *Aspergillus*, most preferably from *Aspergillus niger*.

Modifications

Polypeptides of the invention may be chemically modified, e.g. post-translationally modified. For example, they may be glycosylated (one or more times) or comprise modified amino acid residues. They may also be modified by the addition of histidine residues to assist their purification or by the addition of a signal sequence to promote secretion from the cell. The polypeptide may have amino- or carboxyl-terminal extensions, such as an amino-terminal methionine residue, a small linker peptide of up to about 20–25 residues, or a small extension that facilitates purification, such as a poly-histidine tract, an antigenic epitope or a binding domain.

A polypeptide of the invention may be labelled with a revealing label. The revealing label may be any suitable label which allows the polypeptide to be detected. Suitable labels include radioisotopes, e.g. $^{125}$I, $^{35}$S, enzymes, antibodies, polynucleotides and linkers such as biotin.

The polypeptides may be modified to include non-naturally occurring amino acids or to increase the stability of the polypeptide. When the proteins or peptides are produced by synthetic means, such amino acids may be introduced during production. The proteins or peptides may also be modified following either synthetic or recombinant production.

The polypeptides of the invention may also be produced using D-amino acids. In such cases the amino acids will be linked in reverse sequence in the C to N orientation. This is conventional in the art for producing such proteins or peptides.

A number of side chain modifications are known in the art and may be made to the side chains of the proteins or peptides of the present invention. Such modifications include, for example, modifications of amino acids by reductive alkylation by reaction with an aldehyde followed by reduction with NaBH$_4$, amidination with methylacetimidate or acylation with acetic anhydride.

The sequences provided by the present invention may also be used as starting materials for the construction of "second generation" enzymes. "Second generation" peptidases are peptidases, altered by mutagenesis techniques (e.g. site-directed mutagenesis), which have properties that differ from those of wild-type peptidases or recombinant peptidases such as those produced by the present invention. For example, their temperature or pH optimum, specific activity, substrate affinity or thermostability may be altered so as to be better suited for use in a particular process.

Amino acids essential to the activity of the peptidases of the invention, and therefore preferably subject to substitution, may be identified according to procedures known in the art, such as site-directed mutagenesis or alanine-scanning mutagenesis. In the latter technique mutations are introduced at every residue in the molecule, and the resultant mutant molecules are tested for biological activity (e.g. aminopeptidase activity) to identify amino acid residues that are critical to the activity of the molecule. Sites of enzyme-substrate interaction can also be determined by analysis of crystal structure as determined by such techniques as nuclear magnetic resonance, crystallography or photo-affinity labelling.

The use of yeast and filamentous fungal host cells is expected to provide for such post-translational modifications (e.g. proteolytic processing, myristilation, glycosylation, truncation, and tyrosine, serine or threonine phosphorylation) as may be needed to confer optimal biological activity on recombinant expression products of the invention.

Preparations

Polypeptides of the invention may be in an isolated form. It will be understood that the polypeptide may be mixed with carriers or diluents which will not interfere with the intended purpose of the polypeptide and still be regarded as isolated. A polypeptide of the invention may also be in a substantially purified form, in which case it will generally comprise the polypeptide in a preparation in which more than 70%, e.g. more than 80%, 90%, 95%, 98% or 99% of the proteins in the preparation is a polypeptide of the invention.

Polypeptides of the invention may be provided in a form such that they are outside their natural cellular environment. Thus, they may be substantially isolated or purified, as discussed above, or in a cell in which they do not occur in nature, for example a cell of other fungal species, animals, plants or bacteria.

Removal or reduction of aminopeptidase activity

The present invention also relates to methods for producing a mutant cell of a parent cell, which comprises disrupting or deleting the endogenous nucleic acid sequence encoding the polypeptide or a control sequence thereof, which results in the mutant cell producing less of the polypeptide than the parent cell.

The construction of strains which have reduced aminopeptidase activity may be conveniently accomplished by modification or inactivation of a nucleic acid sequence necessary for expression of the aminopeptidase in the cell. The nucleic acid sequence to be modified or inactivated may be, for example, a nucleic acid sequence encoding the polypeptide or a part thereof essential for exhibiting aminopeptidase activity, or the nucleic acid sequence may have a regulatory function required for the expression of the polypeptide from the coding sequence of the nucleic acid sequence. An example of such a regulatory or control sequence may be a promoter sequence or a functional part thereof, i.e., a part which is sufficient for affecting expression of the polypeptide. Other control sequences for possible modification include, but are not limited to, a leader sequence, a polyadenylation sequence, a propeptide sequence, a signal sequence, and a termination sequence.

Modification or inactivation of the nucleic acid sequence may be performed by subjecting the cell to mutagenesis and selecting cells in which the aminopeptidase producing capability has been reduced or eliminated. The mutagenesis, which may be specific or random, may be performed, for example, by use of a suitable physical or chemical mutagenizing agent, by use of a suitable oligonucleotide, or by subjecting the DNA sequence to PCR mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the cell to be mutagenized in the presence of the mutagenizing agent of choice under suitable conditions, and selecting for cells exhibiting reduced or no expression of aminopeptidase activity.

Modification or inactivation of production of a polypeptide of the present invention may be accomplished by introduction, substitution, or removal of one or more nucleotides in the nucleic acid sequence encoding the polypeptide or a regulatory element required for the transcription or translation thereof. For example, nucleotides may be inserted or removed so as to result in the introduction of a stop codon, the removal of the start codon, or a change of the open reading frame. Such modification or inactivation may be accomplished by site-directed mutagenesis or PCR mutagenesis in accordance with methods known in the art.

Although, in principle, the modification may be performed in vivo, i.e., directly on the cell expressing the nucleic acid sequence to be modified, it is preferred that the modification be performed in vitro as exemplified below.

An example of a convenient way to inactivate or reduce production of the aminopeptidase by a host cell of choice is based on techniques of gene replacement or gene interruption. For example, in the gene interruption method, a nucleic acid sequence corresponding to the endogenous gene or gene fragment of interest is mutagenized in vitro to produce a defective nucleic acid sequence which is then transformed into the host cell to produce a defective gene. By homologous recombination, the defective nucleic acid sequence replaces the endogenous gene or gene fragment. Preferably the defective gene or gene fragment also encodes a marker which may be used to select for transformants in which the gene encoding the polypeptide has been modified or destroyed.

Alternatively, modification or inactivation of the nucleic acid sequence encoding a polypeptide of the present invention may be achieved by established anti-sense techniques using a nucleotide sequence complementary to the polypeptide encoding sequence. More specifically, production of the polypeptide by a cell may be reduced or eliminated by introducing a nucleotide sequence complementary to the nucleic acid sequence encoding the polypeptide. The anti-sense polynucleotide will then typically be transcribed in the cell and will be capable of hybridizing to the mRNA encoding the aminopeptidase. Under conditions allowing the complementary antisense nucleotide sequence to hybridize to the mRNA, the amount of the aminopeptidase produced in the cell will be reduced or eliminated.

It is preferred that the cell to be modified in accordance with the methods of the present invention is of microbial origin, for example, a fungal strain which is suitable for the production of desired protein products, either homologous or heterologous to the cell.

The present invention further relates to a mutant cell of a parent cell which comprises a disruption or deletion of the endogenous nucleic acid sequence encoding the polypeptide or a control sequence thereof, which results in the mutant cell producing less of the polypeptide than the parent cell.

The polypeptide-deficient mutant cells so created are particularly useful as host cells for the expression of homologous and/or heterologous polypeptides. Therefore, the present invention further relates to methods for producing a homologous or heterologous polypeptide comprising (a) culturing the mutant cell under conditions conducive for production of the polypeptide; and (b) recovering the polypeptide. In the present context, the term "heterologous polypeptides" is defined herein as polypeptides which are not native to the host cell, a native protein in which modifications have been made to alter the native sequence, or a native protein whose expression is quantitatively altered as a result of a manipulation of the host cell by recombinant DNA techniques.

In a still further aspect, the present invention provides a method for producing a protein product essentially free of aminopeptidase activity by fermentation of a cell which produces both an aminopeptidase polypeptide of the present invention as well as the protein product of interest. The method comprises adding an effective amount of an agent capable of inhibiting aminopeptidase activity to the fermentation broth either during or after the fermentation has been completed, recovering the product of interest from the fermentation broth, and optionally subjecting the recovered product to further purification. Alternatively, after cultivation the resultant culture broth can be subjected to a pH or temperature treatment so as to reduce the aminopeptidase activity substantially, and allow recovery of the product from the culture broth. The combined pH or temperature treatment may be performed on an protein preparation recovered from the culture broth.

The methods of the present invention for producing an essentially aminopeptidase-free product is of particular interest in the production of eukaryotic polypeptides, in particular in the production of fungal proteins such as enzymes. The aminopeptidase-deficient cells may also be used to express heterologous proteins of interest for the food industry, or of pharmaceutical interest.

Applications

Food proteins in their native molecular size have little interaction with taste receptors and confer little taste. However, the degradation products of food proteins, such as peptides and amino acids released by hydrolysis, exhibit distinct tastes such as sweet, sour and bitter. The removal of single or pairs of hydrophobic amino acids from the terminal ends of a peptide chain can reduce undesirable tastes associated with many protein hydrolysates. For example, leucine aminopeptidases cleave leucine as well as certain other amino acids from peptide chains. Also known are valine and phenylalanine aminopeptidases. Often, endoproteases which break down intact proteins are used in conjunction with certain peptidases to improve food flavor. The aminopeptidase of the invention has a strong specificity toward phenylalanine, and is advantageous in this regard for enhancing phenylalanine-related aromas in foodstuffs.

Enzymatic digests of flavor-enhancing peptides can be added to foods during their production. Thus, an aminopeptidase of the invention, either alone or in combination with a protease, may be used to produce a protein hydrolysate having, inter alia. After fermentation or Maillard reactions of this protein hydrolysate the thus obtained product can be used for example in flavouring compositions. Such hydrolysates may be prepared in a one-step fashion in which the substrate and all of the required enzymes are mixed concurrently. Alternatively, individual flavor components of a complex hydrolysate may be created separately and then blended together in a particular ratio to form the hydrolysate flavorant. For example, the fungal aminopeptidase of the invention may be used in the degradation of casein to form a cheese flavored hydrolysate for use in cheese flavored products, such as sauces, crackers, spreads, snacks, and the like. Enzymatic cleavage of certain proteins can create meat-flavored hydrolysates as well. Soy proteins are commonly used for this purpose, although they typically cannot be enzymatically hydrolyzed to the same degree as can be accomplished with acid hydrolysis. The fungal aminopeptidase of the invention may be used in combination with enzymes capable of degrading the carbohydrate portion of a substrate to form Maillard products that contribute to the meaty flavor of the hydrolysate. Such meat-flavored hydrolysates may be used the enhance the flavor of soups, gravies, prepared foods, snacks and the like.

An aminopeptidase of the invention may be used in situ to improve the flavor of various foods, including baked products and cheeses. For example, from 1 to 100 units of phenylalanine aminopeptidase may be added per kilogram of bread dough to improve the flavor and aroma of the final baked product. Preferably, from 5 to 50 units of aminopeptidase are used. The added aminopeptidase modifies the soluble proteins of flour, such as wheat gluten, by attacking preferred bond pairs such that small peptides and amino acids are released.

Similarly, from 5 to 500 units of phenylalanine-aminopeptidase, preferably from 15 to 250 units, may be added per 1000 liters of milk to improve the taste, flavor, aroma, texture and consistency of cheese, thereby accelerating ripening. Such in situ improvements are due to the liberation of free amino acids by the aminopeptidase from proteins, such as caseins, within the cheese milk. A major benefit of aminopeptidase treatment of cheese milk is accelerated ripening of cheese without the risk of overripening. Aminopeptidases may be combined with chymosin, neutral protease, and dairy starter cultures to reduce the effects of fluctuating milk quality, such as the production of bitter tastes, thereby improving the flavor of ripened cheese. For instance, the aminopeptidase of the invention may be used in this regard to enhance the fruity note of camembert cheeses during ripening. The use of aminopeptidases in cheese production is further discussed in WO 96/38549.

The isolated aminopeptidase of the invention has a very strong preference for cleaving phenylalanine from peptide chains, as evidenced in FIG. 13. This exceptional strength, which is not characteristic of, for example, previously known crude fungal filtrates, may be utilized in applications targeting phenylalanine. Thus, the isolated enzyme of the invention is useful in the preparation of protein hydrolysates having low phenylalanine concentrations. Protein hydrolysates treated with an endoprotease and the isolated phenylalanine aminopeptidase of the invention may be processed in a fashion, such as with charcoal, so as to specifically remove small hydrophobic compounds containing phenylalanine. Such low phenylalanine hydrolysates produced according to the invention may be utilized in compositions safe for consumption by phenylketonurics, who lack sufficient phenylalanine hydroxylase to convert phenylalanine to tyrosine.

The invention is further illustrated by the following non-limiting examples.

EXAMPLE 1

Isolation Procedure of Aminopeptidase

Materials & Methods for Example 1:

Activity Assays

Aminopeptidase activity was determined by spectrophotometrically following the splitting of L-phenylalanine p-nitroanilide at 400 nm. Activity was measured at 0.3 mM substrate concentration in 0.1 M NaPi buffer at pH 7.2 and 25° C.

Amyloglucosidase activity was determined by spectrophotometric measurement of p-nitrophenol, formed by the hydrolysis of p-nitrophenyl α-D-glucopyranoside by the action of amyloglucosidase. The assay solution contained the substrate of a concentration of 0.5 mM in 0.1 M sodium acetate buffer, pH 4.4. After incubation for 15 minutes at 25° C. the reaction was stopped with 5 volumes of a 0.25 M sodium carbonate solution. Sample adsorbance was measured at 402 nm.

Zymogram Procedure

To locate aminopeptidase activity on a native PAGE gel, immediately after being run the gel was overlayed with a thin layer of 7.5 mM HCl solution containing 0.9 mM L-phenylalanine p-nitroanilide. A yellow spot formed at the location of the aminopeptidase in the gel. The yellow spot was read immediately after the L-phenylalanine p-nitroanilide solution was poured over the gel, since the yellow spot quickly diffused from its initial location.

Analytical Native PAGE

Native PAGE was performed using the Phastsystem™ (Pharmacia) and Homogeneous 20% Phastgels. Gels were run and the proteins thus separated were stained with Coomassie Brilliant Blue following the manufacturer's instructions.

Desalting on PD10

Protein samples were desalted or transferred to another buffer using Pharmacia's™ PD10 columns according to the instructions of the manufacturer.

Ultrafiltration

Ultrafiltration was performed using a Filtron™ Microsep centrifugal device with an Omega-10 kD modified polyethersulfone membrane (Filtron™ Techn. Corp. Northborough Mass., USA). Samples were centrifuged at maximal 7500×g with a fixed-angle rotor.

Mono Q Chromatography

Chromatography was carried out on a Pharmacia™ FPLC system (2 * P-500 pumps, a LKB-2141 UV monitor at 280/260 nm and a Frac-200 fraction collector). A Pharmacia™ Mono Q HR 5/5 column was used at a flow rate of 1 ml/min. The column was equilibrated with 20 mM Tris/HCl pH 7.5 (buffer A). After sample application, the column was washed with five bed volumes of buffer A. Aminopeptidase activity was eluted using a linear 0–250 mM NaCl gradient in 25 bed volumes of buffer A.

Preparative Electrophoresis

The preparative electrophoresis was performed using the Biorad™ Protean II cell with a 15% polyacrylamide separation gel and 5% polyacrylamide stacking gel.

The separation gel was made by mixing 20 ml 30% (w/v) acrylamide/0.8% (w/v) N,N-methylenebisacrylamide, 20 ml 9% (w/v) Tris.HCl (pH 8.8), 200 µl 10% (w/v) ammonium persulfate and 20 µl N,N,N',N'-tetramethyleneethylenediamine (TEMED). The stacking gel was made by mixing 2.22 ml 30% (w/v) acrylamide/0.8% (w/v) N,N'-methylenebisacryl-amide, 6.67 ml 3% (w/v) Tris.HCl pH 6.8, 4.4 ml Milli Q, 100 µl 10% (w/v) ammonium persulfate and 10 µl TEMED. The composition of the electrophoresis buffer was 1.0 g Tris and 4.8 g glycine per liter. Samples were mixed with ¼ volume sample buffer (6% (w/v) Tris.HCl (pH 6.8), 50% (v/v) glycerol, 0.01 (w/v) bromophenol blue). The sample was applied on the preparative gel with 20 wells (20 µl per well). Electrophoresis was performed at 200 V and 60 mA. Destaining procedures were performed according to published Pharmacia™ instructions.

Description of the Experiments:

Successful purification of an aminopeptidase from the supernatant of *A. niger* NRRL 3112 was accomplished as follows:

*A. niger* NRRL 3112 was grown in a medium containing 15 g/l potato flour, 20 g/l bactopeptone, 7 g/l yeast extract, 4 g/l potassium dihydrogenphosphate, 0.5 g/l magnesium sulfate, 0.5 g/l calcium chloride, 0.5 g/l zinc chloride, pH was 4.8. After 24 hours preculture in an incubator at 240 rpm and 30° C., and 96 hours culture at 275 rpm 30° C., supernatant was collected.

Figure 1:
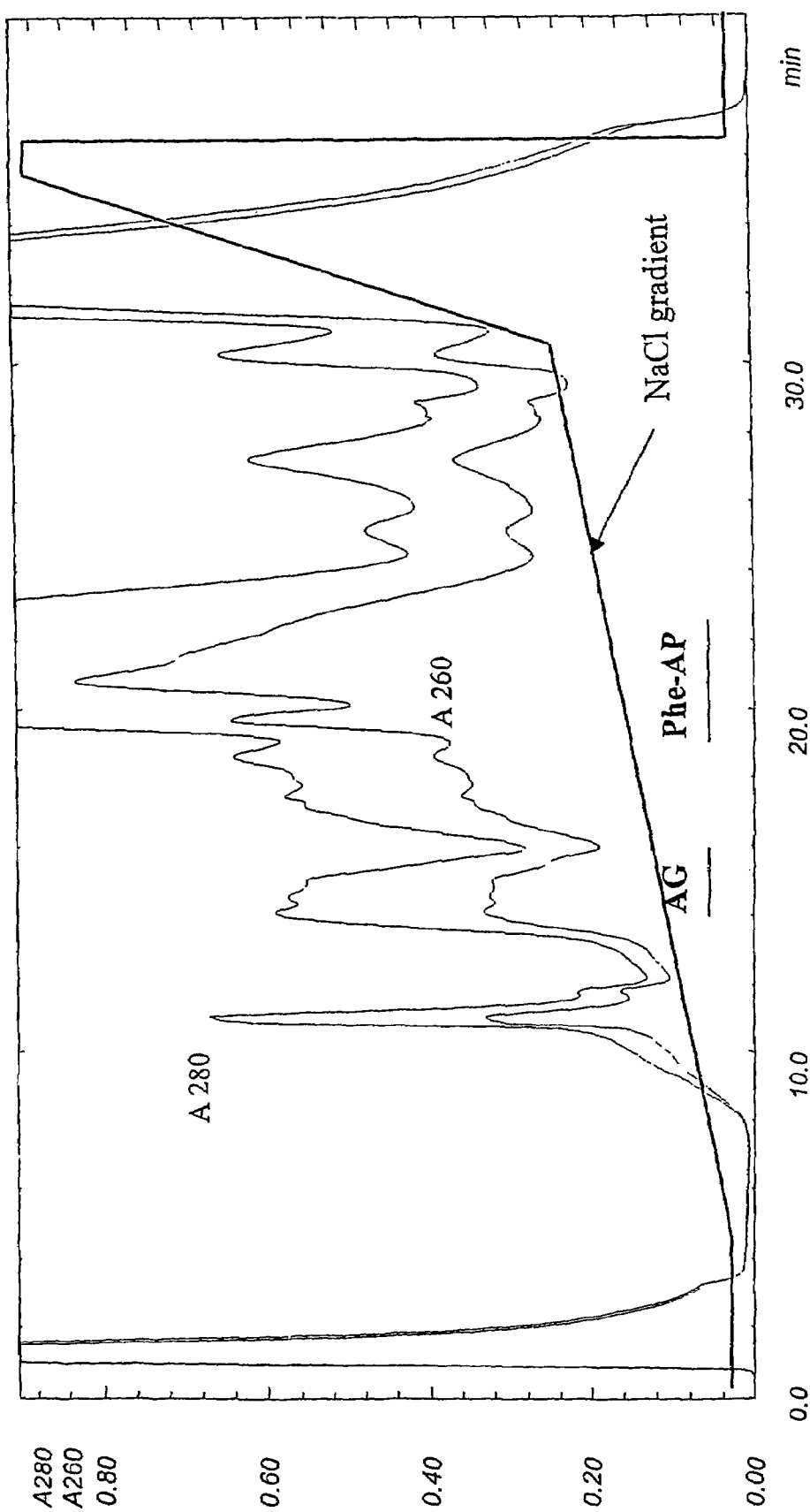
FIG. 1 shows an FPLC chromatogram of a fermentation sample, indicating separate fractions having aminoglucosidase (AG) and aminopeptidase (AP) activities.

The supernatant containing the polypeptide with aminopeptidase activity was transferred to a 10 mM Tris pH 7.5 buffer over a PD10 column. The still crude PD10 eluate (500 µl) was fractionated by anion exchange chromatography on Mono Q to separate the aminopeptidase activity from the amyloglucosidase activity. Aminopeptidase and amyloglucosidase containing fractions (1 ml each) were identified using the activity assays described above. Amyloglucosidase and aminopeptidase activity eluted at 100 and 160 mM NaCl respectively, as shown in the chromatogram of FIG. 1.

The aminopeptidase activity-containing peak fractions (three fractions of 1 ml each) were pooled and concentrated by ultrafiltration. The concentration factor was approximately 6, resulting in concentrate A.

Figure 2:
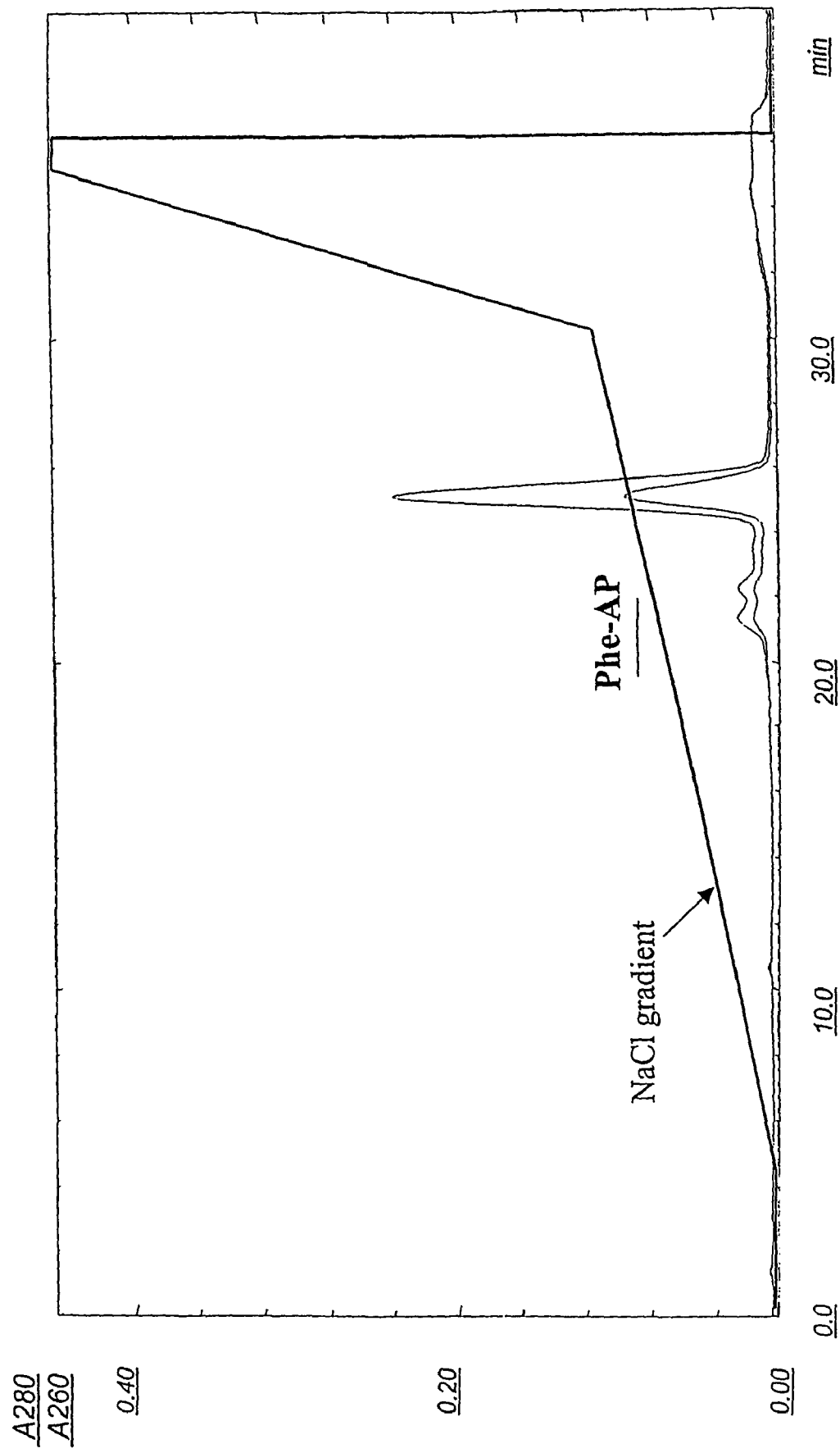
FIG. 2 shows an FPLC chromatogram of concentrate A on an anion exchange column.

A 500 µl sample of concentrate A, diluted 1:12 was analyzed on a Mono QTM column (Pharmacia™). From the chromatogram shown in FIG. 2, a very small peak is detectable around 160 mM NaCl. However, the bulk of the protein elutes at much higher NaCl concentration. No protein can be seen at 100 mM NaCl, the location of the amyloglucosidase (AG) peak.

The above-mentioned purification procedure (Mono Q (resulting in peak fractions of three fractions of 1 ml each), pooled and concentrated by ultrafiltration) was applied to the rest of the PD 10 eluate, and all concentrates A so obtained were pooled in order to obtain sufficient material for further purification. This pool of concentrates A was further concentrated by ultrafiltration, then desalted over a PD10 column and simultaneously transferred to 10 mM Tris pH 7.5 buffer resulting in concentrate B (approx. 3.5 ml).

Concentrate B and the original supernatant of the fermentation were subjected to analytical native PAGE and zymogram procedures for evaluation of the aminopeptidase and amyloglucosidase activity.

Figure 3:
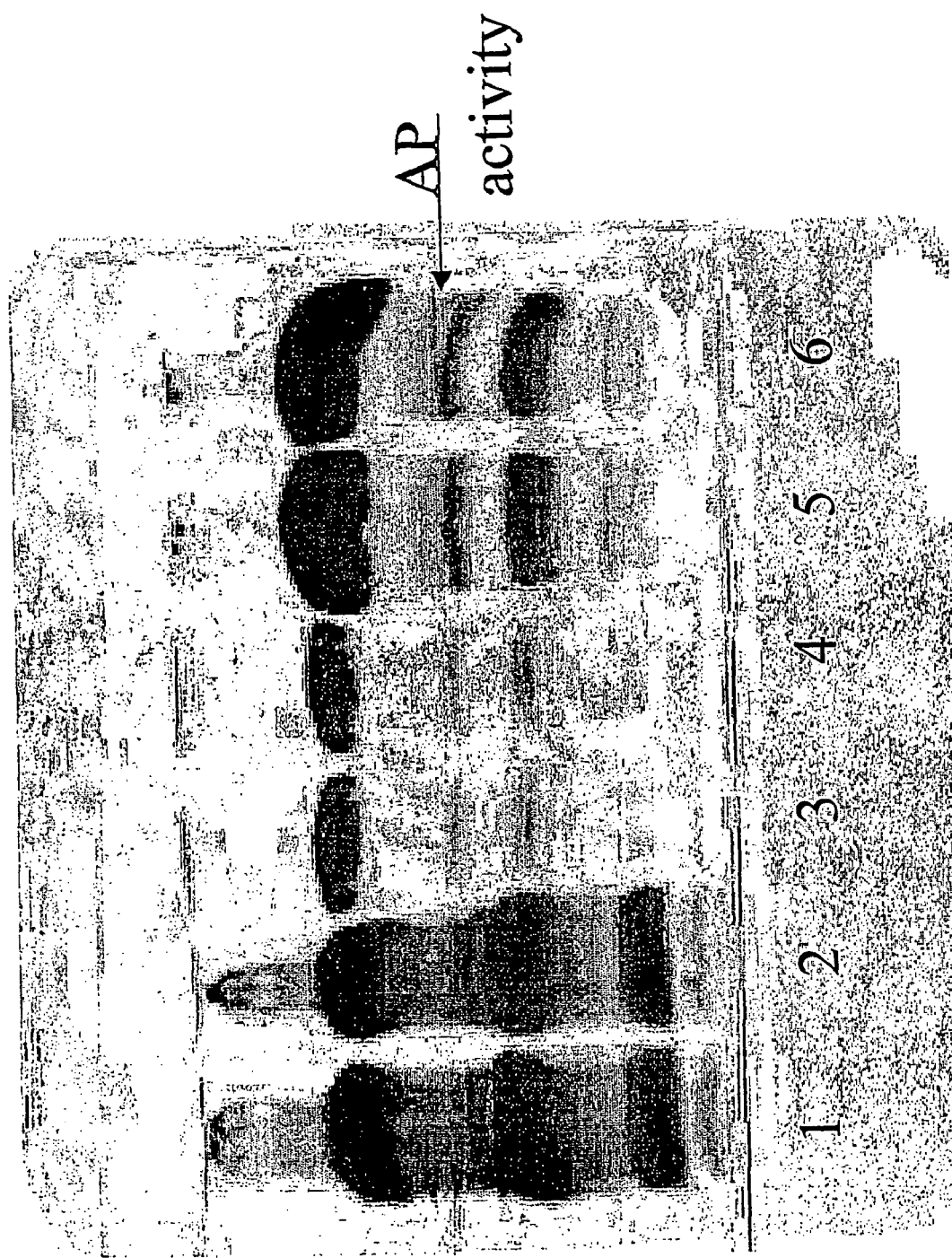
FIG. 3 shows native PAGE analysis of fermentation sample (lane 1–2) and concentrate B (lane 3–40) and 4× concentrated B (lane 5–6)

The native PAGE analysis depicted in FIG. 3 shows that ion exchange chromatography partially purified the crude fermentation supernatant, indicated by the presence of different sample protein compositions before and after Mono Q chromatography. The arrow indicates the location where the aminopeptidase was detected on the gel by making use of zymography. No clear band of a single protein at the site aminopeptidase activity was visually detectable.

Clearly, even after purification, the aminopeptidase is still a very minor part of the total protein present in the fermentation broth. Concentrate B comprised only about 1% (based on total protein) of what was later found to be the aminopeptidase, whereas the supernatant of the fermentation contained about 0.01% of the aminopeptidase.

The fermentation sample from which the purification was started contained 369 units aminopeptidase and 62 units amyloglucosidase per ml, while concentrate B showed an activity of 158 U/ml aminopeptidase and 1.2 U/ml amyloglucosidase, which resulted in a relative activity enrichment factor of 22 (158/369:1.2/62) of aminopeptidase over amyloglucosidase.

The remaining part of concentrate B was further concentrated 5 times by ultrafiltration. The ultrafiltrate was mixed with sample buffer. 400 µl mixture was applied to a preparative gel with 20 lanes (20 µl/lane) and subjected to electrophoresis for 5½ hours. Two lanes were used for a zymogram from which it appeared that aminopeptidase activity had migrated about 16–18 mm into the separation gel. After staining the remaining untreated lanes, a band located at about 16-18 mm from the front was cut from the gel and subjected to standard internal amino acid sequencing procedures performed at Eurosequence (Groningen, The Netherlands) as described in Rosenfeld et al, 1992, Anal Biochem 203, 173–179. The result was an *A. niger* NRRL 3112 aminopeptidase, partially encoded by the nucleotide sequence of SEQ ID NO: 3 (FIG. 4). Various peptide fragments of the aminopeptidase of *A. niger* NRRL 3112 are shown in Table 1, wherein peptide fragment 1 corresponds to amino acids 188–194 of SEQ ID NO: 2; and peptide fragment 2 corresponds to amino acids 235–247 of SEQ ID NO: 2, exemplifying the sequence identity that was eventually found between the aminopeptidases of *A. niger* strains NRRL 3112 and N400. NRRL 3112 peptide fragment 3 differs by only one amino acid from amino acids 5–20 of SEQ ID NO: 2, substituting a proline for alanine at amino acid position 7. Peptide fragment 4 corresponds to SEQ ID NO: 12, and was found to be a contaminant, showing once again the difficulty encountered in obtaining a purified, isolated aminopeptidase from the crude culture broth.

TABLE 1

N-terminal peptide sequences of various ApS C peptide fragments of the
A. niger NRRL 3112 strain and DNA sequences of degenerate primers from
the N-terminal peptide sequences, standard IUPAC codes are used.

| No. | Peptide sequence | Forward primer | Reverse primer |
|---|---|---|---|
| 1 | V*S*WIQWN (SEQ ID NO:25) | Sap-1 SNTGGATHCARTGGAAY (SEQ ID NO:4) | Sap-2 RTTCCAYTGDATCCA (SEQ ID NO:5) |
| 2 | WGPDGTLFFVSDR (SEQ ID NO:26) | Sap-3 TGGGGNCCNGAYGGNAC (SEQ ID NO:6) | Sap-4 GTNCCRTCNGGNCCCCA (SEQ ID NO:7) |
| 3 | AEPQTAPFGTWDSPIT (SEQ ID NO:27) | Sap-5 GARCCICARACNGCICCNTT (SEQ ID NO:8) Sap-6 GCNCCNTTYGGIACNTGGGA (SEQ ID NO:9) | |
| 4 | (S)RVEYLFENERLPLDL (SEQ ID NO:12) | Sap-7 GARTAYYTITTYGARAAYGA (SEQ ID NO:10) | Sap-8 TCRTTYTCRAAIARRTAYTC (SEQ ID NO:11) |

*indicates that the amino acid was not certain.

EXAMPLE 2

Construction of a Genomic Library of *Aspergillus niger* Strain N400

The construction of the genomic library in the phage lambda replacement vector EMBL4 from Promega Biotech Inc (Madison Wis.) of *Aspergillus niger* strain N400 (accession number CBS 120.49, available at Centraal Bureau voor Schimmelcultures (CBS), The Netherlands) was done as described by Harmsen et al. (1990).

EXAMPLE 3

Screening of the *Aspergillus niger* Strain N400 Genomic Library for the Aminopeptidase C Gene and Isolation of the Gene.

Example 3.1

Isolating a Fragment of the Gene Encoding for a Polypeptide with Aminopeptidase Activity of *A. niger* NRRL 3112 Using PCR with Synthetic Oligonucleotide Mixtures.

Details of molecular cloning techniques are described by Sambrook et al., 1989 Molecular cloning, A laboratory manual 2$^{nd}$ edition, Cold Spring Harbor Laboratory Press, New York.

The amino acid sequences shown in Table 1 were used to synthesize degenerate oligonucleotide primer mixtures. The oligonucleotides were synthesized by Isogen Bioscience, Baam, The Netherlands.

Since the order of the obtained peptide fragments in the open reading frame was not known, the primers were designed in both the forward and reverse directions.

PCR reactions were performed using an equal amount of two oligonucleotide mixtures, Taq-polymerase (Life Technologies™, Rockville, Md.) and 10 or 100 ng of genomic DNA of *Aspergillus niger* NRRL 3112 (isolated according to the method of De Graaff et al 1988, Curr. Genet. 13:315–321). The denaturing temperature was 95° C. for one minute, the annealing temperature differed per PCR reaction (see Table 1A) and was one minute and the extension temperature was 72° C. for one minute. 30 cycles were applied followed by a 10 minutes extension at 72° C.

The reaction mixture was subjected to agarose gel electrophoresis using a 0.8% agarose gel and voltage of 4.3 V/cm for 2 hours.

All the primers were tested in combination with primer 5 or 6 because the fragment from which those primers were derived was thought to be an N-terminal sequence (see Table 1). Primer combination sap-5 and sap-4 gave a product of about 750 bp. This product was picked from the gel using a Pasteurs pipette and eluted into sterile H$_2$O by shaking for 3 hours. This H$_2$O containing the approximately 750 bp PCR fragment was used in a new PCR using primer combination sap-6 and sap-4 with an annealing temperature of 54° C. This PCR again resulted in a fragment of approximately 750 bp.

This fragment was isolated from gel using a commercially available DNA purification kit (Gene clean™, Bio101 Inc., La Jolla, USA).

TABLE 1A

| Annealing temperature (° C.) | DNA amount (ng) | Primer combination | Product |
|---|---|---|---|
| 50 | 100 | sap-5; sap-2 | no |
| 50 | 100 | sap-5; sap-4 | a-specific |
| 50 | 100 | sap-5; sap-8 | no |
| 50 | 100 | sap-6; sap-2 | 500 bp 200 bp |
| 50 | 100 | sap-6; sap-4 | a-specific |
| 50 | 100 | sap-6; sap-8 | 500 bp 200 bp |
| 50 | 100 | sap-7; sap-2 | no |
| 50 | 100 | sap-7; sap-4 | a-specific |
| 50 | 100 | sap-8; sap-1 | no |
| 50 | 100 | sap-8; sap-3 | a-specific |
| 52 | 10 | sap-5; sap-2 | no |
| 52 | 10 | sap-5; sap-4 | 750 bp 500 bp 400 bp |
| 52 | 10 | sap-5; sap-8 | no |
| 52 | 10 | sap-7; sap-2 | no |
| 52 | 10 | sap-7; sap-4 | 500 bp 400 bp |
| 52 | 10 | sap-6; sap-2 | no |
| 52 | 10 | sap-6; sap-4 | 750 bp 500 bp 400 bp |
| 52 | 10 | sap-6; sap-8 | no |
| 52 | 10 | sap-8; sap-3 | no |
| 52 | 10 | sap-8; sap-1 | no |
| 52 | 100 | sap-5; sap-2 | a-specific |
| 52 | 100 | sap-5; sap-4 | no |
| 52 | 100 | sap-5; sap-8 | a-specific |
| 52 | 100 | sap-7; sap-2 | no |
| 52 | 100 | sap-7; sap-4 | a-specific |

TABLE 1A-continued

| Annealing temperature (° C.) | DNA amount (ng) | Primer combination | Product |
|---|---|---|---|
| 52 | 100 | sap-6; sap-2 | no |
| 52 | 100 | sap-6; sap-4 | 750 bp |
|  |  |  | 500 bp |
|  |  |  | 400 bp |
| 52 | 100 | sap-6; sap-8 | no |
| 52 | 100 | sap-8; sap-1 | no |
| 52 | 100 | sap-8; sap-3 | no |
| 54 | 100 | sap-4 | a-specific |
| 54 | 100 | sap-5 | no |
| 54 | 100 | sap-6 | no |
| 54 | 100 | sap-6; sap-4 | a-specific |
| 54 | 100 | sap-5; sap-4 | a-specific |
| 54 | 10 | sap-6;sap-4 | 750 bp |
| 54 | 10 | sap-5; sap-4 | 750 bp |
|  |  |  | 500 bp |
|  |  |  | 1300 bp |

Example 3.2

Cloning and Sequencing of the 750 bp Fragment.

The DNA fragment isolated in Example 3.1 was cloned into the commercially available pGEM-T Vector system (Promega Biotech™ Inc. Madison Wis., USA). The ligation mixes wer transferred to *E. coli* DH5α (Life Technologies™, Rockville, Md., USA) and plated out on LB$^{amp}$ plates (LB$^{amp}$ contains 10 g/l NaCl, 10 g/l Tryptone, 5 g/l Yeast Extract and 50 µg/ml Ampicillin, plates were solidified by addition of 1.5% (w/v)agar), with 0.1% (w/v)X-gal (5-bromo-4-chloro-3-indoloyl-β-D-galactopyranoside) and 5 mM IPTG (isopropyl-β-D-thlogalactopyranoside) for selection of transformants containing an insert (Sambrook et al., 1989).

Per ligation, 5 transformants were selected and grown overnight in 3 ml LB$^{amp}$ at 37° C. while shaking at 250 rpm.

Figure 5:
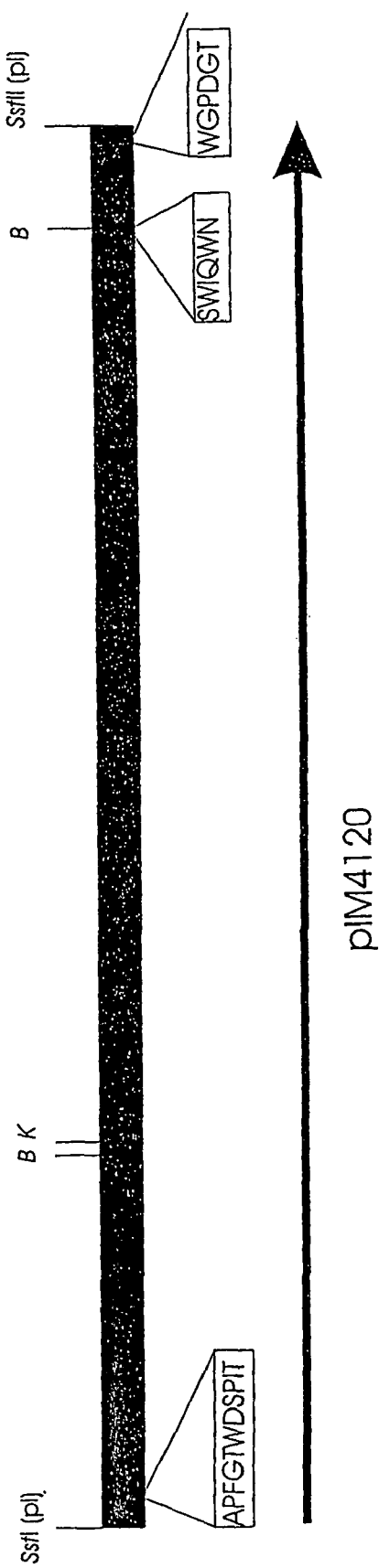
FIG. 5 Shows the restriction map of pIM 4120. The sequenced peptide fragments encountered in the conceptual translate are boxed. SstI(pI): SstI originating from polylinker of pGEM-T, B: BamHI, K: KpnI, SstII(pI): SstII originating from polylinker of pGEM-T. The arrow indicates the open reading frame.

Plasmid DNA was isolated from the cultures by the alkaline lysis method (Sambrook et al., 1989). Plasmid 5, containing the 750 bp fragment was denoted pIM 4120 as depicted in FIG. 5. Sequence analysis of pIM 4120 was performed using the Thermosequenase fluorescent labelled primer cycle sequencing kit (Amersham™ LIFE SCIENCE) and the ALF express (Pharmacia™ Biotech). This resulted in a 751 bp NRRL 3112 nucleic acid sequence, corresponding to bases 241–991 of SEQ ID NO: 3 in which both of the primer sequences SAP-4 and SAP-6 can be detected, as shown in FIG. 4.

Sequences were analyzed with the PC gene software (IntelliGenetics™, Geneva Switzerland)

The complete nucleic acid sequence of this fragment was translated into a putative amino acid sequence. Table 1 shows peptide sequences of various fragments of the aminopeptidase C (ApsC) gene of *Aspergillus niger* NRRL 3112 as well as sequences of degenerate primers derived from those peptide sequences. Peptide 3 and peptide 2 from which primers were designed could be identified at the amino terminal and the carboxy terminal end of the inferred amino acid sequence, respectively (see FIG. 5). A third peptide sequence (peptide 1, Table 1) showed complete identity to an internal region of the inferred amino acid sequence.

Example 3.3

Identification of the Gene Encoding Aminopeptidase in *Aspergillus niger* N400 (CBS120.49).

Using primers on the genomic DNA of *A. niger* NRRL 3112, it is evident that the corresponding aminopeptidase gene can be cloned from strain NRRL 3112. The equivalent gene may also be cloned from *A. niger* strain N400 (CBS 120.49).

Genomic DNA of *A. niger* N400 was isolated according to the method of De Graaff et al. (1988). Southern blot analysis was performed using individual aliquots of 5 µg genomic DNA digested with BamHI, EcoRI, HindIII, SstI, SstII, and SalI respectively. The DNA was digested for 17 h at 37° C. with 30 units of enzyme. After digestion the DNA was precipitated with ethanol and after dissolving the precipitated DNA in 20 µl H$_2$O the digested DNA was separated with gel electrophoresis as described in example 3.1. After separation, the DNA was denatured by standard methods (Sambrook et al. 1989) and transferred to a nitrocellulose membrane (Hybond-N, Amersham™) following the recommendations of the supplier. After crosslinking the DNA to the filters by UV treatment for 2 min., the filters were prehybridized in hybridization buffer (HB), containing 6×SSC (20×SSC contains 3 M NaCl and 0.3 M sodium citrate), 5× Denhardts solution (100× Denhardts solution contains 20 g ficoll 400, 20 g polyvinylpyrrolidone and 20 g bovine serum albumin (fraction V) per L) 0.5% Sodium Dodecyl Sulfate (SDS) and 100 µg/ml heat denatured herring sperm DNA, for three hours.

pIM 4120 was digested with 10 units SstI and 10 units SstII for 2 hours at 37° C. After digestion, the DNA was subjected to gel electrophoresis as described in example 3.1. The approximately 750 bp fragment was isolated from the gel as described in example 3.1 and was purified.

50 ng DNA of the approximately 750 bp fragment of strain NRRL 3112 was labelled with [α-$^{32}$P]-dATP by random priming as described by Feinberg & Vogelstein, (1983). To remove unincorporated [α-$^{32}$P]-ATP, the reaction mixture was fractionated on a Sephadex G25 column equilibrated in TE pH 8 (10 mM Tris-HCl pH 8 and 1 mM EDTA-NaOH pH 8). Fractions containing the radioactively labelled DNA were denatured by incubation for five minutes at 95° C. and kept single stranded by rapidly chilling on ice, before addition to HB. After 2 hours of prehybridization, the labelled probe was added to the hybridization buffer. Hybridization was conducted at 65° C. for 17 hours. After hybridization, blots were washed for 30 minutes with 4×SSC+0.1% SDS, followed by a 30 minute washing step in 2×SSC+0.1% SDS and a final 30 minute wash in 1×SSC+ 0.1% SDS. The washed blots were then dried and exposed at −70° C. to radiographic film in an X-ray cassette using regular enhancement screens (Amerham Life Sciences™). The exposed films were developed in an automatic developer. An estimation of the fragment length of hybridizing fragments is shown in Table 2A, including a 5.5 kb EcoRI fragment.

TABLE 2

Restriction analysis of genomic DNA or *A. niger* N400.

| Restriction Enzyme | Hybridizing Fragment Length |
|---|---|
| A. The approximately 750 bp SstI-SstII fragment of pIM 4120 (*A. niger* NRRL 3112) was used as probe. | |
| SstII | >6 kb* + 2.2 kb* + 1.9 kb |
| BamHI | >6 kb + 1.7 kb |
| EcoRI | 5.5 kb |
| HindIII | >6 kb |
| SalI | >6 kb |
| SstI | >6 kb |

Products indicated with * are the result of a partial digest

TABLE 2-continued

Restriction analysis of genomic DNA or *A. niger* N400.
B. The 339 bp Eco RI-kpnI fragment of pIM 4121
(*A. niger* N400) was used as probe.

| | |
|---|---|
| XhoI | 1.8 kb |
| SstII | 3.3 kb + 0.3 kb |
| PstI | >6 kb |
| KpnI | >6 kb |
| HincII | 2.0 kb + 1.3 kb |
| BglII | >6 kb |
| BamHI | 1.3 kb + 1.0 kb |

Example 3.4

Screening of the *Aspergillus niger* N400 Genomic Library for the *Aspergillus* Aminopeptidase Gene.

For the screening of the *A. niger* N400 genomic library, $2.4 \times 10^3$ plaque forming units (pfu) per plate were plated on five Petri dishes of 15 cm in diameter using *E. coli* LE 392 (Promega Biotech™ Inc., Madison, Wis. USA) as plating bacterium. LM (10 µl tryptone, 5 g/l yeast extract, 10 mM NaCl, 10 mM MgCl$_2$) medium plus 1.5% (w/v) agar or 0.6% (w/v) agarose were used for the bottom and top layer, respectively.

After an overnight incubation of the Petri dishes at 37° C., duplicate filters (Hybond-N, Amersham™) were prepared from each plate. Crosslinking, prehybridization, hybridization and washing were performed as described in example 3.3.

Nine hybridizing plaques were punched from the plate using a Pasteur pipet and the phages were eluted from the agar plug in 500 µl SM buffer (0.1 M NaCl, 0.008 M MgSO$_4$, 0.05 M Tris-HCl pH 8 and 0.01% (w/v) gelatin). The phage stocks obtained were rescreened using the procedure described above with duplicate filters from plates each containing 50–100 pfu of the phage stocks.

After purification, the phages were propagated by plating out until confluent plates were obtained. The phages were eluted by adding 5 ml SM buffer on top of the agar and gentle shaking for four hours. The buffer containing the phages was transferred to microfuge tubes and centrifuged for 5 minutes at maximum speed in a microfuge to remove bacteria. The supernatant was transferred to a new microfuge tube, 20 µl chloroform was added and the number of pfu was determined. These phage stocks contained approximately $5 \times 10^{10}$ pfu/ml.

Example 3.5

Restriction Analysis of Aminopeptidase-Encoding Gene Containing Phages.

From Table 2A it is clear that the approximately 5.5 kb EcoRI fragment is a suitable fragment to clone the aminopeptidase gene of *Aspergillus niger* N400.

From each of the isolated phages (phage 1.11, 2.11, 3.11, 4.11, 5.11, 6.11, 9.11, 10.11, 11.11), DNA was isolated according to the methods of Sambrook et al. (1989). Five micrograms of the isolated DNA was digested with EcoRI (30 units) for 4 hours at 37° C. and then subjected to gel electrophoresis as previously described in example 3.1. After separation, the DNA was denatured, transferred to a nitrocellulose membrane, crosslinked, prehybridized, hybridized and washed as described in Example 3.3. The SstI-SstII fragment of pIM4120 was used as a probe, as in example 3.3. Six phages were found to contain the approximately 5.5 kb EcoRI fragment, while three phages phages displayed smaller hybridizing bands.

The 5.5 Kb EcoRI fragment from phage 3.11 hybridizing to the 751 bp fragment was selected for cloning.

EXAMPLE 4

Cloning of the Aminopeptidase Encoding Gene.

20 µg of phage DNA of phage 3.11 was digested for four hours with 50 units EcoRI at 37° C. The fragments were separated by gel electrophoresis and recovered from the gel as described in example 3.1.

The 5.5 kb EcoRI fragment was ligated into vector pUC19 (Life Technologies™ Rockville, Md., USA (published in Gene 33, 103–119, 1985)) cut with EcoRI. Ligation was performed overnight at 16° C. with T4 DNA-ligase (Life Technologies™, Rockville, Md.), resulting in pIM 4121, shown in FIG. 7. Transformation to *E. coli* DH5α and plasmid DNA isolation of the transformants were done as described in example 3.2.

EXAMPLE 5

The Primary Structure of the Gene

Example 5.1

Sequence Analysis of the *A. niger* Aminopeptidase Encoding Gene.

The primary structure of the gene, and the 5' and 3' untranslated region, the coding region of the gene and the termination region were determined by sequencing the relevant fragments of pIM 4121. Because pIM 4121 does not contain sufficient promoter sequence, an overlapping fragment was cloned that contained more upstream sequence. Therefore, a new genomic Southern analysis was performed as described in example 3.3 using the restriction enzymes XhoI, SstII, PstI, KpnI, HincII, BglII and BamHI. A 339 bp EcoRI-KpnI fragment of pIM 4121(FIG. 7, probe 1) was used as a probe (labelled as described in example 3.3). The results are shown in Table 2B. The approximately 1.8 kb XhoI fragment (hereinafter denoted as the 1.8 kb XhoI fragment) partially overlapping the 5.5 EcoRI fragment of pIM4121 at the 5' end, was isolated from phage 3.11. This 1.8 kb XhoI fragment having an additional 260 bp promoter region, was cloned into pUC19 digested with SalI (SalI and XhoI have compatible ends), as described in example 4 resulting in pIM 4122. For the complete primary structure relevant fragments of both the pIM 4121 and the pIM 4122 were sequenced. For this, pIM 4121 and the pIM 4122 (FIG. 7) were further subcloned by standard DNA manipulation techniques (Sambrook et al., 1989). Restriction fragments were isolated as described in example 3.1 and cloned into pUC19 (Yannisch and Perron et al. 1985) as desribed in example 4. Plasmid pUC19 is commercially available through Life Technologies™ (Rockville, Md.).

Figure 7:
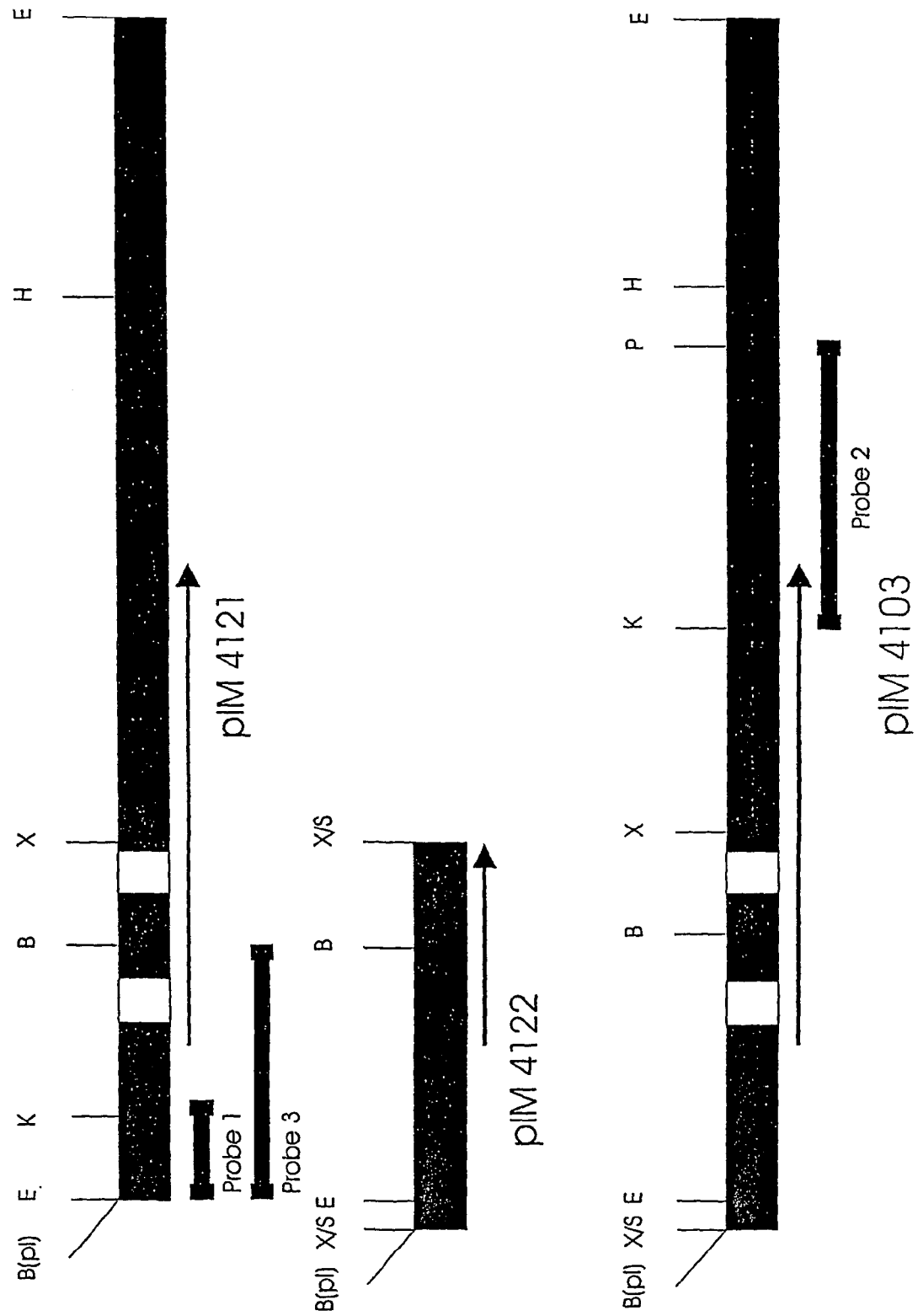
FIG. 7 shows the plasmid maps of pIM 4121, pIM 4122 and pIM 4103. Restriction enzyme sites are indicated in one letter code: E: EcoRI; B: BamHI; K: KpnI; X/S: Xho site cloned into a SalI site; P: PstI; X: XhoI; H: HindIII; B(pI): BamHI site originating from the polylinker of pUC 19. The heavy blunt-ended lines represent portions used as probes. Arrows indicate open reading frames. White boxes represent introns.

The complete sequence of the gene was determined for both strands, from the XhoI site upstream to the HindIII site downstream of the gene (FIG. 7). Sequencing was performed as described in example 3.2.

Example 5.2

Description of the Aminopeptidase Encoding Gene.

The sequence obtained was a 3922 bp XhoI-HindIII fragment, comprising a 731 bp fragment 5' untranslated region, a 1091 bp fragment 3' untranslated region (including stop codor) and a 2100 bp fragment encoding the aminopeptidase of the *Aspergillus niger* N400.

The open reading frame is interrupted with 2 intervening sequences. The precise location of these intervening sequences was determined with Reverse Transcriptase PCR (RT-PCR). *A. niger* N402 (described in Bos et al., 1988, Curr. Genet. 14: 437–443) was selected for further characterization of *A. niger* aminopeptidase. The aminopeptidase region of *A. niger* N402 is identical with that of *A. niger* N400. Thus, *A. niger* N402 was grown in growth medium (GM containing per liter 4.0 g NH$_4$Cl, 1.5 g KH$_2$PO$_4$, 0.5 g KCl, 0.5 g MgSO$_4$*7H2O, trace elements according to Vishniac and Santer (1957) 2% glucose, 0.1% yeast extract, 50 mM phthalic acid pH 5.5) for 17 hours. The mycelium was harvested by filtration and ground. Trizol reagent (Life Technologies™, Rockville, Md.) was used as recommended by the manufacturer to isolate total RNA from the ground mycelium.

RT-PCR was performed using the commercially available Enhanced Avian RT-PCRT kit (Sigma™, St. Louis USA) following the recommendations of the supplier.

First strand cDNA was generated with RT primers (Table 3) and was employed in several amplifications using various reverse and forward primer combinations (Table 3). The resulting PCR products were subjected to gel electrophoreses and extracted from the gel as described in example 3.1. The products were cloned in pGEM-T and sequenced as described in example 3.2. The cDNA sequence obtained was identical to the genomic *A. niger* N400 sequence from bp 520 to bp 2908, with the exception of two intervening sequences of 60 and 51 bp.

The primary structure of the *A. niger* N400 aminopeptidase ORF and upstream and downstream sequences are shown in FIG. 6 (SEQ ID NO: 1). The polypeptide derived from the coding sequence is 663 amino acid residues long (SEQ ID NO: 2). This polypeptide has a predicted molecular weight of approximately 72.5 kDa and a calculated isoelectric point (IEP) of 5.56.

TABLE 3

Primer sequences and combinations used in the RT-PCR

| RT reaction primer | Reverse primer | Nested primer |
|---|---|---|
| ApsC-13 | Sap-9 | Sap-10 |
| ApsC-13 | ApsC-11 | Sap-10 |
| Poly-T | ApsC-19 | ApsC-17 |
| Poly-T | ApsC-19 | ApsC-18 |

TABLE 3-continued

Primer sequences and combinations used in the RT-PCR

| Poly-T | Sap-3 | ApsC-12 |
|---|---|---|
| Sap-3: 5'-TGGGGNCCNGAYGGNAC-3' | | (SEQ ID NO:6) |
| Sap-9: 5'-CCGCAACCCTGACGTCC-3' | | (SEQ ID NO:13) |
| Sap-10: 5'-ACCAGGGCTGAACGTGG-3' | | (SEQ ID NO:14) |
| ApsC-11: 5'-TCGCGGGAACACCGCGG-3' | | (SEQ ID NO:15) |
| ApsC-12: 5'-CAATGATGACGAGACGC-3' | | (SEQ ID NO:16) |
| ApsC-13: 5'-GTTCCACTGGATCCAAGACACTC-3' | | (SEQ ID NO:17) |
| ApsC-17: 5'-TGCGGTAGGCACGACCG-3' | | (SEQ ID NO:18) |
| ApsC-18: 5'-CTCTTTCACTGGATGGC-3' | | (SEQ ID NO:19) |
| ApsC-19: 5-GGCTCCTGGGATCTTGC-3' | | (SEQ ID NO:20) |
| Poly-T: 5'-TTTTTTTTTTTTTTTTTTTTTTTV-3' | | (SEQ ID NO:21) |

Example 5.3

Comparison of the Aminopeptidase Encoding Gene Sequence of *A. niger* NRRL 3112 and *A. niger* N400.

Based on the genomic sequence of the gene encoding the aminopeptidase of *A. niger* N400, two specific primers: ApsC-11, ApsC-12 (Table 3) were designed, which were used in a PCR reaction using genomic DNA of *A. niger* NRRL 3112 as described in example 3.1. This resulted in an amplified fragment of approximately 1260 bop which was 98% identical to the sequence of *A. Niger* N400. In a comparison of the *A. Niger* KNURL 3112 sequence (SEQ. ID NO:3) obtained by PCR and the *A. Niger* N400 genomic sequence (SEQ. ID NO:24) (Table 4), 28 differences were found, including several point mutations, 26 of which had no effect on the amino acids encoded by the two sequences. Two of these point mutations resulted in amino acid substitutions. The change of an A into a T at position 951 in the sequence resulted in the replacement of a glutamic acid in N400 with an aspartic acid in NRRL 3112. The substitution of a G for an A at position 1052 resulted in the change of glutamic acid in N400 to a glycine in NRRL 3112 (Table 4).

TABLE 4

Alignment of *A. niger* NRRL 3112 Sequences obtained by PCR and *A. niger* N400 Genomic Sequence

| N400 | TCGCGGGAACACCGCGGAACTAATCTGGCTGGTGGATGTCACAACGATGCTTGTGCTCAGTTCCC |
|---|---|
| NRRL3112 | TCGCGGGAACACCGCGGAACTAATCTGGCTGGTGGATGTCACAACGATGCTTGTGCTCAGTTCCC |

TABLE 4-continued

Alignment of *A. niger* NRRL 3112 Sequences obtained by PCR and *A. niger* N400 Genomic Sequence

```
N400      CTCCCTGCTAAATTTCACCCGGTACCTGATTATTGCACTACTTCAACCCCCTCATCCGGCCACGT
NRRL3112  CTCCCTGCTAAATTTCACCCGGTACCTGATTATTGCACTACTTCAACCCCCTCATCCGGCCACGT

N400      CCATCTTTCTTTTTACGCCCTCCAAAAATATTTCATCCATTCACTTACTCTCTAAGACACTCCCA
NRRL3112  CCATCTTTCATTTTACGCCCTCCAAAAATATTTCATCCATTCACTGACTTTCTAAGACACGCCCA

N400      AT-TTTCCAGTCAACCAAATGGCTACCCCCGCAGAAGCTCAGACAGCTCCCTTCGGCACTTGGGA
NRRL3112  ATATTTCAAGTCAACCAAATGGCTACCCCCGCAGAAGCTCAGACAGCTCCCTTCGGCACTTGGGA

N400      CAGTCCCATCACAGCCGCAACCCTGACGTCCAAAGGCATCAGTTTCTCCGGCATCGCGGCCGCGG
NRRL3112  CAGTCCCATTACAGCCGCAACCCTGACGTCCAAAGGCATCAGTTTCTCCGGCATCGCGGCCACAG

N400      TTCGTCCCCTTCTCCTCTATATCCTACTACGTCCGAATTAAATTGACCTCTCCCTTCAGGCGGAT
NRRL3112  TTCGTCCCCTTCTCCTCTGTATCCTACTACGTCCGAATTAAATTGACCTCTCCCTGCAGGCGGAT

N400      GGTACCATCTACGTGAATGAAGGCCGCCCTGCCGAAGAAGGTCGCAATTGTATCGTCGAATGGCG
NRRL3112  GGTACCATCTACGTGAATGAAGGCCGCCCTGCCGAAGAAGGTCGCAATTGTATGGTCGAATGGCG

N400      CAACAACCAGCCCCGTGACGTTTTACCAGCTGCCTACAGTGCCCGCACAGCCGTCCACGGCTACG
NRRL3112  CAACAACCAGCCCCGTGACGTTTTACCAGCTGCCTACAGTGCCCGCACAGCCGTCCACGGCTACG

N400      GCGGCGCGGCGTTCAACACCACGTCAGACGGAAAGGTGATCTTCGCAGACTGGAAAACTCACGGG
NRRL3112  GCGGCGCGGCGTTCAACACCACGTCAGACGGAAAGGTGATCTTCGCAGACTGGAAAACTCACGGG

N400      GTGTATATACTTGATCCTGCCACTTGTGATGTAACAGCAGCCGTGGAACCAGACGAAAAGATCTG
NRRL3112  GTGTATATGCTTGATCCTGCCACTTGTGATGTAACAGCAGCCGTGGAACCGGACGAAAAGATCTG

N400      GTACGCTGCGTTCAATTCCCACCCCAAGAGACCAGAATTGGTGTTTGCTATCAGGGAGGATCACC
NRRL3112  GTACGCTGCGTTCAATTCCCACCCCAAGAGACCAGAATTGGTGTTTGCTATCAGGGAGGATCACC

N400      ACGGCAAGGAGGTGGTCAATGAGCTTGTCGTAATCAATACCGGGAATAAGAAGGTGGAGGTTGCA
NRRL3112  ACGGCAAGGAGGTGGTCAATGAGCTTGTGGTAATCAATACCGGGAATAAGAAGGTGGAGGTTGCA

N400      GCGACGGGAGCGGACTTTTACTCGCATCCCACGTTCAGTCCTGCTGGTGATAGAGTGTCTTGGAT
NRRL3112  GCGACGGGAGCGGACTTTTACTCGCATCCCACGTTCAGCCCTGCTGGTGATAGAGTGTCTTGGAT

N400      CCAGTGGAACCATCCCGAGATGCCGTGGACGGGAACTGAGTTGTTTTCCGCACCGTGGAAGGATG
NRRL3112  CCAGTGGAACCATCCCGAGATGCCGTGGACGGGAACTGAGTTGTTTTCCGCACCGTGGAAGGATG

N400      AGAAGGTTGGAACCCCTGTGAAATTGGCAGGGAATGGCGAAGAAGAAAGTATCTTGCAACCGAGA
NRRL3112  AGAAGGTTGGAACCCCTGTGAAATTGGCAGGGAATGGCGATGAAGAAAGTATCTTGCAGCCGAGA

N400      TGGGGACCAGACGGAACCTTGTTCTTTGTGTCGGATCGCACTGGATATTGGCAGTTTTATCGCTG
NRRL3112  TGGGGACCAGACGGAACCTTGTTCTTTGTGTCGGATCGCACTGGATATTGGCAGTTTTATCGCTG

N400      GAGCCCGGATGAAAGTGATGAGCCCCGCGCTATCGTTATTGAAGGCCTGGAGAAGGGCGAGTTCG
NRRL3112  GAGCCCGGATGGAAGTGATGAGCCCCGGGCTATCGTTATTGAAGGCCTGGAGAAGGGCGAGTTCG

N400      CTCACCCAGAATGGCTCCTGGGATCGTATGACTCCTAACCCTCCTGCTCACATAGTATATATCTA
NRRL3112  CTCACCCAGAATGGCTCTTGGGATCGTATGACTCCTAACCCTCTTGCTCACATAGTATATATCTA

N400      ACACGATGCAGTTGCACATATGTTCTTCCAAACGCCAACACAATTGTTGCAGCCTGGACGCAAAA
NRRL3112  ACACGATGCAGTTGCACATATGTTCTTCCAAACGCCAACACGATTGTTGCAGCCTGGACGCAGAA

N400      CGCAACGGAGCGTCTCGTCATCATTG
NRRL3112  CGCAACGGAGCGTCTCGTCATCATTG
```

Example 5.4

Comparison of the Sequence of the Gene Encoding the *A. niger* Aminopeptidase with Sequences Known from Databases.

The protein sequence of the aminopeptidase as depicted in SEQ ID NO: 2 was compared to the PIR, PIRNEW, PIRALERT, SWISSPROT, GENESEQPROT and YEASTPROT databases, using the program BLASTP (Altschul et al, 1997, Nucleic Acids Research 25: 3389–3402). The BLOSUM62 matrix was used for the search, and the expected threshold used was 10. The most significant homology was found with a hypothetical protein slr0825 from *Synechocystis* sp. (strain PCC 6803, accession number PIR S75772; SEQ ID NO: 22). Identity with this hypothetical protein was 35% over 653 amino acids, as shown in Table 5. Homology was also found with hypothetical proteins F01 F1.5 and F44B9.1 from *Caenorhabditis elegans* (accession numbers PIR TI 5945, SEQ ID NO:23 and PIR S44807 respectively). Identity is 30% over 655 amino acids for F01 F1.5 and 28% over 256 amino acids for F44B9.1. Lower homologies were found with acylaminoacyl-peptidases from varying origin, suggesting that the peptide of SEQ ID NO: 2 has peptidase activity.

Surprisingly, the amino acid sequence in SEQ ID NO: 2 does not show a clear distinguishable amino-terminal signal sequence for secretion of the polypeptide to the extracellular medium, despite the fact that the sequenced protein was initially isolated from the culture medium of *A. niger* NRRL 3112. Additionally, peptide number 3 is almost identical to amino acids 5 to 20 of the SEQ ID NO: 2 sequence, suggesting that no cleavable amino-terminal signal sequence is present in this protein. This suggests that the protein exits the cell by an unknown mechanism, that does not include amino terminal processing of a signal peptide.

TABLE 5

Alignment of the amino acid sequence of SEQ ID NO: 2 with the most homologous sequences from the databanks.
Alignment has been performed with the CLUSTALW program.

```
seq_id_2      MATPAEAQTAPFGTWDSPITAATL-TSKGISFSGIAAAADGTIYVNEGRPAEEGRNCIVE
pir_s75772_2  MISMTTKQIAPYGSWRSPITADAL-LAGSIGLGAVQNSGEDVFWL-EARPAEKGRNVLVH
pir_t15945_3  -----MATEAVYGSWDSPITPDLFGKCNCKSICEMQVVGGNVYWI-EQNSVTGKRELYSK
                   * :*:* ****.  :    .:  :    ...::  *  ...    *:    .

seq_id_2      WR-NNQPRDVLPAAYSARTAVHGYGGAAFNTTSDGKVIFADWKTHGVYILDPATCDVTAA
pir_s75772_2  RQPDGTVRDVTPAPFNVRTRVHEYGGGAFLVTADG-VYFSNFSDQQVYVQGVGQEPQRLT
pir_t15945_3  PT-NGDTRTRWADGQSVQTAIHEYGGGALHVLADGSVLFATIEG--VFYQKSADSGVEQL
               :.  *    .   ..:* :* ***.*: .  :**  *  *:    *:      .

seq_id_2      VEPDEKIWYAAFNSNPKRPELVFAIREDHHGKEVVNELVVINTGNKKVEVAATGADFYSH
pir_s75772_2  NRPDCRFADFVLD-QPRQRLIAVGERHHSEAKEPENFLAAISLENGEVTTIATVHDFYSS
pir_t15945_3  AEGNNRMFRFSDFSATDTHVFCVNETHQADAKFPENRLISIDRATKNQNVIAHGADFYAY
               . : ::          .    :.   .. ..*    *  *  *:.   .  *    ***:

seq_id_2      PTFSPAGDRVSWIQWNHPEMPWTGTELFSAPWKDEKVGTPVK-LAGNGEEESILQPRWGP
pir_s75772_2  PRLSPDGQKLQWITWDHPHMPWDATQLWLADIDQAGNLSNLKIIAGQAGNESIHEPQWSP
pir_t15945_3  PRVSPDGKKLVWMQWSLPNMPWDETSIRMADLKGGESSNEVTLKDGTGKQINYSEPTWDG
               *  .** *.::  *: *.  *.***  *.:  *      .  :.    *  .:     :* *..

seq_id_2      DGTLFFVSDRTGYWQFYRWSPDESDEPRAIVIEGLEKGEFAHPEWLLGSCTYVLPNANTI
pir_s75772_2  DGSLYFVGDRTDWWNLYRYHKGEVDN----VFP-LD-AEFAYPHWVFGLRSYTFVDTDTI
pir_t15945_3  D-ELLTVNDSTNWWNVYKSAEPNSVEKIN-LNP-IQ-REISYPLWQLGFRNYVLNKKYLV
              *   *  *.*  *.:*:..*:      .      :  ::   *:::* * :*   .*.:  .  :

seq_id_2      VAAWTQNATERLVIIDLEKNTYTFPAHIASLTGIQHSAVALTSPTSIAVIASTPTAPSTV
pir_s75772_2  LCTFTQDGAWQLGKLKPSRKQLS----ILGLPYSNYSSLCSDGKT-LWFIGSGPTTSSAV
pir_t15945_3  MNA---DGILYVRSGDVTVEIPT-----PGYTVFGYLSLDQNGSD-LFAIASGPKRASSV
              :  :    :.   :      :  :     ..    :  ::      .    :  *.* *. ..*:* seq_id_2      YHISLTNNDAFAPTVLRSSTSVTISDTYFSRAQHISFPRTISTHPDTLSHAFFLPPTNPK
pir_s75772_2  VALAV---EAQETEILKVASDFTLDPAYLAQPQAISF----SGDDGQTAHAWYYPPTNGD
pir_t15945_3  ISIDL----ANKNFPLKVHRES--RDSSEIDALEISE----------PEE-FVFKSDGVD
               : :      *       *:  .    :     .**             . :   ...

seq_id_2      YSSAPGELPPLIITIHGGPTIHTDPGLSMMWQYYTTRGYAVALLNYAGSSGYGRAYRKLL
pir_s75772_2  FRGPSDALPPLLVKSHGGPTAAAGNSLSLKIQYWTSRGFAYVDVNYGGSTGYGRDYRQRL
pir_t15945_3  VS--AGTLPPVLLLGHGGPTAPAQNNLDLKKQFFTSRGIAVFDVNYRGSTGFGTEFRRML
               ..  *::: ***  :   .*.:  *:;*:** *    : :*:*  :*: * seq_id_2      NGSWGVLDVHDAADCARYLISEGKVHPSRIGITGVSSGGYATLQAICMFPTLFTGAVSVS
pir_s75772_2  NGQWGIVDVADCVNAARYLADQGLVDGEQLAISGGSAGGYTTLAALT-FHNVFKAGASYY
pir_t15945_3  YKNCGVADRDDMLNGAKALVEQGKVDAEKVLITGSSSGGYLILSCLISPKNIIKAAVSVY
               . *: *    *    : *: *  .:*  *.  .::  *:*  *:888    *  .:     .::....* seq_id_2      GISDVEALVAETHKFESHYAFRLLFDDKVPETEEEKRKVYRERSPRFHADKIKAKLLLLQ
pir_s75772_2  GVSDLTAtATDTHKFEARYLDGLIG--PYPE----RKDLYERRSPVNHADQLTCPVIFFQ
pir_t15945_3  GVADLLALDEDTHKFLERCYNEMLIG--KYPE----QASIYEERSPIYHIDKIRTPIAFLH
              *::*: **  :***;*   *  *:       **       :..*..*** * *::     : :::

seq_id_2      GTDDEIVPLNQAQAMADDVQRSGGVAKLVIFEGEGHGYPRKAENQLQAKEVEEGWWKVNL
pir_s75772_2  GLEDKVVPPNQTEMMVQALKAKGIKVEYVAFPEEQHGF-RMAANIKKALESELAFYGEVF
pir_t15945_3  GREDTVVPMSQSITMYEKIRASGVTTALMLFDGEGHGF-RNGQVIKESTEATFYFLMKAV
              *  :*  :**  .*:   *  : ::  .   :  *  * **:  * .    ::  *    :    .

seq_Id_2      AEVNGE----------
pir_s75772_2  GFTPAKN---------
pir_t15945_3  GIEPSISSKIEIVNPKH
```

EXAMPLE 6

Expression of the Cloned ApsC Gene in *Aspergillus niger*.

Example 6.1

Construction of pIM 4103.

Since only minor differences exist between the amino acid sequences of the *A. niger* NRRL 3112 aminopeptidase and the *A. niger* N400 aminopeptidase, further characterization of *Aspergillus* aminopeptidase activity was performed using the enzyme encoded by *A. niger* N400 as representative of the gene encoded by several *A. niger* subspecies. Because pIM4121 lacks a sufficient promoter sequence, the fragment was extended at the 5' end with an approximately 270 Bp XhoI-EcoRI fragment from the partially overlapping XhoI fragment. To this end, pIM4121 was digested with BamHI, subjected to gel electrophoreses as described in example 3.1 and the approximately 7 kb fragment (containing vector and a part of the gene) was recovered as described in example 3.1. This 7 kb fragment was dephosphorylated using calf intestine alkaline phosphatase (ciap, Life Technologies™, Rockville, Md.) according to the supplied instructions. Phenol/chloroform extraction was then performed to remove the calf intestine alkaline phosphatase enzyme, and the 7 kb fragment was precipitated using standard methods (Sambrook et al. 1989), and dissolved in 5 µl $H_2O$. pIM4122 was digested with BamHI, subjected to gel electrophoreses (example 3.1) and the approximately 1.4 kb BamHI fragment was recovered from the gel (example 3.1). The approximately 1.4 kb BamHI fragment was ligated with the 7 kb BamHI fragment. Ligation was done as described in Example 4, transformation and plasmid DNA isolation of the transformants were performed as described in example 3.2. The resulting plasmid is denoted pIM 4103 (FIG. 7), and was deposited under accession number CBS 102481 (available at CBS (Centraal Bureau voor Schimmelcultures), The Netherlands).

Example 6.2

Transformation of pIM4103 in *A. niger* NW171

For a published description of *A. niger* NW171, see EJB 1997, vol 247, 605–613, available upon request from Wageningen University, Wageningen, The Netherlands.

The plasmid pIM4103 was introduced in *A. niger* by co-transformation of *A. niger* NW 171 (fwnA6, pyrA6, nicA1, pepA::argB$_{nid}$ΔA, pepB::argB$_{nid}$ΔB, pepE::argB$_{nid}$ΔE) (described by van den Homberg et al. 1997) using as a selective marker the *A. niger* pyrA gene, located in plasmid pGW635 (described by Goosen et al., (1989)) and the plasmid pIM4103 as the co-transforming plasmid.

Protoplasts were prepared from mycelium by growing *A. niger* NW171 in minimal medium (per L: 6.0 g NaNO$_3$, 1.5 g KH$_2$PO$_4$, 0.5 g MgSO4*7H2O, 0.5 g KCl, 1 ml Visniac solution (Visniac, W., Santer, M. (1957), pH 6.0) supplemented with 50 mM glucose, 0.5% yeast extract, 0.2% casamino acids and 10 mM uridine for 20 hours at 30° C. The preparation of protoplasts of *A. niger* NW171 and the transformation procedure was performed as described by Kursters-van Someren et al., (1991) current genetics, 20:293–299, using 1 µg pGW635 and 20 µg pIM4103. Transformants were selected for their ability to grow in the absence of uridine.

Example 6.3

Selection of High Copy Transformants of pIM4103.

Figure 8:
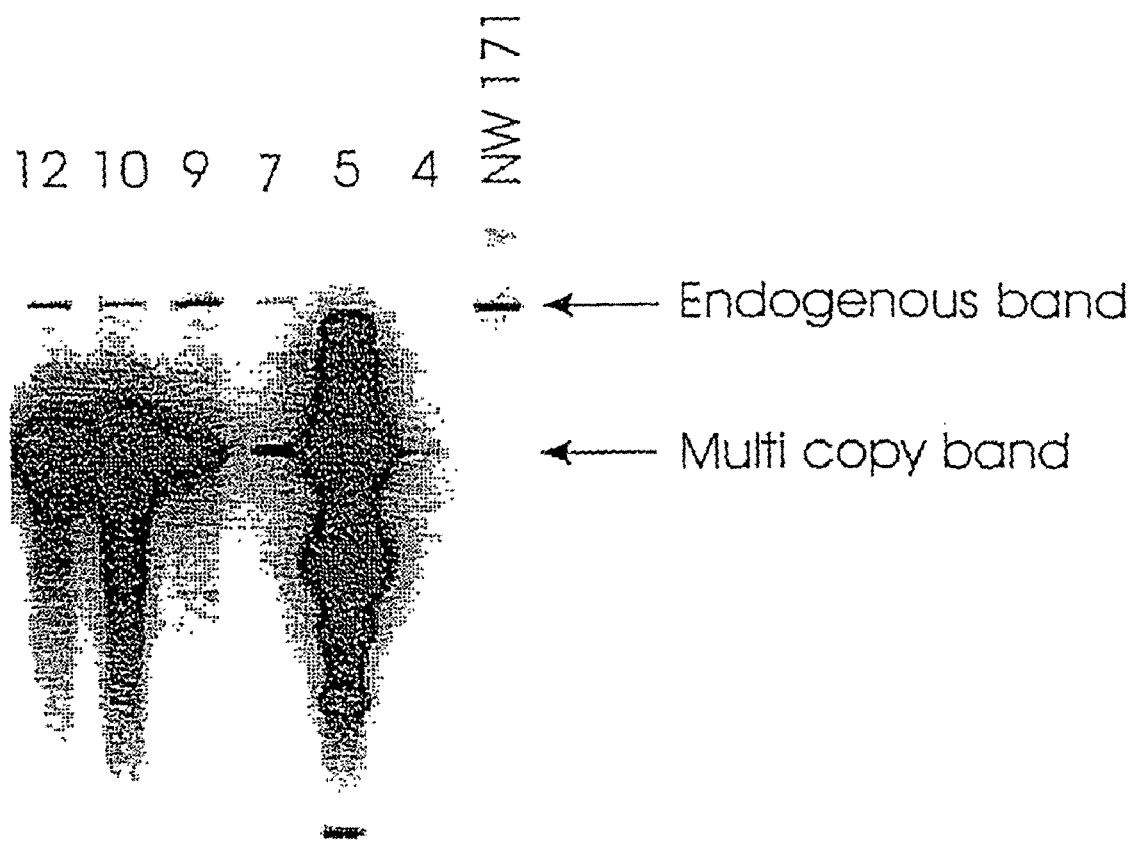
FIG. 8 shows a Southern blot of aminopeptidase transformants. HindIII digested genomic DNA of the parental strain *A. niger* NW 171 and 6 transformants were analyzed. The numbers above the lanes represent *A. niger* NW171 and transformants thereof. Two hybridizing restriction fragments are indicated, one originating from the endogenous aminopeptidase gene and one originating from (multiple) integrations of pIM 4103 in the genome. The other bands are probably the result of scattered integrations.

Genomic DNA from a selection of transformants was isolated according to the method of De Graaff et al (1988). 5 µg DNA was digested as described in example 3.3 using HindIII. After electrophoresis, the DNA was denatured and transferred to a nitrocellulose membrane as described in example 3.3. The membranes were crosslinked, and prehybridzed in HB (as described in example 3.3) for 2 h and hybridized with the [α-$^{32}$P]-dATP labelled 845 bp KpnI-PstI fragment (FIG. 7, probe 2) in HB (labelled as described in example 3.3) at 65° C. Washing was performed as described in example 3.3. The results are shown in FIG. 8.

RNA was isolated from the same selection of transformants, as described in example 5.2. 10 µg of the isolated RNA was denatured using glyoxal (Sambrook et al. 1989) and size separated by gel electrophoresis (1.6% agarose in 10 mM phosphate buffer pH 7) at 8.3 V/cm for 1.5 h. After separation the RNA was transferred to a nitrocellulose membrane and prehybridized in HB as described in example 3.3. The 845 bp KpnI-PstI fragment labelled with [α-$^{32}$P]-dATP was heat denatured and rapidly chilled on ice before addition to Northern hybridization buffer (NHB (6×SSC, 5× Denhardts solution, 0.5% SDS, 10% dextran sulfate and 50% formamide).

Figure 9:
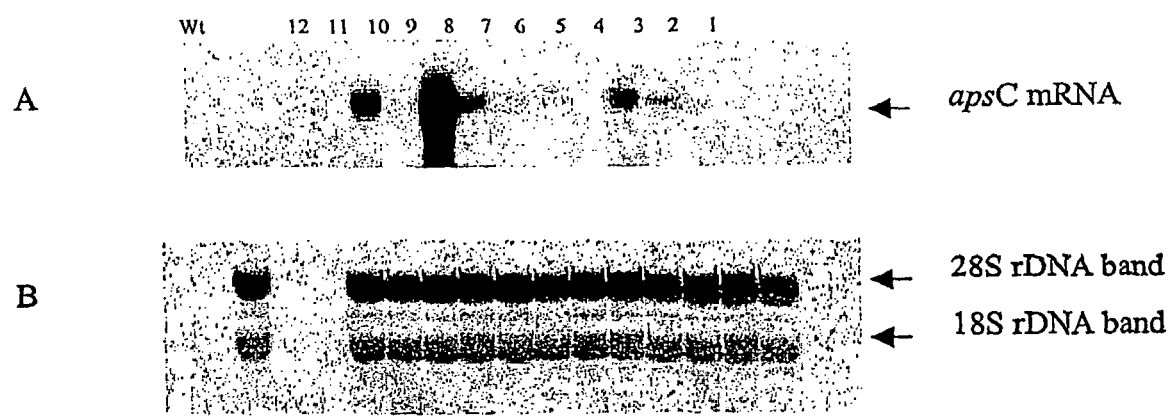
FIG. 9 shows a Northern blot of the parental strain *A. niger* NW171 and transformants thereof containing plasmid pIM 4103. The numbers above the lanes represent *A. niger* NW 171 and transformants thereof.

Hybridization was performed at 42° C. for 17 hours, washing was performed as described in example 3.3. As shown in FIG. 9, transformant 10 appeared to have the highest copy number and the highest mRNA levels for the gene of interest. Hereinafter, transformant 10 is called *A. niger* NW171::pIM4103–10.

EXAMPLE 7

Purification and Characterization of the *Aspergillus niger* Aminopeptidase.

Example 7.1

Purification of the *Aspergillus niger* Aminopeptidase from Culture Filtrates.

A 300 ml culture filtrate was obtained by the culturing of *A. niger* strain NW171::pIM4103–10, in complete medium (CM), pH 6.0, containing per liter 4.0 g NH$_4$Cl, 1.5 g KH$_2$PO$_4$0.5 g KCl, 0.5 g MgSO$_4$*7H$_2$O, 1 g yeast extract, 2 g meat peptone (peptone 100, Gibco BRL), 1 g peptone 140 (Gibco BRL), 0.3 g yeast ribonucleic acids (Sigma), 2 ml vitamin solution, trac elements according to Vishniac and Santer (1957) and 2% glucose per liter. The vitamin solution contained per 100 ml: 10 mg thiamine, 100 mg riboflavin-5p, 10 mg p-aminobenzoic acid, 100 mg nicotinamide, 50 mg pyridoxine-HCl, 10 mg panthenoic acid, and 2 mg biotin.

A 300 ml volume of the medium was inoculated with 106 spores/ml and incubated at 30° C. for 7 days in an orbital shaker set at 250 rpm. The culture fluid was harvested by filtration and the filtrate was adjusted to pH 7. To 300 ml culture fluid (NH$_4$)$_2$SO$_4$ was added to 60% saturation. After stirring for 30 min the precipitated protein was recovered by centrifugation for 15 min at 11,000×g. To the supernatant (NH$_4$)$_2$SO$_4$ was added to a final concentration of 90% saturation. After stirring for 30 min the precipitated protein was recovered by centrifugation for 15 min at 11,000×g. The resultant pellet was solubilized in 20 ml phosphate buffer (PB) pH 7.2, which was prepared by mixing 100 mM Na$_2$HPO$_4$ and 100 mM KH$_2$PO$_4$ until the desired pH was obtained. The resulting solution was dialyzed against 2 liters of 10 mM triethanolamine (TEA) pH 7. All dialysis steps were conducted for 2 hours with the exception of the last step, which was performed for 17 hours.

After dialysis the solution was applied to a 15.5 ml SourceQ column (Pharmacia Biotech™) equilibrated in 20 mM TEA, pH 7.0. Bound protein was eluted using a 124 ml linear gradient from 0 to 0.4 M NaCl in 20 mM TEA pH 7.0. The aminopeptidase activity eluted at a NaCl concentration between 240 and 290 mM. This corresponded with fractions 15 and 16, which were pooled and 5 fold diluted in 20 mM Bis-Tris pH 6.5. The resulting sample was applied to a 1 ml Resource Q column (Pharmacia biotech™) equilibrated in 20 mM Bis-Tris pH 6.5. The bound protein was eluted using a 20 ml linear gradient from 0 to 0.4 M NaCl in 20 mM Bis-Tris pH 6.5. The aminopeptidase activity eluted at an NaCl concentration between 210 and 250 mM. Fractions of 2 ml were collected.

In all steps, aminopeptidase activity was determined spectrophotometrically (OD$_{400}$) by measuring the release of para-nitroanilide from phenylalanine-para-nitroanilide (Phe-pNA, Sigma chemical co. St. Louis) in a reaction mixture containing 400 µl of 1 mM Phe-pNA (dissolved in 7.5 mM HCl) and 600 µl of 100 mM PB pH 7.2. The molecular mass of aminopeptidase and the purity were determined by SDS-PAGE as previously described (see Laemmli, 1970) on a 10% gel (FIG. 14). The apparent molecular mass was 72 kDa.

Example 7.2

Purification of the *A. niger* Aminopeptidase from Mycelial Extracts.

Aminopeptidase was purified from mycelium by culturing *A. niger* strain NW171::pIM4103–10 in CM (example 7.1) in shaker flasks for 48 hours. After harvesting by filtration, 50 g of the mycelium was ground and resuspended in 70 ml 100 mM PB pH 7.2. After centrifugation at 10.000×g for 15 minutes, the supernatant was transferred to a new tube. Protein was precipitated by bringing the supernatant to a concentration of 60% saturation with NH$_4$SO$_4$. After stirring for 30 min the precipitated protein was removed by centrifugation for 15 min at 11,000×g. The supernatant was then brought to a concentration of 90% saturation with (NH$_4$)$_2$SO$_4$. After stirring for 30 min, the precipitated protein was recovered by centrifugation for 15 min at 11,000×g. The pellet was solubilized in 30 ml 200 mM PB pH 7.2. The resulting solution was dialyzed three times against 2 L of 10 mM triethanolamine (TEA) pH 7.0. The first two dialysis steps were conducted for 2 hr, while the final dialysis was conducted for 17 hr. After dialysis, the protein mixture was loaded onto a 15.5 ml SourceQ™ column (Pharmacia biotech™), equilibrated in 20 mM TEA pH 7.0. Bound protein was eluted using a 124 ml linear gradient from 0–0.4 M NaCl in 20 mM TEA. The aminopeptidase activity eluted at a NaCl concentration between 240 and 290 mM. Fractions of 5 ml were collected, and those containing aminopeptidase activity were pooled. Pooled fractions were diluted 10-fold with H$_2$O and loaded onto a 1 ml ResourceQ™ column (Pharmacia biotech™) equilibrated in 20 mM TEA pH 7.0. Bound protein was eluted using a 15 ml linear gradient from 0–0.4 M NaCl in 20 mM TEA, pH 7.0. The aminopeptidase activity eluted at an NaCl concentration between 240 and 290 mM. Fractions of 1 ml volume were collected. During the purification process, aminopeptidase activity was determined as described hereabove. The molecular mass and the purity of the aminopeptidase were visualized by SDS PAGE. The obtained enzyme was at least 95% pure, essentially forming a single band free from other detectable contaminants.

EXAMPLE 8

Biochemical Characterization of Aminopeptidase

Example 8.1

The pH Optimum of Purified Aminopeptidase Using Phe-pNA as Substrate.

Aminopeptidase activity was measured using Phe-paranitroanilide (pNA, Sigma™ chemical co (St. Louis)) as the substrate. McIlvaine buffer (100 mM citric acid mixed with 200 mM Na$_2$HPO$_4$ until the desired pH is obtained) was used as buffer. Phe-pNA was dissolved in 7.5 mM HCl in a final concentration of 2.5 mM. 10 µl purified enzyme was added to 600 µl buffer and 400 µl Phe-pNA. Activity was measured spectrophotometrically at 400 nm, by measuring the change in absorbance per minute at 30° C.

Specific activity was calculated using following formule:

$$\frac{\text{change in absorbance (at 400 nm)}}{\varepsilon \text{ substrate} * \text{amount of enzyme} * \text{concentration of enzyme}}$$

The cuvet volume was 1 ml. ε substrate is 9.6 µm/cm. The results are presented in FIG. 10. The pH optimum is 5.

The pH optimum of purified aminopeptidase using Leu-pNA as substrate.

Aminopeptidase activity was measured using Leu-paranitroanilide (pNA, Sigma chemical co (St. Louis)) as the substrate. McIlvaine buffer (100 mM citric acid mixed with 200 mM Na$_2$HPO$_4$ until the desired pH is obtained) was used as buffer.

Phe-pNA was dissolved in 7.5 mM HCl in a final concentration of 1 mM. 10 µl purified enzyme was added to 600 µl buffer and 400 µl Leu-pNA. Activity was measured spectrophotometrically at 400 nm, by measuring the change in Absorbance per minute at 30° C. Specific activity was calculated using following formula:

$$\frac{\text{change in absorbance (at 400 nm)}}{\varepsilon \text{ substrate} * \text{amount of enzyme} * \text{concentration of enzyme}}$$

The cuvet volume was 1 ml. ε substrate is 9.6 µM/cm. The results are presented in FIG. 11. The pH optimum is between 5 and 8.

Example 8.2

The Temperature Stability of Purified Aminopeptidase.

Microfuge tubes containing 100 µl of 0.055 mg/ml protein in PB pH 7.2 of the purified aminopeptidase were preincubated in a water bath at 30° C., 40° C., 50° C. or 60° C. for 60 minutes. One sample was kept on ice during 60 minutes as a reference. Aminopeptidase activity was measured as described in example 8.1 using Phe-pNA as a substrate and 100 mM PB buffer pH 7.2 as the buffer. The reaction temperature was 30° C.

Residual activity was calculated as follows:

$$\frac{\text{Specific activity of the preincubated sample}}{\text{Specific activity of the reference sample}} * 100\%$$

The results are shown in FIG. 12. After an incubation for 60 minutes at 50° C., the activity was 90% of the activity of the reference sample. After 60 minutes at 60° C., the activity was approximately 25% of the activity of the reference sample.

Example 8.3

Substrate Specificity of the Purified Enzyme

Phe-para-nitroanilide (Phe-pNA), Arg-pNA, Ala-pNA, Met-pNA, Leu-pNA, Pro-pNA, Lys-pNA, N-acetylalanine-pNA (NacA-pNA), Trp-β-napthylamide (Trp-βNA), His-βNA, Ser-βNA, Leu-βNA, Phe-βNA were obtained from Sigma chemical co (St. Louis).

Ile-pNA, Glu-pNA, Val-pNA, Gly-pNA, Asn-βNA, Thr-βNA, Tyr-βNA were obtained from Bachem (Switzerland).

All pNA substrates were made in 7.5 mM HCl at a final concentration of 2.5 mM. All β-NA substrates were dissolved in methanol at a final concentration of 10 mM. To the Asp-βNA substrate 20 µl acetic acid was added.

When using pNA substrates, the aminopeptidase activity was measured as described in example 8.1, except that 20 mM citric acid at pH 5.2 or 100 mM PB at pH 7.2 were used as buffer. When using the βNA substrates 10 µl purified enzyme was added to 100 µl substrate and 900 µl buffer. When using Phe-, Leu-, Trp- or Tyr-pNA at pH 7.2, 10 µl substrate was used in 990 µl buffer. Activity was measured in a Hitachi F-4500 Fluorescence spectophotometer using an exication wavelength of 340 nm and an emission wavelength of 455 nm. The activity is presented as the activity compared to the activity at Phe-pNA in case of the pNA substrates and compared tot he activity at Phe-βNA in case of the βNA substrates.

$$\frac{\text{Activity of amino acid-pNA}}{\text{Activity of Phe-pNA}} * 100\%$$

or $$\frac{\text{Activity of amino acid-}\beta\text{NA}}{\text{Activity towards Phe-}\beta\text{NA}} * 100\%$$

The results are shown in FIG. 13. The optimal substrate tested for the aminopeptidase at both pH's was Phe-pNA and Phe-βNA. The activity at Tyr-pNA and Trp-βNA was 72% and 27% compared to the activity observed with Phe-βNA at pH 5.2. At pH 7.2 these activities were 53% and 22% respectively. The results may be expressed as a ratio of phenylalanine:tyrosine:tryptophane aminopeptidase activity of approximately 1:0.53:0.22. From the above-mentioned activities it can be concluded that the aminopeptidase is an aromate specific aminopeptidase.

EXAMPLE 9

Screening of *Aspergillus* Species for the Presence of the ApsC Gene.

Chromosomal DNA was isolated from *Aspergillus niger* N402, *Aspergillus nidulans* (ATCC 48756), *Aspergillus tubingensis* (CBS 126.52), *Aspergillus oryzae* (ATCC 20386), *Aspergillus sojae* (ATCC 20387), *Aspergillus carbonarius* (CBS 111.26) and *Aspergillus foetidus* (CBS 103.14)

5 µg of DNA was digested with HindIII. Separation on an agarose gel, transfer to a nitrocellulose membrane, Southern hybridization and labeling of a probe was performed as described previously using a hybridization temperature of 56° C. and a 1090 bp EcoRI-BamHI fragment as probe (see FIG. 7, probe 3). The filter was washed 1×20 minutes with 4×SSC+0.5% SDS and 1×20 minutes with 2×SSC+0.5% SDS.

Hybridizing DNA fragments were found in digested chromosomal DNA of *A. niger, A. tubingensis, A. foetidus* and *A. carbonarius* (see FIG. 15). This indicates the presence of highly similar, homologous aminopeptidase genes in each of these *Aspergillus* strains.

All cited publications are incorporated herein by reference.

EXAMPLE 10

The isolated aminopeptidase of the invention was tested using the Ch-easy-model (Smit, G., Braber, A., Spronsen, W. A. van, Berg, G. van den and Exterkate, F. A. (1995). Ch-easy-model voor bestudering van de kaasrijping [The Ch-easy model for studying cheese ripening], *Voedingsmiddelentechnologie*, 28 (8): 19–21.). The Ch-easy with added aminopeptidase (according to the invention) was compared to two other batches, one being a neutral control (only addition of starter culture, Direct Starter TM 31LT1 [DSM Food Specialties, Australia]) and one with added Accelerzyme® AP2000 (DSM Gist, Seclin, France). Additions were based on enzyme activity and were the same for both batches (60 APU/100 g, with 1 Acidic Protease Unit being the amount of released Tyrosine following TCA precipitation of a hemoglobin substrate at pH 3.5 measured at 280 nm). Following two weeks ripening at 17° C. the Ch-easy batches were assessed using a professionally trained sensory analysis panel. The Ch-easy batch with addition of the aminopeptidase of the Invention received scores similar to the batch with added Accelerzyme®. Especially scores for overall (aged) taste and flavour set these two batches apart from the neutral control. An overall improvement was thus observed and both Ch-easy batches had obtained a well balanced taste and flavour as compared to the neutral control batch.

LITERATURE

Bussink, H. J. D.; Buxton, F. P.; Visser, J. (1991); Current Genetics 19:467–474

Feinberg, A. P. & Vogelstein B. (1983); Anal. Biochem 132: 6–13

Goosen, T., van Engelenburg, F., Debets, F., Swart, K., Bos, K. and van den Broek, H. (1989); Mol. Gen. Genet. 219:282–288.

De Graaff, L., Van den Broek, H. and Visser, J. (1988); Curr. Genet. 13:315–321

Harmsen, J. A. M.; Kusters-van Someren, M. A.; Visser, J. (1990); Current Genetics 18:161–166

Laemmli, U. K. (1970); Nature 227:680–685

Sambrook J. Fritsch, E. F., Maniatis T. (1989); Molecular cloning, A laboratory manual, 2nd edition, Cold Spring Harbor Laboratory Press, New York Van den Homberg van den J. P. T. W., Sollewijn Gelpke M. D., Vondervoort, van de P. J. I., Buxton F. P. and Visser J. 1997; European Journal of Biochemistry Vishniac W., Santer M. (1957) The Thiobacilli, Bacteriol. Rev. 21, 195–213.

Yanisch-Perron, C., Viera, J. and Messing, J. (1985); Gene 33, 103–119

The invention claimed is:

1. An isolated polypeptide which has phenylalanine aminopeptidase activity, selected from the group consisting of:
   (a) an isolated polypeptide from *Aspergillus* which has an amino acid sequence which has at least 80% amino acid sequence identity with amino acids 1 to 663 of SEQ ID NO:2; and
   (b) an isolated polypeptide from *Aspergillus* which is encoded by a polynucleotide which polynucleotide hybridizes under conditions of 6×SSC +0.5% SDS at 56°C. with a polynucleotide having the nucleotide sequence of SEQ ID NO:1
   wherein the isolated polypeptide is substantially free of a contaminating amyloglucosidase.

2. A polypeptide of claim 1 which has at least one of the following physicochemical properties:

(1) a molecular weight (when deglycosylated) of approximately 72 kDa; and
   (2) an isoelectric point of about 5.6.

3. A polypeptide of claim 2, wherein 90% of phenylalanine aminopeptidase activity is retained after incubation for 60 minutes at 50° C.

4. The polypeptide of claim 1, comprising the amino acid sequence of SEQ ID NO:2.

5. An isolated polynucleotide comprising a nucleic acid sequence which encodes the polypeptide of claim 1.

6. A nucleic acid construct comprising the polynucleotide of claim 5 operably linked to one or more control sequences that direct the production of the polypeptide in a suitable expression host.

7. A recombinant expression vector comprising the nucleic acid construct of claim 6.

8. An isolated recombinant host cell comprising the nucleic acid construct of claim 6.

9. A method for producing a polypeptide with aminopeptidase activity comprising cultivating the recombinant host cell of claim 8 to produce a supernatant and/or recombinant host cells comprising the polypeptide; and recovering the polypeptide.

10. A polypeptide produced by the method of claim 9.

11. A food composition comprising the polypeptide of claim 1.

12. The food composition of claim 11, which is a dough or a baked product thereof.

13. The food composition of claim 11, which is a cheese.

14. A food composition comprising the cells of claim 8.

15. The food composition of claim 14, which is a dough or a baked product thereof.

16. The food composition of claim 14, which is a cheese.

17. The polypeptide of claim 1, which has at least 95% identity with amino acids 1–663 of SEQ ID NO:2.

* * * * *

SEQUENCE LISTING

```
<160> NUMBER OF SEQ ID NOS: 27

<210> SEQ ID NO 1
<211> LENGTH: 3922
<212> TYPE: DNA
<213> ORGANISM: Aspergillus niger N400

<400> SEQUENCE: 1
ctcgagatcc gacgatatgc accatacctg atcgaaagta acatgcaaat tttcattgat      60
ggaggcattc gacgtggaac agatgtcctg aaggcccttg cattaggagc aactgctgtt     120
gggcttgggc gaccatttct gttcagtctg gcagccggct atggagcaga tgggacccgc     180
cgggccattc aaatcttgcg gcaggaaatt gaaatgaaca tggtgttcct gggcgtgaca     240
aagctgtcgg aattggggcc tcatttggtg aattcaatga ggctggaacg agatgtagtt     300
ggctcggtta aactgtgaag aggcaggctt ctgtagatta ctggatatga atatctcccc     360
aattcatatg gcattgttca catccaggca cagccttaac caggacacag accagttcgc     420
actaaatgga attaagaggg gcatgggctg accagtgcat attagtgcgt aagcactatt     480
ccccatgtaa ctggcacggg cttatcgaag ccattcggat cgcgggaaca ccgcggaact     540
aatctggctg tgggatgtca caacgatgct tgtgctcagt tcccctccct gctaaatttc     600
acccggtacc tgattattgc actacttcaa cccctcatc cggccacgtc catctttctt     660
tttacgcccct ccaaaaatat ttcatccatt cacttactct ctaagacact cccaattttc     720
cagtcaacca aatggctacc cccgcagaag ctcagacagc tcccttcggc acttgggaca     780
gtcccatcac agccgcaacc ctgacgtcca aaggcatcag tttctccggc atcgcggccg     840
cggttcgtcc ccttctcctc tatatcctac tacgtccgaa ttaaattgac ctctcccttc     900
aggcggatgg taccatctac gtgaatgaag gccgccctgc cgaagaaggt cgcaattgta     960
tcgtcgaatg gcgcaacaac cagccccgtg acgttttacc agctgcctac agtgcccgca    1020
cagccgtcca cggctacggc ggcgcggcgt tcaacaccac gtcagacgga aaggtgatct    1080
tcgcagactg gaaaactcac ggggtgtata tacttgatcc tgccacttgt gatgtaacag    1140
cagccgtgga accagacgaa aagatctggt acgctgcgtt caattcccac cccaagagac    1200
cagaattggt gtttgctatc agggaggatc accacggcaa ggaggtggtc aatgagcttg    1260
tcgtaatcaa taccgggaat aagaaggtgg aggttgcagc gacgggagcg gacttttact    1320
cgcatcccac gttcagtcct gctggtgata gagtgtcttg gatccagtgg aaccatcccg    1380
agatgccgtg gacgggaact gagttgtttt ccgcaccgtg gaaggatgag aaggttggaa    1440
cccctgtgaa attggcaggg aatggcgaag aagaaagtat cttgcaaccg agatggggac    1500
cagacggaac cttgttcttt gtgtcggatc gcactggata ttggcagttt tatcgctgga    1560
gcccggatga aagtgatgag cccgcgcta tcgttattga aggcctggag aagggcgagt    1620
tcgctcaccc agaatggctc ctgggatcgt atgactccta accctcctgc tcacatagta    1680
tatatctaac acgatgcagt tgcacatatg ttcttccaaa cgccaacaca attgttgcag    1740
```

-continued

```
cctggacgca aaacgcaacg gagcgtctcg tcatcattga cctcgagaaa aacacctata   1800
ccttccccgc ccacatcgca tcgctcactg gcatccaaca cagcgccgtg gccctgacat   1860
ctcccaccag cattgccgtc attgccagca ctcccactgc tcccagcact gtctaccaca   1920
tctctctcac caacaacgat gccttcgcgc caaccgtcct ccgctcctcc acctcagtca   1980
ccatttccga cacttatttt tctcgtgccc aacacatctc attcccgcgc accatctcca   2040
cccatcctga tactctctcc catgcatttt tcctccctcc cacgaatcct aagtacagca   2100
gtgccccggg cgagcttccc ccgctcatca ttaccattca cggcgggccc accatccaca   2160
ccgaccccgg ccttagcatg atgtggcagt actacaccac acgaggatat gccgttgccc   2220
tgctcaacta cgccggctcc tctggctacg tcgtgcctta ccgcaaactt cttaatggaa   2280
gttgggtgt gctcgacgtg cacgacgctg cagactgtgc ccgctacctg atctccgaag   2340
gcaaggtgca cccgtcccgc attggcatca ctggcgttag ttccggtgga tacgccactc   2400
tccaggcaat ctgcatgttc ccgactctct tcactggtgc agttagcgtc tctggcatta   2460
gtgatgtcga agccctcgtg gccgaaacac acaagttcga aagtcactat gccttccgcc   2520
tactattcga tgataaggtg ccggagactg aagaagagaa gcggaaggtg tatcgcgagc   2580
ggagccccag gttccatgca gacaaaatca aggccaaact gctgttgttg cagggcacgg   2640
acgatgagat tgtgccgttg aaccaagcgc aggcgatggc tgatgatgtc cagcgcagcg   2700
gcggggtggc caagttggtg atctttgagg gcgagggaca tgggtacccg cggaaggcgg   2760
agaatggctt gcaggctaag gaggtggaag agggctggtg gaaggtgaac ttggccgagg   2820
tcaatgggga atgagtgtga tactagcaga ttttgttgtg gattggtaca acagagtatc   2880
aagcacaggg ggccatccag tgaaagagat gtaagctact aggcacatct acgttctaga   2940
atatagaaag tgtcgtgatc tcctccatca ctacaaccaa atactcgtaa aaatagactg   3000
aagttcttcg cgaccccccaa gctcgtgaga caggccagta aacccaacca acaagtcacc   3060
gaacactcct agagatcgat caatcattat gcctcgccca ctaacccgat agaacaaagc   3120
taccctagat ggtcggtttt caatatactc cacacctatt cgtccataaa cagaccaggg   3180
actaaccaac taaaatatcc aaatccaacc aatgagttca gttcagcctt cattctcatc   3240
acacactaca tataaagaaa agagaataca cgctaatcct cacagctaca cgccccacac   3300
aaaaaaaaga caaaaatgct cacactcgga ttcgaaccga ggatctcatg attactagtc   3360
atgcgcttta ccaactaagc catgcgagca attgatgctg ctgatgcaga atattatgct   3420
atacagacca accttagagt atcatcctag tgctcaatcg gctatgcagt cactccacac   3480
caccgaaata caaagaacag atataatcca agtcgttata catacagcat gccggaatag   3540
aatctaaatt gactagccag ccagtctaca ggtactcggg ctacgcactg cagccaagac   3600
accgagatgg ataaattaag aacggcgacg gtgtggttct cgtggccgga tgctatcagg   3660
atttaatatg gaatggatga ccgggcttca ctgaaacccg agatatgacg tacatagtag   3720
caacttatta gattgtggtc gccgaggtct tttgtcggtg tacaagggt ttagttagta   3780
gtgaccggat cgggatctgt tggtgttgaa tgcgtcgggg acggtggtgg tgtttgtgga   3840
gaaagggggtg aatgacatat gatggctttt gttccgtact ttttggatta actttgtttt   3900
gctgtcggtg atagataagc tt                                             3922
```

<210> SEQ ID NO 2
<211> LENGTH: 663
<212> TYPE: PRT
<213> ORGANISM: Aspergillus niger N400

-continued

```
<400> SEQUENCE: 2

Met Ala Thr Pro Ala Glu Ala Gln Thr Ala Pro Phe Gly Thr Trp Asp
 1               5                  10                  15

Ser Pro Ile Thr Ala Ala Thr Leu Thr Ser Lys Gly Ile Ser Phe Ser
            20                  25                  30

Gly Ile Ala Ala Ala Asp Gly Thr Ile Tyr Val Asn Glu Gly Arg
        35                  40                  45

Pro Ala Glu Glu Gly Arg Asn Cys Ile Val Glu Trp Arg Asn Asn Gln
    50                  55                  60

Pro Ala Asp Val Leu Pro Ala Ala Tyr Ser Ala Arg Thr Ala Val His
65                  70                  75                  80

Gly Tyr Gly Gly Ala Ala Phe Asn Thr Thr Ser Asp Gly Lys Val Ile
                85                  90                  95

Phe Ala Asp Trp Lys Thr His Gly Val Tyr Ile Leu Asp Pro Ala Thr
            100                 105                 110

Cys Asp Val Thr Ala Ala Val Glu Pro Asp Glu Lys Ile Trp Tyr Ala
            115                 120                 125

Ala Phe Asn Ser His Pro Lys Arg Pro Glu Leu Val Phe Ala Ile Arg
    130                 135                 140

Glu Asp His His Gly Lys Glu Val Asn Glu Leu Val Val Ile Asn
145                 150                 155                 160

Thr Gly Asn Lys Lys Val Glu Val Ala Ala Thr Gly Ala Asp Phe Tyr
                165                 170                 175

Ser His Pro Thr Phe Ser Pro Ala Gly Asp Arg Val Ser Trp Ile Gln
            180                 185                 190

Trp Asn His Pro Glu Met Pro Trp Thr Gly Thr Glu Leu Phe Ser Ala
            195                 200                 205

Pro Trp Lys Asp Glu Lys Val Gly Thr Pro Val Lys Leu Ala Gly Asn
    210                 215                 220

Gly Glu Glu Glu Ser Ile Leu Gln Pro Arg Trp Gly Pro Asp Gly Thr
225                 230                 235                 240

Leu Phe Phe Val Ser Asp Arg Thr Gly Tyr Trp Gln Phe Tyr Arg Trp
                245                 250                 255

Ser Pro Asp Glu Ser Asp Glu Pro Arg Ala Ile Val Ile Glu Gly Leu
            260                 265                 270

Glu Lys Gly Glu Phe Ala His Pro Glu Trp Leu Leu Gly Ser Cys Thr
        275                 280                 285

Tyr Val Leu Pro Asn Ala Asn Thr Ile Val Ala Ala Trp Thr Gln Asn
    290                 295                 300

Ala Thr Glu Arg Leu Val Ile Ile Asp Leu Glu Lys Asn Thr Tyr Thr
305                 310                 315                 320

Phe Pro Ala His Ile Ala Ser Leu Thr Gly Ile Gln His Ser Ala Val
                325                 330                 335

Ala Leu Thr Ser Pro Thr Ser Ile Ala Val Ile Ala Ser Thr Pro Thr
            340                 345                 350

Ala Pro Ser Thr Val Tyr His Ile Ser Leu Thr Asn Asn Asp Ala Phe
        355                 360                 365

Ala Pro Thr Val Leu Arg Ser Ser Thr Ser Val Thr Ile Ser Asp Thr
    370                 375                 380

Tyr Phe Ser Arg Ala Gln His Ile Ser Phe Pro Arg Thr Ile Ser Thr
385                 390                 395                 400

His Pro Asp Thr Leu Ser His Ala Phe Phe Leu Pro Pro Thr Asn Pro
                405                 410                 415
```

-continued

```
Lys Tyr Ser Ser Ala Pro Gly Glu Leu Pro Pro Leu Ile Ile Thr Ile
                420                 425                 430

His Gly Gly Pro Thr Ile His Thr Asp Pro Gly Leu Ser Met Met Trp
                435                 440                 445

Gln Tyr Tyr Thr Thr Arg Gly Tyr Ala Val Ala Leu Leu Asn Tyr Ala
            450                 455                 460

Gly Ser Ser Gly Tyr Gly Arg Ala Tyr Arg Lys Leu Leu Asn Gly Ser
465                 470                 475                 480

Trp Ser Val Leu Asp Val His Asp Ala Ala Asp Cys Ala Arg Tyr Leu
                485                 490                 495

Ile Ser Glu Gly Lys Val His Pro Ser Arg Ile Gly Ile Thr Gly Val
                500                 505                 510

Ser Ser Gly Gly Tyr Ala Thr Leu Gln Ala Ile Cys Met Phe Pro Thr
            515                 520                 525

Leu Phe Thr Gly Ala Val Ser Val Ser Gly Ile Ser Asp Val Glu Ala
        530                 535                 540

Leu Val Ala Glu Thr His Lys Phe Glu Ser His Tyr Ala Phe Arg Leu
545                 550                 555                 560

Leu Phe Asp Asp Lys Val Pro Glu Thr Glu Glu Lys Arg Lys Val
                565                 570                 575

Tyr Arg Glu Arg Ser Pro Arg Phe His Ala Asp Lys Ile Lys Ala Lys
                580                 585                 590

Leu Leu Leu Leu Gln Gly Thr Asp Asp Glu Ile Val Pro Leu Asn Gln
                595                 600                 605

Ala Gln Ala Met Ala Asp Asp Val Gln Arg Ser Gly Gly Val Ala Lys
            610                 615                 620

Leu Val Ile Phe Glu Gly Glu Gly His Gly Tyr Pro Arg Lys Ala Glu
625                 630                 635                 640

Asn Gly Leu Gln Ala Lys Glu Val Glu Glu Gly Trp Trp Lys Val Asn
                645                 650                 655

Leu Ala Glu Val Asn Gly Glu
                660
```

<210> SEQ ID NO 3
<211> LENGTH: 1260
<212> TYPE: DNA
<213> ORGANISM: Aspergillus niger NRRL 3112

<400> SEQUENCE: 3

```
tcgcgggaac accgcggaac taatctggct ggtggatgtc acaacgatgc ttgtgctcag    60
ttcccctccc tgctaaattt cacccggtac ctgattattg cactacttca accccctcat   120
ccggccacgt ccatctttca ttttacgccc tccaaaaata tttcatccat tcactcactt   180
tctaacacat ccccaatatt tcaagtcaac caaatggcta cccccgcaga acctcagaca   240
gctcccttcg gcacttggga cagtcccatt acagccgcaa ccctgacgtc aaaggcatc    300 agtttctccg gcatcgcggc cacagttcgt ccccttctcc tctgtatcct actacgtcga   360
attaaattga cctctccctg caggcggatg gtaccatcta cgtgaatgaa ggccgccctg   420
ccgaagaagg tcgcaattgt attgtcgaat ggcgcaacaa ccagccccgt gacgttttac   480
cagctgccta cagtgcccgc acagccgtcc acgctacgg cggcgcggcg ttaacacca   540 cgtcagacgg aaaggtgatc ttcgcagact ggaaaactca cggggtgtat atccttgatc   600
ctgccacttg tgatgtaaca gcagccgtgg aaccggacga aaagatctgg tacgctgcgt   660
tcaattccca ccccaagaga ccagaattgg tgtttgctat cagggaggat caccacggca   720
```

```
aggaggtggt caatgagctt gttgtaatca ataccgggaa taagaaggtg gaggttgcag     780
cgacgggagc ggacttttac tcgcatccca cgttcagccc tgctggtgat agagtgtctt     840
ggatccagtg gaaccatccc gagatgccgt ggacgggaac tgagttgttt tccgcaccgt     900
ggaaggatga aaggttgga accctgtga aattggcagg gaatggcgat gaagaaagta      960
tcttgcagcc gagatgggga ccagacggaa ccttgttctt tgtgtcggat cgcactggat    1020
attggcagtt ttatcgctgg agcccggatg gaagtgatga gccccgtgct atcgttattg    1080
aaggcctgga gaagggcgag ttcgctcacc cagaatggct cttgggatcg tatgactcct    1140
aaccctcttg ctcacatagt atatatctaa cacgatgcag ttgcacatat gttcttccaa    1200
acgccaacac gattgttgca gcctggacgc agaacgcaac ggagcgtctc gtcatcattg    1260
```

<210> SEQ ID NO 4
<211> LENGTH: 17
<212> TYPE: DNA
<213> ORGANISM: Artificial sequence
<220> FEATURE:
<223> OTHER INFORMATION: Forward primer Sap1
<220> FEATURE:
<221> NAME/KEY: misc_feature
<222> LOCATION: (1)..(17)
<223> OTHER INFORMATION: n = a, t, c, or g

<400> SEQUENCE: 4
sntggathca rtggaay                                                    17

<210> SEQ ID NO 5
<211> LENGTH: 15
<212> TYPE: DNA
<213> ORGANISM: Artificial sequence
<220> FEATURE:
<223> OTHER INFORMATION: Reverse primer SAP-2

<400> SEQUENCE: 5
rttccaytgd atcca                                                      15

<210> SEQ ID NO 6
<211> LENGTH: 17
<212> TYPE: DNA
<213> ORGANISM: Artificial sequence
<220> FEATURE:
<223> OTHER INFORMATION: Forward primer Sap-3
<220> FEATURE:
<221> NAME/KEY: misc_feature
<222> LOCATION: (1)..(17)
<223> OTHER INFORMATION: n = a, t, c, or g

<400> SEQUENCE: 6
tggggnccng ayggnac                                                    17

<210> SEQ ID NO 7
<211> LENGTH: 17
<212> TYPE: DNA
<213> ORGANISM: Artificial sequence
<220> FEATURE:
<223> OTHER INFORMATION: Reverse primer SAP-4
<220> FEATURE:
<221> NAME/KEY: misc_feature
<222> LOCATION: (1)..(17)
<223> OTHER INFORMATION: n = a, t, c, or g

<400> SEQUENCE: 7
gtnccrtcng gnccca                                                     17

```
<210> SEQ ID NO 8
<211> LENGTH: 20
<212> TYPE: DNA
<213> ORGANISM: Artificial sequence
<220> FEATURE:
<223> OTHER INFORMATION: Forward primer SAP-5
<220> FEATURE:
<221> NAME/KEY: misc_feature
<222> LOCATION: 6, 15
<223> OTHER INFORMATION: n = inosine
<220> FEATURE:
<221> NAME/KEY: misc_feature
<222> LOCATION: 12, 18
<223> OTHER INFORMATION: n = a, t, c, or g

<400> SEQUENCE: 8
garccncara cngcnccntt                                          20

<210> SEQ ID NO 9
<211> LENGTH: 20
<212> TYPE: DNA
<213> ORGANISM: Artificial sequence
<220> FEATURE:
<223> OTHER INFORMATION: Forward primer SAP-6
<220> FEATURE:
<221> NAME/KEY: misc_feature
<222> LOCATION: 12
<223> OTHER INFORMATION: n = inosine
<220> FEATURE:
<221> NAME/KEY: misc_feature
<222> LOCATION: 3, 6, 15
<223> OTHER INFORMATION: n = a, t, c, or g

<400> SEQUENCE: 9
gcnccnttyg gnacntggga                                          20

<210> SEQ ID NO 10
<211> LENGTH: 20
<212> TYPE: DNA
<213> ORGANISM: Artificial sequence
<220> FEATURE:
<223> OTHER INFORMATION: Synthetic forward primer SAP-7
<220> FEATURE:
<221> NAME/KEY: misc_feature
<222> LOCATION: 9
<223> OTHER INFORMATION: n = inosine

<400> SEQUENCE: 10
gartayytnt tygaraayga                                          20

<210> SEQ ID NO 11
<211> LENGTH: 20
<212> TYPE: DNA
<213> ORGANISM: Artificial sequence
<220> FEATURE:
<223> OTHER INFORMATION: Reverse primer SAP-8
<220> FEATURE:
<221> NAME/KEY: misc_feature
<222> LOCATION: 12
<223> OTHER INFORMATION: n = inosine

<400> SEQUENCE: 11
tcrttytcra anarrtaytc                                          20

<210> SEQ ID NO 12
<211> LENGTH: 16
<212> TYPE: PRT
<213> ORGANISM: Aspergillus niger NRRL 3112
```

```
<400> SEQUENCE: 12

Ser Arg Val Glu Tyr Leu Phe Glu Asn Glu Arg Leu Pro Leu Asp Leu
 1               5                  10                  15

<210> SEQ ID NO 13
<211> LENGTH: 17
<212> TYPE: DNA
<213> ORGANISM: Artificial sequence
<220> FEATURE:
<223> OTHER INFORMATION: Forward primer SAP9

<400> SEQUENCE: 13
ccgcaaccct gacgtcc                                                        17

<210> SEQ ID NO 14
<211> LENGTH: 17
<212> TYPE: DNA
<213> ORGANISM: Artificial sequence
<220> FEATURE:
<223> OTHER INFORMATION: Reverse primer SAP10

<400> SEQUENCE: 14
accagggctg aacgtgg                                                        17

<210> SEQ ID NO 15
<211> LENGTH: 17
<212> TYPE: DNA
<213> ORGANISM: Artificial sequence
<220> FEATURE:
<223> OTHER INFORMATION: Forward primer ApsC 11

<400> SEQUENCE: 15
tcgcgggaac accgcgg                                                        17

<210> SEQ ID NO 16
<211> LENGTH: 17
<212> TYPE: DNA
<213> ORGANISM: Artificial sequence
<220> FEATURE:
<223> OTHER INFORMATION: Reverse primer ApsC 12

<400> SEQUENCE: 16
caatgatgac gagacgc                                                        17

<210> SEQ ID NO 17
<211> LENGTH: 23
<212> TYPE: DNA
<213> ORGANISM: Artificial sequence
<220> FEATURE:
<223> OTHER INFORMATION: RT reaction primer ApsC 13

<400> SEQUENCE: 17
gttccactgg atccaagaca ctc                                                 23

<210> SEQ ID NO 18
<211> LENGTH: 17
<212> TYPE: DNA
<213> ORGANISM: Artificial sequence
<220> FEATURE:
<223> OTHER INFORMATION: Nested primer ApsC 17

<400> SEQUENCE: 18
tgcggtaggc acgaccg                                                        17
```

-continued

```
<210> SEQ ID NO 19
<211> LENGTH: 17
<212> TYPE: DNA
<213> ORGANISM: Artificial sequence
<220> FEATURE:
<223> OTHER INFORMATION: Nested primer ApsC 18

<400> SEQUENCE: 19
ctctttcact ggatggc                                                  17

<210> SEQ ID NO 20
<211> LENGTH: 17
<212> TYPE: DNA
<213> ORGANISM: Artificial sequence
<220> FEATURE:
<223> OTHER INFORMATION: Reverse primer ApsC 19

<400> SEQUENCE: 20
ggctcctggg atcttgc                                                  17

<210> SEQ ID NO 21
<211> LENGTH: 24
<212> TYPE: DNA
<213> ORGANISM: Artificial sequence
<220> FEATURE:
<223> OTHER INFORMATION: Poly-T primer

<400> SEQUENCE: 21
tttttttttt tttttttttt tttv                                          24

<210> SEQ ID NO 22
<211> LENGTH: 637
<212> TYPE: PRT
<213> ORGANISM: Synechocystis sp.

<400> SEQUENCE: 22
```

Met Ile Ser Met Thr Thr Lys Gln Ile Ala Pro Tyr Gly Ser Trp Arg
1               5                   10                  15

Ser Pro Ile Thr Ala Asp Ala Leu Leu Ala Gly Ser Ile Gly Leu Gly
            20                  25                  30

Ala Val Gln Asn Ser Gly Glu Asp Val Phe Trp Leu Glu Ala Arg Pro
        35                  40                  45

Ala Glu Lys Gly Arg Asn Val Leu Val His Arg Gln Pro Asp Gly Thr
    50                  55                  60

Val Arg Asp Val Thr Pro Ala Pro Phe Asn Val Arg Thr Arg Val His
65                  70                  75                  80

Glu Tyr Gly Gly Gly Ala Phe Leu Val Thr Ala Asp Gly Val Tyr Phe
                85                  90                  95

Ser Asn Phe Ser Asp Gln Gln Val Tyr Val Gln Gly Val Gly Gln Glu
            100                 105                 110

Pro Gln Arg Leu Thr Asn Arg Pro Asp Cys Arg Phe Ala Asp Phe Val
        115                 120                 125

Leu Asp Gln Pro Arg Gln Arg Leu Ile Ala Val Gly Glu Arg His His
    130                 135                 140

Ser Glu Ala Lys Glu Pro Glu Asn Phe Leu Ala Ala Ile Ser Leu Glu
145                 150                 155                 160

Asn Gly Glu Val Thr Thr Ile Ala Thr Val His Asp Phe Tyr Ser Ser
                165                 170                 175

Pro Arg Leu Ser Pro Asp Gly Gln Lys Leu Ala Trp Ile Thr Trp Asp
            180                 185                 190

```
His Pro His Met Pro Trp Asp Ala Thr Gln Leu Trp Leu Ala Asp Ile
    195                 200                 205

Asp Gln Ala Gly Asn Leu Ser Asn Leu Lys Ile Ile Ala Gly Gly Ala
    210                 215                 220

Gly Asn Glu Ser Ile His Glu Pro Gly Trp Ser Pro Asp Gly Ser Leu
225                 230                 235                 240

Tyr Phe Val Gly Asp Arg Thr Asp Trp Trp Asn Leu Tyr Arg Tyr His
                245                 250                 255

Lys Gly Glu Val Asp Asn Val Phe Pro Leu Asp Ala Glu Phe Ala Tyr
                260                 265                 270

Pro His Trp Val Phe Gly Leu Arg Ser Tyr Thr Phe Val Asp Thr Asp
            275                 280                 285

Thr Ile Leu Cys Thr Phe Thr Gly Asp Gly Ala Trp Gly Leu Gly Lys
        290                 295                 300

Leu Lys Pro Ser Arg Lys Gly Leu Ser Ile Leu Gly Leu Pro Tyr Ser
305                 310                 315                 320

Asn Tyr Ser Ser Leu Cys Ser Asp Gly Lys Thr Leu Trp Phe Ile Gly
                325                 330                 335

Ser Gly Pro Thr Thr Ser Ser Ala Val Val Ala Leu Ala Val Glu Ala
            340                 345                 350

Gly Glu Thr Glu Ile Leu Lys Val Ala Ser Asp Phe Thr Leu Asp Pro
        355                 360                 365

Ala Tyr Leu Ala Gly Pro Gln Ala Ile Ser Phe Ser Gly Asp Asp Gly
    370                 375                 380

Gly Thr Ala His Ala Trp Tyr Tyr Pro Pro Thr Asn Gly Asp Phe Arg
385                 390                 395                 400

Gly Pro Ser Asp Ala Leu Pro Pro Leu Leu Val Lys Ser His Gly Gly
                405                 410                 415

Pro Thr Ala Ala Ala Gly Asn Ser Leu Ser Leu Lys Ile Gln Tyr Trp
            420                 425                 430

Thr Ser Arg Gly Phe Ala Tyr Val Asp Val Asn Tyr Gly Gly Ser Thr
        435                 440                 445

Gly Tyr Gly Arg Asp Tyr Arg Gly Arg Leu Asn Gly Gln Trp Gly Ile
    450                 455                 460

Val Asp Val Ala Asp Cys Val Asn Ala Ala Arg Tyr Leu Ala Asp Gln
465                 470                 475                 480

Gly Leu Val Asp Gly Glu Gln Leu Ala Ile Ser Gly Gly Ser Ala Gly
                485                 490                 495

Gly Tyr Thr Thr Leu Ala Ala Leu Thr Phe His Asn Val Phe Lys Ala
            500                 505                 510

Gly Ala Ser Tyr Tyr Gly Val Ser Asp Leu Thr Ala Leu Ala Thr Asp
        515                 520                 525

Thr His Lys Phe Glu Ala Arg Tyr Leu Asp Gly Leu Ile Gly Pro Tyr
    530                 535                 540

Pro Glu Arg Lys Asp Leu Tyr Glu Arg Arg Ser Pro Val Asn His Ala
545                 550                 555                 560

Asp Gln Leu Thr Cys Pro Val Ile Phe Phe Gln Gly Leu Glu Asp Lys
                565                 570                 575

Val Val Pro Pro Asn Gln Thr Glu Met Met Val Gln Ala Leu Lys Ala
            580                 585                 590

Lys Gly Ile Lys Val Glu Tyr Val Ala Phe Pro Glu Glu Gln His Gly
        595                 600                 605
```

```
Phe Arg Met Ala Ala Asn Ile Lys Lys Ala Leu Glu Ser Glu Leu Ala
    610                 615                 620

Phe Tyr Gly Glu Val Phe Gly Phe Thr Pro Ala Lys Asn
625                 630                 635

<210> SEQ ID NO 23
<211> LENGTH: 629
<212> TYPE: PRT
<213> ORGANISM: Caenorhabditis elegans

<400> SEQUENCE: 23

Met Ala Thr Glu Ala Val Tyr Gly Ser Trp Asp Ser Pro Ile Thr Pro
  1               5                  10                  15

Asp Leu Phe Gly Lys Cys Asn Cys Lys Ser Ile Cys Glu Met Gln Val
             20                  25                  30

Val Gly Gly Asn Val Tyr Trp Ile Glu Gln Asn Ser Val Thr Gly Lys
         35                  40                  45

Arg Glu Leu Tyr Ser Lys Pro Thr Asn Gly Asp Thr Arg Thr Arg Trp
 50                  55                  60

Ala Asp Gly Gln Ser Val Gln Thr Ala Ile His Glu Tyr Gly Gly Gly
 65                  70                  75                  80

Ala Leu His Val Leu Ala Asp Gly Ser Val Leu Phe Ala Thr Ile Glu
                 85                  90                  95

Gly Val Phe Tyr Gln Lys Ser Ala Asp Ser Gly Val Glu Gln Leu Ala
            100                 105                 110

Glu Gly Asn Asn Arg Met Phe Arg Phe Ser Asp Phe Ser Ala Thr Asp
            115                 120                 125

Thr His Val Phe Cys Val Asn Glu Thr His Gln Ala Asp Ala Lys Phe
130                 135                 140

Pro Glu Asn Arg Leu Ile Ser Ile Asp Arg Ala Thr Lys Asn Gln Asn
145                 150                 155                 160

Val Ile Ala His Gly Ala Asp Phe Tyr Ala Tyr Pro Arg Val Ser Pro
                165                 170                 175

Asp Gly Lys Lys Leu Val Trp Met Gln Trp Ser Leu Pro Asn Met Pro
            180                 185                 190

Trp Asp Glu Thr Ser Ile Arg Met Ala Asp Leu Lys Gly Gly Glu Ser
            195                 200                 205

Ser Asn Glu Val Thr Leu Lys Asp Gly Thr Gly Lys Gln Ile Asn Tyr
210                 215                 220

Ser Glu Pro Thr Trp Asp Gly Asp Glu Leu Leu Thr Val Asn Asp Ser
225                 230                 235                 240

Thr Asn Trp Trp Asn Val Tyr Lys Ser Ala Ala Glu Pro Asn Ser Val
                245                 250                 255

Glu Lys Asn Leu Asn Pro Ile Gln Arg Glu Ile Ser Tyr Pro Leu Trp
            260                 265                 270

Gln Leu Gly Phe Arg Asn Tyr Val Leu Asn Lys Lys Tyr Leu Val Met
            275                 280                 285

Asn Ala Asp Gly Ile Leu Tyr Val Arg Ser Gly Asp Val Thr Val Glu
290                 295                 300

Ile Pro Thr Pro Gly Tyr Thr Val Phe Gly Tyr Leu Ser Leu Asp Gln
305                 310                 315                 320

Asn Gly Ser Asp Leu Phe Ala Ile Ala Ser Gly Pro Lys Arg Ala Ser
                325                 330                 335

Ser Val Ile Ser Ile Asp Leu Ala Asn Lys Asn Phe Pro Leu Lys Val
            340                 345                 350
```

```
His Arg Glu Ser Arg Asp Ser Glu Ile Asp Ala Leu Glu Ile Ser
        355                 360                 365

Glu Pro Glu Phe Val Phe Lys Ser Asp Gly Val Asp Val Ser Ala
    370                 375                 380

Gly Thr Leu Pro Pro Val Leu Leu Gly His Gly Gly Pro Thr Ala
385                 390                 395                 400

Pro Ala Gln Asn Asn Leu Asp Leu Lys Lys Gln Phe Phe Thr Ser Arg
                405                 410                 415

Gly Ile Ala Val Phe Asp Val Asn Tyr Arg Gly Ser Thr Gly Phe Gly
            420                 425                 430

Thr Glu Phe Arg Arg Met Leu Tyr Lys Asn Cys Gly Val Ala Asp Arg
        435                 440                 445

Asp Asp Met Leu Asn Gly Ala Lys Ala Leu Val Glu Gln Gly Lys Val
    450                 455                 460

Asp Ala Glu Lys Val Leu Ile Thr Gly Ser Ser Ser Gly Gly Tyr Leu
465                 470                 475                 480

Ile Leu Ser Cys Leu Ile Ser Pro Lys Asn Ile Ile Lys Ala Val
                485                 490                 495

Ser Val Tyr Gly Val Ala Asp Leu Leu Ala Leu Asp Glu Asp Thr His
            500                 505                 510

Lys Leu Glu Arg Cys Tyr Asn Glu Met Leu Ile Gly Lys Tyr Pro Glu
        515                 520                 525

Gln Ala Ser Ile Tyr Glu Glu Arg Ser Pro Ile Tyr His Ile Asp Lys
    530                 535                 540

Ile Arg Thr Pro Ile Ala Phe Leu His Gly Arg Glu Asp Thr Val Val
545                 550                 555                 560

Pro Met Ser Gln Ser Ile Thr Met Tyr Glu Lys Ile Arg Ala Ser Gly
                565                 570                 575

Val Thr Thr Ala Leu Met Leu Phe Asp Gly Glu Gly His Gly Phe Arg
            580                 585                 590

Asn Gly Gln Val Ile Lys Glu Ser Thr Glu Ala Thr Phe Tyr Phe Leu
        595                 600                 605

Met Lys Ala Val Gly Ile Glu Pro Ser Ile Ser Ser Lys Ile Glu Ile
    610                 615                 620

Val Asn Pro Lys His
625

<210> SEQ ID NO 24
<211> LENGTH: 1260
<212> TYPE: DNA
<213> ORGANISM: Aspergillus niger N400 genomic sequence

<400> SEQUENCE: 24
tcgcgggaac accgcggaac taatctggct ggtggatgtc acaacgatgc ttgtgctcag      60
ttcccctccc tgctaaattt cacccggtac ctgattattg cactacttca acccctcat     120 ccggccacgt ccatctttct ttttacgccc tccaaaaata tttcatccat tcacttactc     180
tctaagacac tcccaatttt ccagtcaacc aaatggctac ccccgcagaa gctcagacag     240
ctcccttcgg cacttgggac agtcccatca cagccgcaac cctgacgtcc aaaggcatca     300
gtttctccgg catcgcggcc gcggttcgtc cccttctcct ctatatccta ctacgtccga     360
attaaattga cctctcccctt caggcggatg gtaccatcta cgtgaatgaa ggccgccctg     420
ccgaagaagg tcgcaattgt atcgtcgaat ggcgcaacaa ccagccccgt gacgttttac     480
cagctgccta cagtgcccgc acagccgtcc acggctacgg cggcgcggcg ttcaacacca     540
```

-continued

```
cgtcagacgg aaaggtgatc ttcgcagact ggaaaactca cggggtgtat atacttgatc    600
ctgccacttg tgatgtaaca gcagccgtgg aaccagacga aaagatctgg tacgctgcgt    660
tcaattccca ccccaagaga ccagaattgg tgtttgctat cagggaggat caccacggca    720
aggaggtggt caatgagctt gtcgtaatca ataccgggaa taagaaggtg gaggttgcag    780
cgacgggagc ggactttttac tcgcatccca cgttcagtcc tgctggtgat agagtgtctt    840
ggatccagtg gaaccatccc gagatgccgt ggacgggaac tgagttgttt tccgcaccgt    900
ggaaggatga gaaggttgga accctgtga aattggcagg gaatggcgaa gaagaaagta    960
tcttgcaacc gagatgggga ccagacgaa ccttgttctt tgtgtcggat cgcactggat    1020
attggcagtt ttatcgctgg agcccggatg aaagtgatga gccccgcgct atcgttattg    1080
aaggcctgga gaagggcgag ttcgctcacc cagaatggct cctgggatcg tatgactcct    1140
aaccctcctg ctcacatagt atatatctaa cacgatgcag ttgcacatat gttcttccaa    1200
acgccaacac aattgttgca gcctggacgc aaaacgcaac ggagcgtctc gtcatcattg    1260
```

```
<210> SEQ ID NO 25
<211> LENGTH: 7
<212> TYPE: PRT
<213> ORGANISM: Aspergillus niger NRRL 3112 fragment

<400> SEQUENCE: 25

Val Ser Trp Ile Gln Trp Asn
1               5

<210> SEQ ID NO 26
<211> LENGTH: 13
<212> TYPE: PRT
<213> ORGANISM: Aspergillus niger NRRL 3112 fragment

<400> SEQUENCE: 26

Trp Gly Pro Asp Gly Thr Leu Phe Phe Val Ser Asp Arg
1               5                   10

<210> SEQ ID NO 27
<211> LENGTH: 16
<212> TYPE: PRT
<213> ORGANISM: Aspergillus niger NRRL 3112 fragment

<400> SEQUENCE: 27

Ala Glu Pro Gln Thr Ala Pro Phe Gly Thr Trp Asp Ser Pro Ile Thr
1               5                   10                  15
```